United States Patent
DeBenedictis et al.

(10) Patent No.: US 10,524,956 B2
(45) Date of Patent: Jan. 7, 2020

(54) TEMPERATURE-DEPENDENT ADHESION BETWEEN APPLICATOR AND SKIN DURING COOLING OF TISSUE

(71) Applicant: Zeltiq Aesthetics, Inc., Pleasanton, CA (US)

(72) Inventors: Leonard C. DeBenedictis, Dublin, CA (US); Like Zeng, Pleasanton, CA (US); George Frangineas, Jr., Fremont, CA (US); Joel N. Jimenez Lozano, Dublin, CA (US)

(73) Assignee: Zeltiq Aesthetics, Inc., Pleasanton, CA (US)

( * ) Notice: Subject to any disclaimer, the term of this patent is extended or adjusted under 35 U.S.C. 154(b) by 381 days.

(21) Appl. No.: 15/400,885

(22) Filed: Jan. 6, 2017

(65) Prior Publication Data

US 2017/0196731 A1 Jul. 13, 2017

Related U.S. Application Data

(60) Provisional application No. 62/276,131, filed on Jan. 7, 2016.

(51) Int. Cl.
*A61F 7/00* (2006.01)
*A61F 7/02* (2006.01)

(52) U.S. Cl.
CPC .................. *A61F 7/02* (2013.01); *A61F 7/00* (2013.01); *A61F 7/007* (2013.01);
(Continued)

(58) Field of Classification Search
CPC combination set(s) only.
See application file for complete search history.

(56) References Cited

U.S. PATENT DOCUMENTS 681,806 A 9/1901 Mignault et al.
889,810 A 6/1908 Robinson et al.
(Continued)

FOREIGN PATENT DOCUMENTS

AU 2011253768 A1 6/2012
CA 2441489 A1 3/2005
(Continued)

OTHER PUBLICATIONS

"ThermaCool Monopolar Capacitive Radiofrequency, The one choice for nonablative tissue tightening and contouring", Thermage, Inc. Tech Brochure, Nov. 30, 2005, 8 pgs.
(Continued)

*Primary Examiner* — Joseph A Stoklosa
*Assistant Examiner* — Adam J Avigan
(74) *Attorney, Agent, or Firm* — Perkins Coie LLP

(57) ABSTRACT

A method and apparatus in accordance with a particular embodiment of the present invention includes applying adhesive onto skin of a human subject. An applicator is then brought into contact with the adhesive such the adhesive is disposed between the applicator and the subject's skin. The applicator is activated to cool a tissue region via the subject's skin, via the heat-transfer surface of the applicator, and via the adhesive. While the tissue region cools, the adhesive also cools, thereby reversibly strengthening adhesion between the subject's skin and the heat-transfer surface and forming a strong bond therebetween. The strengthened adhesion inhibits any movement of the applicator relative to the skin. After cooling the tissue region, the adhesive is warmed, thereby weakening the adhesion which allows the heat-transfer surface of the applicator to be easily separated from the skin.

27 Claims, 14 Drawing Sheets

(52) U.S. Cl.
CPC .......... A61F 2007/0009 (2013.01); A61F 2007/0014 (2013.01); A61F 2007/0056 (2013.01); A61F 2007/0075 (2013.01); A61F 2007/0087 (2013.01); A61F 2007/0093 (2013.01); A61F 2007/029 (2013.01); A61F 2007/0226 (2013.01); A61F 2007/0239 (2013.01)

(56) References Cited

U.S. PATENT DOCUMENTS

| | | |
|---|---|---|
| 2,516,491 A | 7/1950 | Swastek |
| 2,521,780 A | 9/1950 | Dodd et al. |
| 2,726,658 A | 12/1955 | Chessey |
| 2,766,619 A | 10/1956 | Tribus et al. |
| 2,851,602 A | 9/1958 | Cramwinckel et al. |
| 3,093,135 A | 6/1963 | Hirschhorn |
| 3,132,688 A | 5/1964 | Nowak |
| 3,133,539 A | 5/1964 | William et al. |
| 3,282,267 A | 11/1966 | Eidus |
| 3,502,080 A | 3/1970 | Hirschhorn |
| 3,587,577 A | 6/1971 | Zubkov et al. |
| 3,591,645 A | 7/1971 | Selwitz |
| 3,703,897 A | 11/1972 | Mack et al. |
| 3,710,784 A | 1/1973 | Taylor |
| 3,786,814 A | 1/1974 | Armao |
| 3,827,436 A | 8/1974 | Andera et al. |
| 3,942,519 A | 3/1976 | Shock |
| 3,948,269 A | 4/1976 | Zimmer |
| 3,986,385 A | 10/1976 | Johnston et al. |
| 3,993,053 A | 11/1976 | Grossan |
| 4,002,221 A | 1/1977 | Buchalter |
| 4,026,299 A | 5/1977 | Sauder |
| 4,140,130 A | 2/1979 | Storm |
| 4,149,529 A | 4/1979 | Copeland et al. |
| 4,178,429 A | 12/1979 | Scheffer |
| 4,202,336 A | 5/1980 | Van Gerven |
| 4,266,043 A | 5/1981 | Fujii et al. |
| 4,269,068 A | 5/1981 | Molina |
| 4,381,009 A | 4/1983 | Del Bon |
| 4,396,011 A | 8/1983 | Mack et al. |
| 4,459,854 A | 7/1984 | Richardson et al. |
| 4,483,341 A | 11/1984 | Witteles |
| 4,528,979 A | 7/1985 | Marchenko et al. |
| 4,531,524 A | 7/1985 | Mioduski |
| 4,548,212 A | 10/1985 | Leung |
| 4,555,313 A | 11/1985 | Duchane et al. |
| 4,585,002 A | 4/1986 | Kissin |
| 4,603,076 A | 7/1986 | Bowditch et al. |
| 4,614,191 A | 9/1986 | Perler et al. |
| 4,644,955 A | 2/1987 | Mioduski |
| 4,664,110 A | 5/1987 | Schanzlin |
| 4,700,701 A | 10/1987 | Montaldi |
| 4,718,429 A | 1/1988 | Smidt |
| 4,741,338 A | 5/1988 | Miyamae |
| 4,764,463 A | 8/1988 | Mason et al. |
| 4,802,475 A | 2/1989 | Weshahy |
| 4,832,022 A | 5/1989 | Tjulkov et al. |
| 4,846,176 A | 7/1989 | Golden |
| 4,850,340 A | 7/1989 | Onishi |
| 4,869,250 A | 9/1989 | Bitterly |
| 4,880,564 A | 11/1989 | Abel et al. |
| 4,905,697 A | 3/1990 | Heggs et al. |
| 4,906,463 A | 3/1990 | Cleary et al. |
| 4,930,317 A | 6/1990 | Klein |
| 4,935,345 A | 6/1990 | Guilbeau et al. |
| 4,961,422 A | 10/1990 | Marchosky et al. |
| 4,962,761 A | 10/1990 | Golden |
| 4,990,144 A | 2/1991 | Blott et al. |
| 5,007,433 A | 4/1991 | Hermsdoerffer et al. |
| 5,018,521 A | 5/1991 | Campbell et al. |
| 5,024,650 A | 6/1991 | Hagiwara et al. |
| 5,065,752 A | 11/1991 | Sessions et al. |
| 5,069,208 A | 12/1991 | Noppel et al. |
| 5,084,671 A | 1/1992 | Miyata et al. |
| 5,108,390 A | 4/1992 | Potocky et al. |
| 5,119,674 A | 6/1992 | Nielsen |
| 5,139,496 A | 8/1992 | Hed et al. |
| 5,143,063 A | 9/1992 | Fellner |
| 5,148,804 A | 9/1992 | Hill et al. |
| 5,158,070 A | 10/1992 | Dory |
| 5,169,384 A | 12/1992 | Bosniak et al. |
| 5,197,466 A | 3/1993 | Marchosky et al. |
| 5,207,674 A | 5/1993 | Hamilton |
| 5,221,726 A | 6/1993 | Dabi et al. |
| 5,264,234 A | 11/1993 | Windhab et al. |
| 5,277,030 A | 1/1994 | Miller |
| 5,314,423 A | 5/1994 | Seney et al. |
| 5,327,886 A | 7/1994 | Chiu |
| 5,330,745 A | 7/1994 | Mcdow et al. |
| 5,333,460 A | 8/1994 | Lewis et al. |
| 5,334,131 A | 8/1994 | Omandam et al. |
| 5,336,616 A | 8/1994 | Livesey et al. |
| 5,339,541 A | 8/1994 | Owens |
| 5,342,617 A | 8/1994 | Gold et al. |
| 5,351,677 A | 10/1994 | Kami et al. |
| 5,358,467 A | 10/1994 | Milstein et al. |
| 5,362,966 A | 11/1994 | Rosenthal et al. |
| 5,363,347 A | 11/1994 | Nguyen |
| 5,372,608 A | 12/1994 | Johnson |
| 5,386,837 A | 2/1995 | Sterzer |
| 5,411,541 A | 5/1995 | Bell et al. |
| 5,427,772 A | 6/1995 | Hagan et al. |
| 5,433,717 A | 7/1995 | Rubinsky et al. |
| 5,456,703 A | 10/1995 | Beeuwkes, III et al. |
| 5,472,416 A | 12/1995 | Blugerman et al. |
| 5,486,207 A | 1/1996 | Mahawili |
| 5,497,596 A | 3/1996 | Zatkulak |
| 5,501,655 A | 3/1996 | Rolt et al. |
| 5,505,726 A | 4/1996 | Meserol |
| 5,505,730 A | 4/1996 | Edwards et al. |
| 5,507,790 A | 4/1996 | Weiss |
| 5,514,105 A | 5/1996 | Goodman, Jr. et al. |
| 5,514,170 A | 5/1996 | Mauch |
| 5,516,505 A | 5/1996 | McDow |
| 5,531,742 A | 7/1996 | Barken |
| 5,562,604 A | 10/1996 | Yablon et al. |
| 5,571,801 A | 11/1996 | Segall et al. |
| 5,575,812 A | 11/1996 | Owens et al. |
| 5,603,221 A | 2/1997 | Maytal |
| 5,628,769 A | 5/1997 | Saringer |
| 5,634,890 A | 6/1997 | Morris |
| 5,634,940 A | 6/1997 | Panyard |
| 5,647,051 A | 7/1997 | Neer |
| 5,647,868 A | 7/1997 | Chinn |
| 5,650,450 A | 7/1997 | Lovette et al. |
| 5,651,773 A | 7/1997 | Perry et al. |
| 5,654,279 A | 8/1997 | Rubinsky et al. |
| 5,654,546 A | 8/1997 | Lindsay et al. |
| 5,660,836 A | 8/1997 | Knowlton et al. |
| 5,665,053 A | 9/1997 | Jacobs |
| 5,672,172 A | 9/1997 | Zupkas |
| 5,700,284 A | 12/1997 | Owens et al. |
| 5,725,483 A | 3/1998 | Podolsky |
| 5,733,280 A | 3/1998 | Avitall |
| 5,741,248 A | 4/1998 | Stern et al. |
| 5,746,736 A | 5/1998 | Tankovich |
| 5,755,663 A | 5/1998 | Larsen et al. |
| 5,755,753 A | 5/1998 | Knowlton et al. |
| 5,755,755 A | 5/1998 | Panyard |
| 5,759,182 A | 6/1998 | Varney et al. |
| 5,759,764 A | 6/1998 | Polovina et al. |
| 5,769,879 A | 6/1998 | Richards et al. |
| 5,785,955 A | 7/1998 | Fischer |
| 5,792,080 A | 8/1998 | Ookawa et al. |
| 5,800,490 A | 9/1998 | Patz et al. |
| 5,814,040 A | 9/1998 | Nelson et al. |
| 5,817,050 A | 10/1998 | Klein et al. |
| 5,817,149 A | 10/1998 | Owens et al. |
| 5,817,150 A | 10/1998 | Owens et al. |
| 5,830,208 A | 11/1998 | Muller et al. |
| 5,833,685 A | 11/1998 | Tortal et al. |
| 5,844,013 A | 12/1998 | Kenndoff et al. |
| 5,865,841 A | 2/1999 | Kolen et al. |

(56) References Cited

U.S. PATENT DOCUMENTS

| | | |
|---|---|---|
| 5,871,524 A | 2/1999 | Knowlton |
| 5,871,526 A | 2/1999 | Gibbs et al. |
| 5,885,211 A | 3/1999 | Eppstein et al. |
| 5,891,617 A | 4/1999 | Watson et al. |
| 5,895,418 A | 4/1999 | Saringer |
| 5,901,707 A | 5/1999 | Goncalves |
| 5,902,256 A | 5/1999 | Benaron |
| 5,919,219 A | 7/1999 | Knowlton et al. |
| 5,944,748 A | 8/1999 | Mager et al. |
| 5,948,011 A | 9/1999 | Knowlton et al. |
| 5,954,680 A | 9/1999 | Augustine et al. |
| 5,964,092 A | 10/1999 | Tozuka et al. |
| 5,964,749 A | 10/1999 | Eckhouse et al. |
| 5,967,976 A | 10/1999 | Larsen et al. |
| 5,980,561 A | 11/1999 | Kolen et al. |
| 5,986,167 A | 11/1999 | Arteman et al. |
| 5,989,286 A | 11/1999 | Owens et al. |
| 5,997,530 A | 12/1999 | Nelson et al. |
| 6,017,337 A | 1/2000 | Pira |
| 6,023,932 A | 2/2000 | Johnston |
| 6,032,675 A | 3/2000 | Rubinsky |
| 6,039,694 A | 3/2000 | Larson et al. |
| 6,041,787 A | 3/2000 | Rubinsky |
| 6,047,215 A | 4/2000 | McClure et al. |
| 6,049,927 A | 4/2000 | Thomas et al. |
| 6,051,159 A | 4/2000 | Hao et al. |
| 6,071,239 A | 6/2000 | Cribbs et al. |
| 6,074,415 A | 6/2000 | Der Ovanesian |
| 6,093,230 A | 7/2000 | Johnson et al. |
| 6,102,885 A | 8/2000 | Bass |
| 6,104,952 A | 8/2000 | Tu et al. |
| 6,104,959 A | 8/2000 | Spertell et al. |
| 6,106,517 A | 8/2000 | Zupkas |
| 6,113,558 A | 9/2000 | Rosenschein et al. |
| 6,113,559 A | 9/2000 | Klopotek |
| 6,113,626 A | 9/2000 | Clifton et al. |
| 6,120,519 A | 9/2000 | Weber et al. |
| 6,139,544 A | 10/2000 | Mikus et al. |
| 6,150,148 A | 11/2000 | Nanda et al. |
| 6,151,735 A | 11/2000 | Koby et al. |
| 6,152,952 A | 11/2000 | Owens et al. |
| 6,171,301 B1 | 1/2001 | Nelson et al. |
| 6,180,867 B1 | 1/2001 | Hedengren et al. |
| 6,226,996 B1 | 5/2001 | Weber et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van Vilsteren et al. |
| 6,311,090 B1 | 10/2001 | Knowlton |
| 6,311,497 B1 | 11/2001 | Chung |
| 6,312,453 B1 | 11/2001 | Stefanile et al. |
| 6,350,276 B1 | 2/2002 | Knowlton |
| 6,354,297 B1 | 3/2002 | Eiseman |
| 6,357,907 B1 | 3/2002 | Cleveland et al. |
| 6,375,673 B1 | 4/2002 | Clifton et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,401,722 B1 | 6/2002 | Krag |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,430,956 B1 | 8/2002 | Haas et al. |
| 6,438,424 B1 | 8/2002 | Knowlton |
| 6,438,954 B1 | 8/2002 | Goetz et al. |
| 6,438,964 B1 | 8/2002 | Giblin |
| 6,453,202 B1 | 9/2002 | Knowlton |
| 6,458,888 B1 | 10/2002 | Hood et al. |
| 6,461,378 B1 | 10/2002 | Knowlton |
| 6,470,216 B1 | 10/2002 | Knowlton |
| 6,471,693 B1 | 10/2002 | Carroll et al. |
| 6,475,211 B2 | 11/2002 | Chess et al. |
| 6,478,811 B1 | 11/2002 | Dobak, III et al. |
| 6,494,844 B1 | 12/2002 | Van Bladel et al. |
| 6,497,721 B2 | 12/2002 | Ginsburg et al. |
| 6,508,831 B1 | 1/2003 | Kushnir |
| 6,514,244 B2 | 2/2003 | Pope et al. |
| 6,519,964 B2 | 2/2003 | Bieberich |
| 6,523,354 B1 | 2/2003 | Tolbert |
| 6,527,765 B2 | 3/2003 | Kelman et al. |
| 6,527,798 B2 | 3/2003 | Ginsburg et al. |
| 6,544,248 B1 | 4/2003 | Bass |
| 6,547,811 B1 | 4/2003 | Becker et al. |
| 6,548,297 B1 | 4/2003 | Kuri-Harcuch et al. |
| 6,551,255 B2 | 4/2003 | Van Bladel et al. |
| 6,551,341 B2 | 4/2003 | Boylan et al. |
| 6,551,348 B1 | 4/2003 | Blalock et al. |
| 6,551,349 B2 | 4/2003 | Lasheras et al. |
| 6,569,189 B1 | 5/2003 | Augustine et al. |
| 6,585,652 B2 | 7/2003 | Lang et al. |
| 6,592,577 B2 | 7/2003 | Abboud et al. |
| 6,605,080 B1 | 8/2003 | Altshuler et al. |
| 6,607,498 B2 | 8/2003 | Eshel |
| 6,620,187 B2 | 9/2003 | Carson et al. |
| 6,620,188 B1 | 9/2003 | Ginsburg et al. |
| 6,620,189 B1 | 9/2003 | Machold et al. |
| 6,623,430 B1 | 9/2003 | Slayton et al. |
| 6,626,854 B2 | 9/2003 | Friedman et al. |
| 6,632,219 B1 | 10/2003 | Baranov et al. |
| 6,635,053 B1 | 10/2003 | Lalonde et al. |
| 6,643,535 B2 | 11/2003 | Damasco et al. |
| 6,645,162 B2 | 11/2003 | Friedman et al. |
| 6,645,229 B2 | 11/2003 | Matsumura et al. |
| 6,645,232 B2 | 11/2003 | Carson |
| 6,648,904 B2 | 11/2003 | Altshuler et al. |
| 6,656,208 B2 | 12/2003 | Grahn et al. |
| 6,660,027 B2 | 12/2003 | Gruszecki et al. |
| 6,662,054 B2 | 12/2003 | Kreindel et al. |
| 6,682,550 B2 | 1/2004 | Clifton et al. |
| 6,685,731 B2 | 2/2004 | Kushnir et al. |
| 6,694,170 B1 | 2/2004 | Mikus et al. |
| 6,695,874 B2 | 2/2004 | Machold et al. |
| 6,697,670 B2 | 2/2004 | Chornenky |
| 6,699,237 B2 | 3/2004 | Weber et al. |
| 6,699,266 B2 | 3/2004 | Lachenbruch et al. |
| 6,699,267 B2 | 3/2004 | Voorhees et al. |
| 6,718,785 B2 | 4/2004 | Bieberich |
| 6,741,895 B1 | 5/2004 | Gafni et al. |
| 6,743,222 B2 | 6/2004 | Durkin et al. |
| 6,746,474 B2 | 6/2004 | Saadat |
| 6,749,624 B2 | 6/2004 | Knowlton |
| 6,764,493 B1 | 7/2004 | Weber et al. |
| 6,764,502 B2 | 7/2004 | Bieberich |
| 6,789,545 B2 | 9/2004 | Littrup et al. |
| 6,795,728 B2 | 9/2004 | Chornenky et al. |
| 6,820,961 B2 | 11/2004 | Johnson |
| 6,821,274 B2 | 11/2004 | McHale et al. |
| 6,840,955 B2 | 1/2005 | Ein |
| 6,849,075 B2 | 2/2005 | Bertolero et al. |
| 6,878,144 B2 | 4/2005 | Altshuler et al. |
| 6,889,090 B2 | 5/2005 | Kreindel |
| 6,892,099 B2 | 5/2005 | Jaafar et al. |
| 6,904,956 B2 | 6/2005 | Noel |
| 6,918,903 B2 | 7/2005 | Bass |
| 6,927,316 B1 | 8/2005 | Faries, Jr. et al. |
| 6,942,022 B2 | 9/2005 | Blangetti et al. |
| 6,945,942 B2 | 9/2005 | Van Bladel et al. |
| 6,948,903 B2 | 9/2005 | Ablabutyan et al. |
| 6,969,399 B2 | 11/2005 | Schock et al. |
| 7,005,558 B1 | 2/2006 | Johansson et al. |
| 7,006,874 B2 | 2/2006 | Knowlton et al. |
| 7,022,121 B2 | 4/2006 | Stern et al. |
| 7,037,326 B2 | 5/2006 | Lee |
| 7,054,685 B2 | 5/2006 | Dimmer et al. |
| 7,060,061 B2 | 6/2006 | Altshuler et al. |
| 7,077,858 B2 | 7/2006 | Fletcher et al. |
| 7,081,111 B2 | 7/2006 | Svaasand et al. |
| 7,083,612 B2 | 8/2006 | Littrup et al. |
| 7,096,204 B1 | 8/2006 | Chen et al. |
| 7,112,712 B1 | 9/2006 | Ancell |

(56) References Cited

U.S. PATENT DOCUMENTS

| | | |
|---|---|---|
| 7,115,123 B2 | 10/2006 | Knowlton et al. |
| 7,141,049 B2 | 11/2006 | Stern et al. |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |
| 7,229,436 B2 | 6/2007 | Stern et al. |
| 7,258,674 B2 | 8/2007 | Cribbs et al. |
| 7,267,675 B2 | 9/2007 | Stern et al. |
| 7,276,058 B2 | 10/2007 | Altshuler et al. |
| 7,318,821 B2 | 1/2008 | Lalonde et al. |
| 7,331,951 B2 | 2/2008 | Eshel et al. |
| 7,347,855 B2 | 3/2008 | Eshel et al. |
| 7,367,341 B2 | 5/2008 | Anderson et al. |
| 7,532,201 B2 | 5/2009 | Quistgaard et al. |
| 7,572,268 B2 | 8/2009 | Babaev |
| 7,604,632 B2 | 10/2009 | Howlett et al. |
| 7,613,523 B2 | 11/2009 | Eggers et al. |
| 7,615,016 B2 | 11/2009 | Barthe et al. |
| 7,713,266 B2 | 5/2010 | Elkins et al. |
| 7,780,656 B2 | 8/2010 | Tankovich |
| 7,799,018 B2 | 9/2010 | Goulko |
| 7,824,437 B1 | 11/2010 | Saunders |
| 7,828,831 B1 | 11/2010 | Tanhehco et al. |
| 7,850,683 B2 | 12/2010 | Elkins et al. |
| 7,854,754 B2 | 12/2010 | Ting et al. |
| 7,862,558 B2 | 1/2011 | Elkins et al. |
| RE42,277 E | 4/2011 | Jaafar et al. |
| 7,938,824 B2 | 5/2011 | Chornenky et al. |
| 7,959,657 B1 | 6/2011 | Harsy et al. |
| 7,963,959 B2 | 6/2011 | Da Silva et al. |
| 7,967,763 B2 | 6/2011 | Deem et al. |
| 7,993,330 B2 | 8/2011 | Goulko |
| 7,998,137 B2 | 8/2011 | Elkins et al. |
| RE42,835 E | 10/2011 | Chornenky et al. |
| RE43,009 E | 12/2011 | Chornenky et al. |
| 8,133,180 B2 | 3/2012 | Slayton et al. |
| 8,133,191 B2 | 3/2012 | Rosenberg et al. |
| 8,192,474 B2 | 6/2012 | Levinson |
| 8,246,611 B2 | 8/2012 | Paithankar et al. |
| 8,275,442 B2 | 9/2012 | Allison |
| 8,285,390 B2 | 10/2012 | Levinson et al. |
| 8,333,700 B1 | 12/2012 | Barthe et al. |
| 8,337,539 B2 | 12/2012 | Ting et al. |
| 8,366,622 B2 | 2/2013 | Slayton et al. |
| 8,372,130 B2 | 2/2013 | Young et al. |
| 8,397,518 B1 | 3/2013 | Vistakula et al. |
| 8,414,631 B2 | 4/2013 | Quisenberry et al. |
| 8,433,400 B2 | 4/2013 | Prushinskaya et al. |
| 8,506,486 B2 | 8/2013 | Slayton et al. |
| 8,523,775 B2 | 9/2013 | Barthe et al. |
| 8,523,791 B2 | 9/2013 | Castel |
| 8,523,927 B2 | 9/2013 | Levinson et al. |
| 8,535,228 B2 | 9/2013 | Slayton et al. |
| 8,603,073 B2 | 12/2013 | Allison |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,676,332 B2 | 3/2014 | Fahey |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,702,774 B2 | 4/2014 | Baker et al. |
| 8,758,215 B2 | 6/2014 | Legendre et al. |
| 8,764,693 B1 | 7/2014 | Graham et al. |
| 8,834,547 B2 | 9/2014 | Anderson et al. |
| 9,861,421 B2 | 1/2018 | O'Neil et al. |
| 2001/0005791 A1 | 6/2001 | Ginsburg et al. |
| 2001/0007952 A1 | 7/2001 | Shimizu |
| 2001/0023364 A1 | 9/2001 | Ahn |
| 2001/0031459 A1 | 10/2001 | Fahy et al. |
| 2001/0039439 A1 | 11/2001 | Elkins et al. |
| 2001/0045104 A1 | 11/2001 | Bailey, Sr. et al. |
| 2001/0047196 A1 | 11/2001 | Ginsburg et al. |
| 2002/0026226 A1 | 2/2002 | Ein |
| 2002/0032473 A1 | 3/2002 | Kushnir et al. |
| 2002/0042607 A1 | 4/2002 | Palmer et al. |
| 2002/0049483 A1 | 4/2002 | Knowlton |
| 2002/0058975 A1 | 5/2002 | Bieberich |
| 2002/0062142 A1 | 5/2002 | Knowlton |
| 2002/0068338 A1 | 6/2002 | Nanda et al. |
| 2002/0082668 A1 | 6/2002 | Ingman |
| 2002/0103520 A1 | 8/2002 | Latham |
| 2002/0107558 A1 | 8/2002 | Clifton et al. |
| 2002/0117293 A1 | 8/2002 | Campbell |
| 2002/0120315 A1 | 8/2002 | Furuno et al. |
| 2002/0128648 A1 | 9/2002 | Weber et al. |
| 2002/0151830 A1 | 10/2002 | Kahn |
| 2002/0151887 A1 | 10/2002 | Stern et al. |
| 2002/0156509 A1 | 10/2002 | Cheung |
| 2002/0188286 A1 | 12/2002 | Quijano et al. |
| 2002/0198518 A1 | 12/2002 | Mikus et al. |
| 2003/0032900 A1 | 2/2003 | Ella |
| 2003/0044764 A1 | 3/2003 | Soane et al. |
| 2003/0055414 A1 | 3/2003 | Altshuler et al. |
| 2003/0062040 A1 | 4/2003 | Lurie et al. |
| 2003/0069618 A1 | 4/2003 | Smith, III et al. |
| 2003/0077326 A1 | 4/2003 | Newton et al. |
| 2003/0077329 A1 | 4/2003 | Kipp et al. |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0109911 A1 | 6/2003 | Lachenbruch et al. |
| 2003/0114885 A1 | 6/2003 | Nova et al. |
| 2003/0120268 A1 | 6/2003 | Bertolero et al. |
| 2003/0125649 A1 | 7/2003 | McIntosh et al. |
| 2003/0187488 A1 | 10/2003 | Kreindel et al. |
| 2003/0199226 A1 | 10/2003 | Sommer et al. |
| 2003/0199859 A1 | 10/2003 | Altshuler et al. |
| 2003/0220594 A1 | 11/2003 | Halvorson et al. |
| 2003/0220635 A1 | 11/2003 | Knowlton et al. |
| 2003/0220674 A1 | 11/2003 | Anderson et al. |
| 2003/0236487 A1 | 12/2003 | Knowlton |
| 2004/0002705 A1 | 1/2004 | Knowlton et al. |
| 2004/0006328 A1 | 1/2004 | Anderson |
| 2004/0009936 A1 | 1/2004 | Tang et al. |
| 2004/0024437 A1 | 2/2004 | Machold et al. |
| 2004/0030332 A1 | 2/2004 | Knowlton et al. |
| 2004/0034341 A1 | 2/2004 | Altshuler et al. |
| 2004/0039312 A1 | 2/2004 | Hillstead et al. |
| 2004/0044384 A1 | 3/2004 | Leber et al. |
| 2004/0049178 A1 | 3/2004 | Abboud et al. |
| 2004/0073079 A1 | 4/2004 | Altshuler et al. |
| 2004/0074629 A1 | 4/2004 | Noel |
| 2004/0077977 A1 | 4/2004 | Ella et al. |
| 2004/0082886 A1 | 4/2004 | Timpson |
| 2004/0093042 A1 | 5/2004 | Altshuler et al. |
| 2004/0104012 A1 | 6/2004 | Zhou et al. |
| 2004/0106867 A1 | 6/2004 | Eshel et al. |
| 2004/0133251 A1 | 7/2004 | Altshuler et al. |
| 2004/0162596 A1 | 8/2004 | Altshuler et al. |
| 2004/0176667 A1 | 9/2004 | Mihai et al. |
| 2004/0186535 A1 | 9/2004 | Knowlton |
| 2004/0199226 A1 | 10/2004 | Shadduck |
| 2004/0206365 A1 | 10/2004 | Knowlton |
| 2004/0210214 A1 | 10/2004 | Knowlton |
| 2004/0210287 A1 | 10/2004 | Greene |
| 2004/0215294 A1 | 10/2004 | Littrup et al. |
| 2004/0249427 A1 | 12/2004 | Nabilsi et al. |
| 2004/0259855 A1 | 12/2004 | Anderson et al. |
| 2004/0260209 A1 | 12/2004 | Ella et al. |
| 2004/0260210 A1 | 12/2004 | Ella et al. |
| 2004/0260211 A1 | 12/2004 | Maalouf |
| 2005/0010197 A1 | 1/2005 | Lau et al. |
| 2005/0033957 A1 | 2/2005 | Enokida |
| 2005/0049526 A1 | 3/2005 | Baer |
| 2005/0049543 A1 | 3/2005 | Anderson et al. |
| 2005/0049661 A1 | 3/2005 | Koffroth |
| 2005/0113725 A1 | 5/2005 | Masuda |
| 2005/0143781 A1 | 6/2005 | Carbunaru et al. |
| 2005/0145372 A1 | 7/2005 | Noel |

(56) References Cited

U.S. PATENT DOCUMENTS

| | | |
|---|---|---|
| 2005/0154314 A1 | 7/2005 | Quistgaard |
| 2005/0154431 A1 | 7/2005 | Quistgaard et al. |
| 2005/0159986 A1 | 7/2005 | Breeland et al. |
| 2005/0177075 A1 | 8/2005 | Meunier et al. |
| 2005/0182462 A1 | 8/2005 | Chornenky et al. |
| 2005/0187495 A1 | 8/2005 | Quistgaard et al. |
| 2005/0187597 A1 | 8/2005 | Vanderschuit |
| 2005/0203446 A1 | 9/2005 | Takashima |
| 2005/0215987 A1 | 9/2005 | Slatkine |
| 2005/0222565 A1 | 10/2005 | Manstein |
| 2005/0251117 A1 | 11/2005 | Anderson et al. |
| 2005/0251120 A1 | 11/2005 | Anderson et al. |
| 2005/0261753 A1 | 11/2005 | Littrup et al. |
| 2005/0277859 A1 | 12/2005 | Carlsmith et al. |
| 2005/0283144 A1 | 12/2005 | Shiono et al. |
| 2006/0030778 A1 | 2/2006 | Mendlein et al. |
| 2006/0035380 A1 | 2/2006 | Saint-Leger |
| 2006/0036300 A1 | 2/2006 | Kreindel |
| 2006/0041704 A1 | 2/2006 | Choi |
| 2006/0074313 A1 | 4/2006 | Slayton et al. |
| 2006/0079852 A1 | 4/2006 | Bubb et al. |
| 2006/0094988 A1 | 5/2006 | Tosaya et al. |
| 2006/0106836 A1 | 5/2006 | Masugi et al. |
| 2006/0122509 A1 | 6/2006 | Desilets |
| 2006/0189964 A1 | 8/2006 | Anderson et al. |
| 2006/0195168 A1 | 8/2006 | Dunbar et al. |
| 2006/0200063 A1 | 9/2006 | Munro et al. |
| 2006/0206040 A1 | 9/2006 | Greenberg et al. |
| 2006/0206110 A1 | 9/2006 | Knowlton et al. |
| 2006/0234899 A1 | 10/2006 | Nekmard et al. |
| 2006/0235121 A1 | 10/2006 | Burch |
| 2006/0259102 A1 | 11/2006 | Slatkine |
| 2006/0265032 A1 | 11/2006 | Hennings et al. |
| 2006/0270745 A1 | 11/2006 | Hunt et al. |
| 2006/0293734 A1 | 12/2006 | Scott et al. |
| 2007/0010811 A1 | 1/2007 | Stern et al. |
| 2007/0010861 A1 | 1/2007 | Anderson et al. |
| 2007/0032561 A1 | 2/2007 | Lin et al. |
| 2007/0038156 A1 | 2/2007 | Rosenberg |
| 2007/0055156 A1 | 3/2007 | Desilets et al. |
| 2007/0055173 A1 | 3/2007 | DeLonzor et al. |
| 2007/0055179 A1 | 3/2007 | Deem et al. |
| 2007/0055180 A1 | 3/2007 | Deem et al. |
| 2007/0055181 A1 | 3/2007 | Deem et al. |
| 2007/0073367 A1 | 3/2007 | Jones et al. |
| 2007/0078502 A1 | 4/2007 | Weber et al. |
| 2007/0100398 A1 | 5/2007 | Sloan |
| 2007/0106342 A1 | 5/2007 | Schumann |
| 2007/0129714 A1 | 6/2007 | Elkins et al. |
| 2007/0135876 A1 | 6/2007 | Weber |
| 2007/0141265 A1 | 6/2007 | Thomson |
| 2007/0179482 A1 | 8/2007 | Anderson et al. |
| 2007/0198071 A1 | 8/2007 | Ting et al. |
| 2007/0219540 A1 | 9/2007 | Masotti et al. |
| 2007/0239075 A1 | 10/2007 | Rosenberg et al. |
| 2007/0239150 A1 | 10/2007 | Zvuloni et al. |
| 2007/0249519 A1 | 10/2007 | Guha et al. |
| 2007/0255187 A1 | 11/2007 | Branch |
| 2007/0255274 A1 | 11/2007 | Stern et al. |
| 2007/0255362 A1* | 11/2007 | Levinson .................. A61F 7/10 607/96 |
| 2007/0265585 A1 | 11/2007 | Joshi et al. |
| 2007/0265614 A1 | 11/2007 | Stern et al. |
| 2007/0270925 A1 | 11/2007 | Levinson |
| 2007/0282249 A1 | 12/2007 | Quisenberry et al. |
| 2007/0282318 A1 | 12/2007 | Spooner et al. |
| 2008/0014627 A1 | 1/2008 | Merchant et al. |
| 2008/0046047 A1 | 2/2008 | Jacobs |
| 2008/0058784 A1 | 3/2008 | Manstein et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0097207 A1 | 4/2008 | Cai et al. |
| 2008/0139901 A1 | 6/2008 | Altshuler et al. |
| 2008/0140061 A1 | 6/2008 | Toubia et al. |
| 2008/0140371 A1 | 6/2008 | Warner |
| 2008/0161892 A1 | 7/2008 | Mercuro et al. |
| 2008/0183164 A1 | 7/2008 | Elkins et al. |
| 2008/0188915 A1 | 8/2008 | Mills et al. |
| 2008/0248554 A1 | 10/2008 | Merchant et al. |
| 2008/0269851 A1 | 10/2008 | Deem et al. |
| 2008/0287839 A1 | 11/2008 | Rosen et al. |
| 2008/0312651 A1 | 12/2008 | Pope et al. |
| 2009/0012434 A1 | 1/2009 | Anderson |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0024023 A1 | 1/2009 | Welches et al. |
| 2009/0076488 A1 | 3/2009 | Welches et al. |
| 2009/0112134 A1 | 4/2009 | Avni |
| 2009/0118722 A1 | 5/2009 | Ebbers et al. |
| 2009/0149929 A1 | 6/2009 | Levinson et al. |
| 2009/0149930 A1 | 6/2009 | Schenck |
| 2009/0171253 A1 | 7/2009 | Davenport |
| 2009/0171334 A1 | 7/2009 | Elkins et al. |
| 2009/0221938 A1 | 9/2009 | Rosenberg et al. |
| 2009/0276018 A1 | 11/2009 | Brader |
| 2009/0281464 A1 | 11/2009 | Cioanta et al. |
| 2009/0299234 A1 | 12/2009 | Cho et al. |
| 2009/0306749 A1 | 12/2009 | Mulindwa |
| 2009/0312676 A1 | 12/2009 | Rousso et al. |
| 2009/0312693 A1 | 12/2009 | Thapliyal et al. |
| 2009/0326621 A1 | 12/2009 | El-Galley |
| 2010/0015190 A1 | 1/2010 | Hassler |
| 2010/0028969 A1 | 2/2010 | Mueller et al. |
| 2010/0030306 A1 | 2/2010 | Edelman et al. |
| 2010/0036295 A1 | 2/2010 | Altshuler et al. |
| 2010/0042087 A1 | 2/2010 | Goldboss et al. |
| 2010/0049178 A1 | 2/2010 | Deem et al. |
| 2010/0081971 A1 | 4/2010 | Allison |
| 2010/0087806 A1 | 4/2010 | Da Silva et al. |
| 2010/0152824 A1 | 6/2010 | Allison |
| 2010/0168726 A1 | 7/2010 | Brookman |
| 2010/0179531 A1 | 7/2010 | Nebrigic et al. |
| 2010/0198064 A1 | 8/2010 | Perl et al. |
| 2010/0217349 A1 | 8/2010 | Fahey et al. |
| 2010/0268220 A1 | 10/2010 | Johnson et al. |
| 2010/0280582 A1* | 11/2010 | Baker .................. A61F 7/007 607/113 |
| 2011/0009860 A1 | 1/2011 | Chornenky et al. |
| 2011/0040235 A1 | 2/2011 | Castel |
| 2011/0040299 A1 | 2/2011 | Kim et al. |
| 2011/0046523 A1 | 2/2011 | Altshuler et al. |
| 2011/0060323 A1 | 3/2011 | Baust et al. |
| 2011/0066083 A1 | 3/2011 | Tosaya et al. |
| 2011/0066216 A1 | 3/2011 | Ting et al. |
| 2011/0077557 A1 | 3/2011 | Wing et al. |
| 2011/0077723 A1 | 3/2011 | Parish et al. |
| 2011/0112405 A1 | 5/2011 | Barthe et al. |
| 2011/0112520 A1 | 5/2011 | Kreindel |
| 2011/0144631 A1 | 6/2011 | Elkins et al. |
| 2011/0152849 A1 | 6/2011 | Baust et al. |
| 2011/0172651 A1 | 7/2011 | Altshuler et al. |
| 2011/0189129 A1 | 8/2011 | Qiu et al. |
| 2011/0196395 A1 | 8/2011 | Maschke |
| 2011/0196438 A1 | 8/2011 | Mnozil et al. |
| 2011/0202048 A1 | 8/2011 | Nebrigic et al. |
| 2011/0238050 A1 | 9/2011 | Allison et al. |
| 2011/0238051 A1 | 9/2011 | Levinson et al. |
| 2011/0257642 A1 | 10/2011 | Griggs, III |
| 2011/0300079 A1 | 12/2011 | Martens et al. |
| 2011/0301585 A1 | 12/2011 | Goulko |
| 2011/0313411 A1 | 12/2011 | Anderson et al. |
| 2011/0313412 A1 | 12/2011 | Kim et al. |
| 2012/0010609 A1 | 1/2012 | Deem et al. |
| 2012/0016239 A1 | 1/2012 | Barthe et al. |
| 2012/0022518 A1 | 1/2012 | Levinson |
| 2012/0022622 A1 | 1/2012 | Johnson et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |

(56) References Cited

U.S. PATENT DOCUMENTS

| | | |
|---|---|---|
| 2012/0065629 A1 | 3/2012 | Elkins et al. |
| 2012/0083862 A1 | 4/2012 | Altshuler et al. |
| 2012/0101549 A1 | 4/2012 | Schumann |
| 2012/0109041 A1 | 5/2012 | Munz |
| 2012/0158100 A1 | 6/2012 | Schomacker |
| 2012/0209363 A1 | 8/2012 | Williams, III et al. |
| 2012/0233736 A1 | 9/2012 | Tepper et al. |
| 2012/0239123 A1 | 9/2012 | Weber et al. |
| 2012/0253416 A1 | 10/2012 | Erez et al. |
| 2012/0259322 A1 | 10/2012 | Fourkas et al. |
| 2012/0277674 A1 | 11/2012 | Clark, III et al. |
| 2012/0310232 A1 | 12/2012 | Erez |
| 2013/0018236 A1 | 1/2013 | Altshuler et al. |
| 2013/0019374 A1 | 1/2013 | Schwartz |
| 2013/0066309 A1 | 3/2013 | Levinson |
| 2013/0073017 A1 | 3/2013 | Liu et al. |
| 2013/0079684 A1 | 3/2013 | Rosen et al. |
| 2013/0116758 A1 | 5/2013 | Levinson et al. |
| 2013/0116759 A1 | 5/2013 | Levinson et al. |
| 2013/0150844 A1 | 6/2013 | Deem et al. |
| 2013/0158440 A1 | 6/2013 | Allison |
| 2013/0158636 A1 | 6/2013 | Ting et al. |
| 2013/0166003 A1 | 6/2013 | Johnson et al. |
| 2013/0190744 A1 | 7/2013 | Avram et al. |
| 2013/0238062 A1 | 9/2013 | Ron Edoute et al. |
| 2013/0245507 A1 | 9/2013 | Khorassani Zadeh |
| 2013/0253384 A1 | 9/2013 | Anderson et al. |
| 2013/0253493 A1 | 9/2013 | Anderson et al. |
| 2013/0253494 A1 | 9/2013 | Anderson et al. |
| 2013/0253495 A1 | 9/2013 | Anderson et al. |
| 2013/0253496 A1 | 9/2013 | Anderson et al. |
| 2013/0303904 A1 | 11/2013 | Barthe et al. |
| 2013/0303905 A1 | 11/2013 | Barthe et al. |
| 2013/0331914 A1 | 12/2013 | Lee et al. |
| 2014/0005759 A1 | 1/2014 | Fahey et al. |
| 2014/0005760 A1 | 1/2014 | Levinson et al. |
| 2014/0067025 A1 | 3/2014 | Levinson et al. |
| 2014/0142469 A1 | 5/2014 | Britva et al. |
| 2014/0200487 A1 | 7/2014 | Ramdas et al. |
| 2014/0200488 A1 | 7/2014 | Seo et al. |
| 2014/0222121 A1 | 8/2014 | Spence et al. |
| 2014/0277219 A1 | 9/2014 | Nanda |
| 2014/0277302 A1 | 9/2014 | Weber et al. |
| 2014/0277303 A1 | 9/2014 | Biser et al. |
| 2014/0303697 A1 | 10/2014 | Anderson et al. |
| 2015/0216719 A1 | 8/2015 | DeBenedictis et al. |
| 2015/0216720 A1 | 8/2015 | DeBenedictis et al. |
| 2015/0216816 A1 | 8/2015 | O'Neil et al. |
| 2015/0223975 A1 | 8/2015 | Anderson et al. |
| 2015/0328077 A1 | 11/2015 | Levinson |
| 2015/0335468 A1 | 11/2015 | Rose et al. |
| 2015/0342780 A1 | 12/2015 | Levinson et al. |
| 2016/0051308 A1 | 2/2016 | Pennybacker et al. |
| 2016/0051401 A1 | 2/2016 | Yee et al. |
| 2016/0135985 A1 | 5/2016 | Anderson |
| 2016/0324684 A1 | 11/2016 | Levinson et al. |
| 2017/0079833 A1 | 3/2017 | Frangineas, Jr. et al. |
| 2017/0105869 A1 | 4/2017 | Frangineas, Jr. et al. |
| 2017/0165105 A1 | 6/2017 | Anderson et al. |
| 2017/0196731 A1 | 7/2017 | Debendictis et al. |
| 2017/0239079 A1 | 8/2017 | Root et al. |

FOREIGN PATENT DOCUMENTS

| | | |
|---|---|---|
| CA | 2585214 A1 | 10/2007 |
| CH | 333982 A | 11/1958 |
| CN | 86200604 U | 10/1987 |
| CN | 2514795 Y | 10/2002 |
| CN | 2514811 Y | 10/2002 |
| CN | 1511503 A | 7/2004 |
| CN | 1741777 A | 3/2006 |
| CN | 1817990 A | 8/2006 |
| CN | 2843367 Y | 12/2006 |
| CN | 2850584 Y | 12/2006 |
| CN | 2850585 Y | 12/2006 |
| CN | 200970265 Y | 11/2007 |
| CN | 101259329 A | 9/2008 |
| CN | 101309657 A | 11/2008 |
| DE | 532976 C | 9/1931 |
| DE | 2851602 A1 | 6/1980 |
| DE | 4213584 A1 | 11/1992 |
| DE | 4224595 A1 | 1/1994 |
| DE | 4238291 A1 | 5/1994 |
| DE | 4445627 A1 | 6/1996 |
| DE | 19800416 A1 | 7/1999 |
| EP | 263069 A2 | 4/1988 |
| EP | 0397043 A1 | 11/1990 |
| EP | 0406244 A1 | 1/1991 |
| EP | 0598824 A1 | 6/1994 |
| EP | 1030611 A1 | 8/2000 |
| EP | 1201266 A1 | 5/2002 |
| EP | 1568395 A1 | 8/2005 |
| EP | 2260801 A2 | 12/2010 |
| EP | 2289598 A1 | 3/2011 |
| EP | 2527005 A1 | 11/2012 |
| FR | 854937 A | 4/1940 |
| FR | 2744358 A1 | 8/1997 |
| FR | 2745935 A1 | 9/1997 |
| FR | 2767476 A1 | 2/1999 |
| FR | 2776920 A1 | 10/1999 |
| FR | 2789893 A1 | 8/2000 |
| FR | 2805989 A1 | 9/2001 |
| GB | 387960 A | 2/1933 |
| GB | 2120944 A | 12/1983 |
| GB | 2248183 A | 4/1992 |
| GB | 2263872 A | 8/1993 |
| GB | 2286660 A | 8/1995 |
| GB | 2323659 A | 9/1998 |
| JP | 58187454 A | 11/1983 |
| JP | 62082977 A | 4/1987 |
| JP | 63076895 A | 4/1988 |
| JP | 01223961 A | 9/1989 |
| JP | 03051964 A | 3/1991 |
| JP | 03259975 A | 11/1991 |
| JP | 04093597 A | 3/1992 |
| JP | 06261933 A | 9/1994 |
| JP | 07194666 A | 8/1995 |
| JP | 07268274 A | 10/1995 |
| JP | 09164163 A | 6/1997 |
| JP | 10216169 A | 8/1998 |
| JP | 10223961 A | 8/1998 |
| JP | 2000503154 A | 3/2000 |
| JP | 3065657 B2 | 7/2000 |
| JP | 2001046416 A | 2/2001 |
| JP | 2002125993 A | 5/2002 |
| JP | 2002224051 A | 8/2002 |
| JP | 2002282295 A | 10/2002 |
| JP | 2002290397 A | 10/2002 |
| JP | 2002543668 A | 12/2002 |
| JP | 2003190201 A | 7/2003 |
| JP | 2004013600 A | 1/2004 |
| JP | 2004073812 A | 3/2004 |
| JP | 2004159666 A | 6/2004 |
| JP | 2005039790 A | 2/2005 |
| JP | 2005065984 A | 3/2005 |
| JP | 2005110755 A | 4/2005 |
| JP | 2005509977 A | 4/2005 |
| JP | 3655820 B2 | 6/2005 |
| JP | 2005520608 A | 7/2005 |
| JP | 2005237908 A | 9/2005 |
| JP | 2005323716 A | 11/2005 |
| JP | 2006026001 A | 2/2006 |
| JP | 2006130055 A | 5/2006 |
| JP | 2006520949 A | 9/2006 |
| JP | 2007270459 A | 10/2007 |
| JP | 2008532591 A | 8/2008 |
| JP | 2009515232 A | 4/2009 |
| JP | 2009189757 A | 8/2009 |
| KR | 200173222 Y1 | 12/1999 |
| KR | 1020040094508 A | 11/2004 |
| KR | 20090000258 U | 1/2009 |
| KR | 1020130043299 A | 4/2013 |
| KR | 1020140038165 A | 3/2014 |
| RU | 2036667 C1 | 6/1995 |

(56) References Cited

FOREIGN PATENT DOCUMENTS

| | | |
|---|---|---|
| SU | 532976 A1 | 11/1978 |
| TW | 0476644 B | 2/2002 |
| WO | 8503216 A1 | 8/1985 |
| WO | 9114417 A1 | 10/1991 |
| WO | 9404116 A1 | 3/1994 |
| WO | 9623447 A1 | 8/1996 |
| WO | 9626693 A1 | 9/1996 |
| WO | 9636293 A1 | 11/1996 |
| WO | 9637158 A1 | 11/1996 |
| WO | 9704832 A1 | 2/1997 |
| WO | 9705828 A1 | 2/1997 |
| WO | 9722262 A2 | 6/1997 |
| WO | 9724088 A1 | 7/1997 |
| WO | 9725798 A1 | 7/1997 |
| WO | 9748440 A1 | 12/1997 |
| WO | 9829134 A2 | 7/1998 |
| WO | 9831321 A1 | 7/1998 |
| WO | 9841156 A1 | 9/1998 |
| WO | 9841157 A1 | 9/1998 |
| WO | 9909928 A1 | 3/1999 |
| WO | 9916502 A1 | 4/1999 |
| WO | 9938469 A1 | 8/1999 |
| WO | 9949937 A1 | 10/1999 |
| WO | 0044346 A1 | 8/2000 |
| WO | 0044349 A1 | 8/2000 |
| WO | 0065770 A1 | 11/2000 |
| WO | 0067685 A1 | 11/2000 |
| WO | 0100269 A1 | 1/2001 |
| WO | 0113989 A1 | 3/2001 |
| WO | 0114012 A1 | 3/2001 |
| WO | 0134048 A1 | 5/2001 |
| WO | 0205736 A1 | 1/2002 |
| WO | 02102921 A1 | 12/2002 |
| WO | 03007859 A1 | 1/2003 |
| WO | 03078596 A2 | 9/2003 |
| WO | 03079916 A1 | 10/2003 |
| WO | 2004000098 A2 | 12/2003 |
| WO | 2004080279 A2 | 9/2004 |
| WO | 2004090939 A2 | 10/2004 |
| WO | 2005033957 A1 | 4/2005 |
| WO | 2005046540 A1 | 5/2005 |
| WO | 2005060354 A2 | 7/2005 |
| WO | 2005062896 A2 | 7/2005 |
| WO | 2005096979 A1 | 10/2005 |
| WO | 2005112815 A1 | 12/2005 |
| WO | 2006066226 A1 | 6/2006 |
| WO | 2006094348 A1 | 9/2006 |
| WO | 2006106836 A1 | 10/2006 |
| WO | 2006116603 A2 | 11/2006 |
| WO | 2006127467 A2 | 11/2006 |
| WO | 2007012083 A2 | 1/2007 |
| WO | 2007028975 A1 | 3/2007 |
| WO | 2007041642 A2 | 4/2007 |
| WO | 2007101039 A1 | 9/2007 |
| WO | 2007127924 A2 | 11/2007 |
| WO | 2007145421 A1 | 12/2007 |
| WO | 2007145422 A1 | 12/2007 |
| WO | 2008006018 A2 | 1/2008 |
| WO | 2008039556 A1 | 4/2008 |
| WO | 2008039557 A1 | 4/2008 |
| WO | 2008055243 A2 | 5/2008 |
| WO | 2008143678 A1 | 11/2008 |
| WO | 2009011708 A1 | 1/2009 |
| WO | 2009026471 A1 | 2/2009 |
| WO | 2010077841 A1 | 7/2010 |
| WO | 2010127315 A2 | 11/2010 |
| WO | 2012012296 A1 | 1/2012 |
| WO | 2012103242 A1 | 8/2012 |
| WO | 2013013059 A1 | 1/2013 |
| WO | 2013075006 A1 | 5/2013 |
| WO | 2013075016 A1 | 5/2013 |
| WO | 2013190337 A1 | 12/2013 |
| WO | 2014151872 A3 | 9/2014 |
| WO | 2014191263 A1 | 12/2014 |
| WO | 2015088368 A1 | 6/2015 |
| WO | 2015117001 A1 | 8/2015 |
| WO | 2015117005 A1 | 8/2015 |
| WO | 2015117026 A2 | 8/2015 |
| WO | 2015117032 A1 | 8/2015 |
| WO | 2015117036 A2 | 8/2015 |
| WO | 2016028796 A1 | 2/2016 |
| WO | 2016048721 A1 | 3/2016 |

OTHER PUBLICATIONS

Aguilar et al., "Modeling Cryogenic Spray Temperature and Evaporation Rate Based on Single-Droplet Analysis," Eighth International Conference on Liquid Atomization and Spray Systems, Pasadena, CA, USA, Jul. 2000, 7 pages.

Al-Sakere, B. et al. "Tumor Ablation with Irreversible Electroporation," PLoS One, Issue 11, Nov. 2007, 8 pages.

Alster, T. et al., "Cellulite Treatment Using a Novel Combination Radiofrequency, Infrared Light, and Mechanical Tissue Manipulation Device," Journal of Cosmetic and Laser Therapy, vol. 7, 2005, pp. 81-85.

Ardevol, A. et al., "Cooling Rates of Tissue Samples During Freezing with Liquid Nitrogen," Journal of Biochemical and Biophysical Methods, vol. 27, 1993, pp. 77-86.

Arena, C. B. et al., "High-Frequency Irreversible Electroporation (H-FIRE) for Non-Thermal Ablation Without Muscle Contraction," BioMedical Engineering OnLine 2011, 10:102, Nov. 21, 2011, 21 pgs.

Becker, S. M. et al. "Local Temperature Rises Influence In Vivo Electroporation Pore Development: A Numerical Stratum Corneum Lipid Phase Transition Model," Journal of Biomechanical Engineering, vol. 129, Oct. 2007, pp. 712-721.

Bohm, T. et al., "Saline-Enhanced Radiofrequency Ablation of Breast Tissue: an in Vitro Feasibility Study," Investigative Radiology, vol. 35 (3), 2000, pp. 149-157.

Bondei, E. et al., "Disorders of Subcutaneous Tissue (Cold Panniculitis)," Dermatology in General Medicine, Fourth Edition, vol. 1, Chapter 108, 1993, Section 16, pp. 1333-1334.

Burge, S.M. et al., "Hair Follicle Destruction and Regeneration in Guinea Pig Skin after Cutaneous Freeze Injury," Cryobiology, 27(2), 1990, pp. 153-163.

Coban, Y. K. et al., "Ischemia-Reperfusion Injury of Adipofascial Tissue: An Experimental Study Evaluating Early Histologic and Biochemical Alterations in Rats," Mediators of Inflammation, 2005, 5, pp. 304-308.

Del Pino, M. E. et al. "Effect of Controlled Volumetric Tissue Heating with Radiofrequency on Cellulite and the Subcutaneous Tissue of the Buttocks and Thighs," Journal of Drugs in Dermatology, vol. 5, Issue 8, Sep. 2006, pp. 714-722.

Donski, P. K. et al., "The Effects of Cooling no Experimental Free Flap Survival," British Journal of Plastic Surgery, vol. 33, 1980, pp. 353-360.

Duck, F. A., Physical Properties of Tissue, Academic Press Ltd., chapters 4 & 5, 1990, pp. 73-165.

Duncan, W. C. et al., "Cold Panniculitis," Archives of Dermatology, vol. 94, Issue 6, Dec. 1966, pp. 722-724.

Epstein, E. H. et al., "Popsicle Panniculitis," The New England Journal of Medicine, 282(17), Apr. 23, 1970, pp. 966-967.

Fournier, L. et al. "Lattice Model for the Kinetics of Rupture of Fluid Bilayer Membranes," Physical Review, vol. 67, 2003, pp. 051908-1-051908-11.

Gabriel, S. et al., "The Dielectric Properties of Biological Tissues: II. Measurements in the Frequency Range 10 Hz to 20 GHz," Physics in Medicine and Biology, vol. 41, 1996, pp. 2251-2269.

Gage, A. "Current Progress in Cryosurgery," Cryobiology 25, 1988, pp. 483-486.

Gatto, H. "Effects of Thermal Shocks on Interleukin-1 Levels and Heat Shock Protein 72 (HSP72) Expression in Normal Human Keratinocytes," PubMed, Archives of Dermatological Research, vol. 284, Issue 7, 1992: pp. 414-417 [Abstract].

Hale, H. B. et al., "Influence of Chronic Heat Exposure and Prolonged Food Deprivation on Excretion of Magnesium, Phos-

(56) References Cited

OTHER PUBLICATIONS phorus, Calcium, Hydrogen Ion & Ketones," Aerospace Medicine, vol. 39—No. 9, Sep. 1968, pp. 919-926.
Heller Page, E. et al., "Temperature-dependent skin disorders," Journal of the American Academy of Dermatology, vol. 18, No. 5, Pt 1, May 1988, pp. 1003-1019.
Hemmingsson, A. et al. "Attenuation in Human Muscle and Fat Tissue in Vivo and in Vitro," Acra Radiologica Diagnosis, vol. 23, No. 2, 1982, pp. 149-151.
Henry, F. et al., "Les Dermatoses Hivernales," Rev Med Liege, 54:11, 1999, pp. 864-866. [Abstract Attached].
Hernan, P. et al., "Study for the evaluation of the efficacy of Lipocryolysis (EEEL)", Nov. 30, 2011.
Hernan, R. P., "A Study to Evaluate the Action of Lipocryolysis", 33(3) CryoLellers, 2012, pp. 176-180.
Holland, DB. et al. "Cold shock induces the synthesis of stress proteins in human keratinocytes," PubMed Journal of Investigative Dermatology; 101(2): Aug. 1993, pp. 196-199.
Holman, W. L. et al., "Variation in Cryolesion Penetration Due to Probe Size and Tissue Thermal Conductivity," The Annals of Thoracic Surgery, vol. 53, 1992, pp. 123-126.
Hong, J.S. et al., "Patterns of Ice Formation in Normal and Malignant Breast Tissue," Cryobiology 31, 1994, pp. 109-120.
Huang et al. "Comparative Proteomic Profiling of Murine Skin," Journal of Investigative Dermatology, vol. 121(1), Jul. 2003, pp. 51-64.
International Search Report and Written Opinion for PCT/US2015/013912; Applicant: Zeltiq Aesthetics, Inc.; dated May 6, 2015, 13 pages.
Isambert, H. "Understanding the Electroporation of Cells and Artificial Bilayer Membranes," Physical Review Letters, vol. 80, No. 15, 1998, pp. 3404-3707.
Jalian, H. R. et al., "Cryolipolysis: A Historical Perspective and Current Clinical Practice", 32(1) Semin. Cutan. Med. Surg., 2013, pp. 31-34.
Kellum, R. E. et al., "Sclerema Neonatorum: Report of Case and Analysis of Subcutaneous and Epidermal-Dermal Lipids by Chromatographic Methods," Archives of Dermatology, vol. 97, Apr. 1968, pp. 372-380.
Koska, J. et al., "Endocrine Regulation of Subcutaneous Fat Metabolism During Cold Exposure in Humans," Annals of the New York Academy of Sciences, vol. 967, 2002,pp. 500-505.
Kundu, S. K. et al., "Breath Acetone Analyzer: Diagnostic Tool to Monitor Dietary Fat Loss," Clinical Chemistry, vol. 39, Issue (1), 1993, pp. 87-92.
Kundu, S. K. et al., "Novel Solid-Phase Assay of Ketone Bodies in Urine," Clinical Chemistry, vol. 37, Issue (9), 1991, pp. 1565-1569.
Kuroda, S. et al. "Thermal Distribution of Radio-Frequency Inductive Hyperthermia Using an Inductive Aperture-Type Applicator: Evaluation of the Effect of Tumor Size and Depth", Medical and Biological Engineering and Computing, vol. 37, 1999, pp. 285-290.
Laugier, P. et al., "In Vivo Results with a New Device for Ultrasonic Monitoring of Pig Skin Cryosurgery: The Echographic Cryprobe," The Society for Investigative Dermatology, Inc., vol. 111, No. 2, Aug. 1998, pp. 314-319.
Levchenko et al., "Effect of Dehydration on Lipid Metabolism" Ukrainskii Biokhimicheskii Zhurnal, vol. 50, Issue 1, 1978, pp. 95-97.
Lidagoster, MD et al., "Comparison of Autologous Fat Transfer in Fresh, Refrigerated, and Frozen Specimens: An Animal Model," Annals of Plastic Surgery, vol. 44, No. 5, May 2000, pp. 512-515.
Liu, A. Y.-C. et al., "Transient Cold Shock Induces the Heat Shock Response upon Recovery at 37 C in Human Cells," Journal of Biological Chemistry 269(20), May 20, 1994, pp. 14768-14775.
L'Vova, S.P. "Lipid Levels and Lipid Peroxidation in Frog Tissues During Hypothermia and Hibernation" Ukrainskii Biokhimicheskii Zhurnal, vol. 62, Issue 1, 1990, pp. 65-70.
Maize, J.C. "Panniculitis," Cutaneous Pathology, Chapter 13, 1998, 327-344.

Malcolm, G. T. et al., "Fatty Acid Composition of Adipose Tissue in Humans: Differences between Subcutaneous Sites," The American Journal of Clinical Nutrition, vol. 50, 1989, pp. 288-291.
Manstein, D. et al. "A Novel Cryotherapy Method of Non-invasive, Selective Lipolysis," LasersSurg.Med 40:S20, 2008, p. 104.
Manstein, D. et al. "Selective Cryolysis: A Novel Method of Non-Invasive Fat Removal," Lasers in Surgery and Medicine: The Official Journal of the ASLMS, vol. 40, 2008, pp. 595-604.
Mayoral, "Case Reports: Skin Tightening with a Combined Unipolar and Bipolar Radiofrequency Device," Journal of Drugs in Dermatology, 2007, pp. 212-215.
Mazur, P. "Cryobiology: the Freezing of Biological Systems," Science, 68, 1970, pp. 939-949.
Merrill, T. "A Chill to the Heart: A System to Deliver Local Hypothermia Could One Day Improve the Lives of Heart-Attack Patients," Mechanical Engineering Magazine, Oct. 2010, 10 pages.
Miklavcic, D. et al. "Electroporation-Based Technologies and Treatments," The Journal of Membrane Biology (2010) 236:1-2, 2 pgs.
Moschella, S. L. et al., "Diseases of the Subcutaneous Tissue," in Dermatology, Second Edition, vol. 2, 1985 Chapter 19, Section II (W.B. Saunders Company, 1980) pp. 1169-1181.
Murphy, J. V. et al., "Frostbite: Pathogenesis and Treatment" The Journal of Trauma: Injury, Infection, and Critical Care, vol. 48, No. 1, Jan. 2000, pp. 171-178.
Nagao, T. et al., "Dietary Diacylglycerol Suppresses Accumulation of Body Fat Compared to Triacylglycerol in Men a Double-Blind Controlled Trial," The Journal of Nutrition, vol. 130, Issue (4), 2000, pp. 792-797.
Nagle, W. A. et al. "Cultured Chinese Hamster Cells Undergo Apoptosis After Exposure to Cold but Nonfreezing Temperatures," Cryobiology 27, 1990, pp. 439-451.
Nagore, E. et al., "Lipoatrophia Semicircularis-a Traumatic Panniculitis: Report of Seven Cases and Review of the Literature," Journal of the American Academy of Dermatology, vol. 39, Nov. 1998, pp. 879-881.
Nanda, G.S. et al., "Studies on electroporation of thermally and chemically treated human erythrocytes," Bioelectrochemistry and Bioenergetics, 34, 1994, pp. 129-134, 6 pgs.
Narins, D.J. et al. "Non-Surgical Radiofrequency Facelift", The Journal of Drugs in Dermatology, vol. 2, Issue 5, 2003, pp. 495-500.
Nielsen, B. "Thermoregulation in Rest and Exercise," Acta Physiologica Scandinavica Supplementum, vol. 323 (Copenhagen 1969), pp. 7-74.
Nishikawa, H. et al. "Ultrastructural Changes and Lipid Peroxidation in Rat Adipomusculocutaneous Flap Isotransplants after Normothermic Storage and Reperfusion," Transplantation, vol. 54, No. 5,1992, pp. 795-801.
Nurnberger, F. "So-Called Cellulite: An Invented Disease," Journal of Dermatologic Surgery and Oncology, Mar. 1978, pp. 221-229.
Pease, G. R. et al., "An Integrated Probe for Magnetic Resonance Imaging Monitored Skin Cryosurgery," Journal of Biomedical Engineering, vol. 117, Feb. 1995, pp. 59-63.
Pech, P. et al., "Attenuation Values, Volume Changes and Artifacts in Tissue Due to Freezing," Acta Radiologica ,vol. 28, Issue 6, 1987, pp. 779-782.
Peterson, L. J. et al., "Bilateral Fat Necrosis of the Scrotum," Journal of Urology, vol. 116, 1976, pp. 825-826.
Phinney, S. D. et al., "Human Subcutaneous Adipose Tissue Shows Site-Specific Differences in Fatty Acid Composition," The American Journal of Clinical Nutrition, vol. 60, 1994, pp. 725-729.
Pierard, G.E. et al., "Cellulite: From Standing Fat Herniation to Hypodermal Stretch Marks," The American Journal of Dermatology, vol. 22, Issue 1, 2000, pp. 34-37, [Abstract].
Pope, K. et al. "Selective Fibrous Septae Heating: An Additional Mechanism of Action for Capacitively Coupled Monopolar Radiofrequency" Thermage, Inc. Article, Feb. 2005, 6pgs.
Quinn, P. J. "A Lipid-Phase Separation Model of Low-Temperature Damage to Biological Membranes," Cryobiology, 22, 1985, 128-146.
Rabi, T. et al., "Metabolic Adaptations in Brown Adipose Tissue of the Hamster in Extreme Ambient Temperatures," American Journal of Physiology, vol. 231, Issue 1, Jul. 1976, pp. 153-160.

(56) References Cited

OTHER PUBLICATIONS

Renold, A.E. et al. "Adipose Tissue" in Handbook of Physiology, Chapter 15, (Washington, D.C., 1965) pp. 169-176.
Rossi, A. B. R. et al. "Cellulite: a Review," European Academy of Dermatology and Venercology, 2000, pp. 251-262, 12 pgs.
Rubinsky, B. "Principles of Low Temperature Cell Preservation," Heart Failure Reviews, vol. 8, 2003, pp. 277-284.
Rubinsky, B. et al., "Cryosurgery: Advances in the Application of low Temperatures to Medicine," International Journal of Refrigeration, vol. 14, Jul. 1991, pp. 190-199.
Saleh, K.Y. et al., "Two-Dimensional Ultrasound Phased Array Design for Tissue Ablation for Treatment of Benign Prostatic Hyperplasia," International Journal of Hyperthermia, vol. 20, No. 1, Feb. 2004, pp. 7-31.
Schoning, P. et al., "Experimental Frostbite: Freezing Times, Rewarming Times, and Lowest Temperatures of Pig Skin Exposed to Chilled Air," Cryobiology 27, 1990, pp. 189-193.
Shephard, R. J. "Adaptation to Exercise in the Cold," Sports Medicine, vol. 2, 1985, pp. 59-71.
Sigma-Aldrich "Poly(ethylene glycol) and Poly(ethylene oxide)," http://www.sigmaaldrich.com/materials-science/materialscience-;products.htmi?TablePage=2020411 0, accessed Oct. 19, 2012.
Smalls, L. K. et al. "Quantitative Model of Cellulite: Three Dimensional Skin Surface Topography, Biophysical Characterization, and Relationship to Human Perception," International Journal of Cosmetic Science, vol. 27, Issue 5, Oct. 2005, 17 pgs.
Thermage, News Release, "Study Published in Facial Plastic Surgery Journal Finds Selective Heating of Fibrous Septae Key to Success and Safety of Thermage ThermaCool System," Jun. 20, 2005, 2 pages.
Vallerand et al. "Cold Stress Increases Lipolysis, FFA Ra and TG/FFA Cycling in Humans," Aviation, Space, and Environmental Medicine 70(1), 1999, pp. 42-50.
Wang, X. et al., "Cryopreservation of Cell/Hydrogel Constructs Based on a new Cell-Assembling Technique," Sep. 5, 2009, 40 pages.
Wharton, D. A. et al., "Cold Acclimation and Cryoprotectants in a Freeze-Tolerant Antarctic Nematode, Panagrolaimus Davidi,", Journal of Comparative Physiology, vol. 170, No. 4, Mar. 2000, 2 pages.
Winkler, C. et al., "Gene Transfer in Laboratory Fish: Model Organisms for the Analysis of Gene Function," in Transgenic Animals, Generation and Use (The Netherlands 1997), pp. 387-395.
Young, H. E. et al. "Isolation of Embryonic Chick Myosatellite and Pluripotent Stem Cells" The Journal of Tissue Culture Methods, vol. 14, Issue 2, 1992, pp. 85-92.
Zelickson, B. et al., "Cryolipolysis for Noninvasive Fat Cell Destruction: Initial Results from a Pig Model", 35 Dermatol. Sug., 2009, pp. 1-9.
Zouboulis, C. C. et al., "Current Developments and Uses of Cryosurgery in the Treatment of Keloids and Hypertrophic Scars," Wound Repair and Regeneration, vol. 10, No. 2, 2002, pp. 98-102.
International Search Report and Written Opinion of counterpart International Application No. PCT/US2017/012626; dated Mar. 30, 2017: 17 pages.

\* cited by examiner

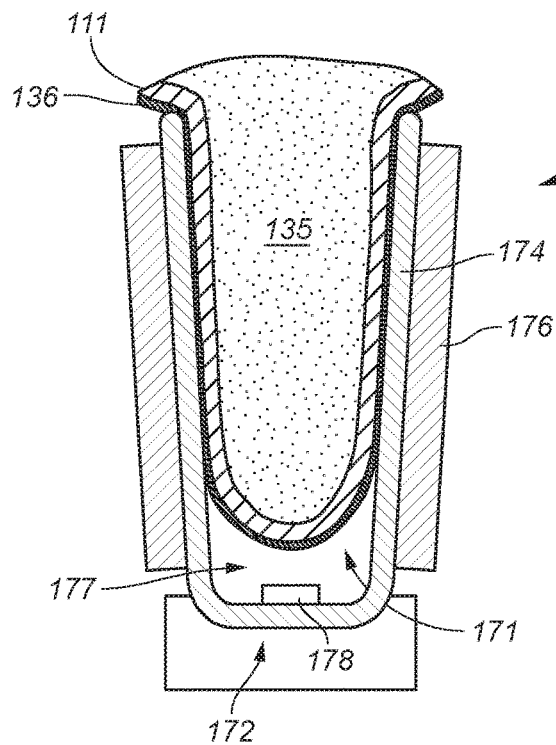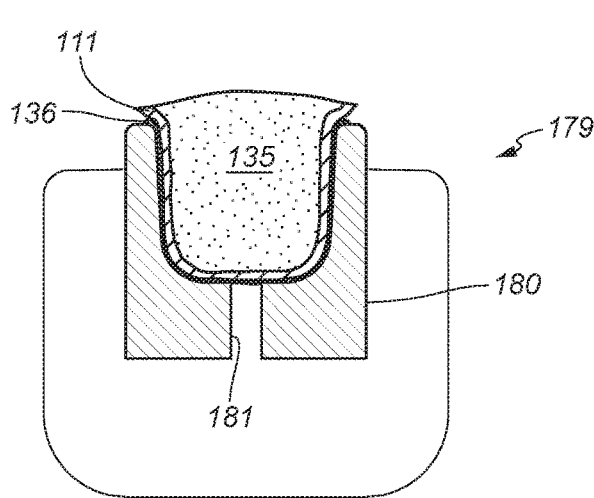
Fig. 12    Fig. 13
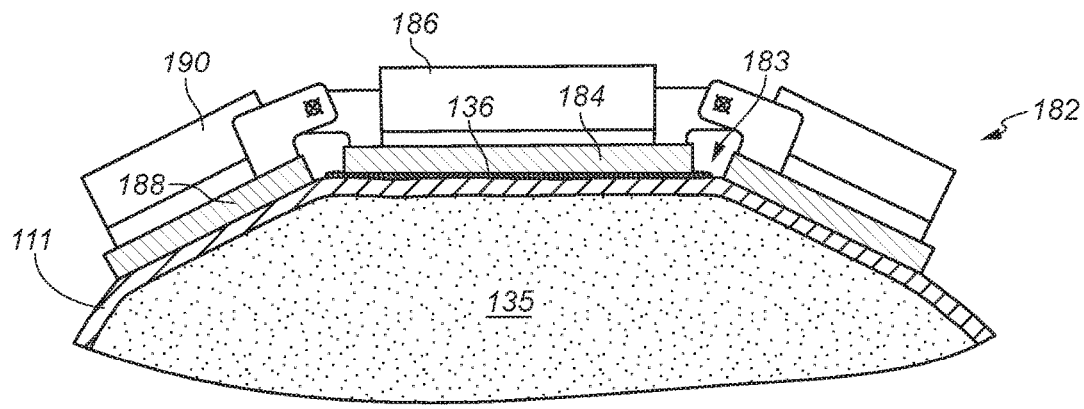
Fig. 14

TEMPERATURE-DEPENDENT ADHESION BETWEEN APPLICATOR AND SKIN DURING COOLING OF TISSUE

CROSS-REFERENCE TO RELATED APPLICATION

The present application claims the benefit of the earlier filing date of U.S. Provisional Patent Application No. 62/276,131, filed Jan. 7, 2016, which is incorporated herein by reference in its entirety.

TECHNICAL FIELD

The present disclosure is related to cooling of tissue, such as in the context of cryolipolysis and cryolysis.

INCORPORATION BY REFERENCE

The following commonly assigned U.S. patent applications and U.S. patents are incorporated herein by reference in their entireties:

U.S. Patent Publication No. 2008/0287839 entitled "METHOD OF ENHANCED REMOVAL OF HEAT FROM SUBCUTANEOUS LIPID-RICH CELLS AND TREATMENT APPARATUS HAVING AN ACTUATOR";

U.S. Pat. No. 6,032,675 entitled "FREEZING METHOD FOR CONTROLLED REMOVAL OF FATTY TISSUE BY LIPOSUCTION";

U.S. Patent Publication No. 2007/0255362 entitled "CRYOPROTECTANT FOR USE WITH A TREATMENT DEVICE FOR IMPROVED COOLING OF SUBCUTANEOUS LIPID-RICH CELLS";

U.S. Pat. No. 7,854,754 entitled "COOLING DEVICE FOR REMOVING HEAT FROM SUBCUTANEOUS LIPID-RICH CELLS";

U.S. Patent Publication No. 2011/0066216 entitled "COOLING DEVICE FOR REMOVING HEAT FROM SUBCUTANEOUS LIPID-RICH CELLS";

U.S. Patent Publication No. 2008/0077201 entitled "COOLING DEVICES WITH FLEXIBLE SENSORS";

U.S. Patent Publication No. 2008/0077211 entitled "COOLING DEVICE HAVING A PLURALITY OF CONTROLLABLE COOLING ELEMENTS TO PROVIDE A PREDETERMINED COOLING PROFILE";

U.S. Patent Publication No. 2009/0118722, filed Oct. 31, 2007, entitled "METHOD AND APPARATUS FOR COOLING SUBCUTANEOUS LIPID-RICH CELLS OR TISSUE";

U.S. Patent Publication No. 2009/0018624 entitled "LIMITING USE OF DISPOSABLE SYSTEM PATIENT PROTECTION DEVICES";

U.S. Patent Publication No. 2009/0018623 entitled "SYSTEM FOR TREATING LIPID-RICH REGIONS";

U.S. Patent Publication No. 2009/0018625 entitled "MANAGING SYSTEM TEMPERATURE TO REMOVE HEAT FROM LIPID-RICH REGIONS";

U.S. Patent Publication No. 2009/0018627 entitled "SECURE SYSTEM FOR REMOVING HEAT FROM LIPID-RICH REGIONS";

U.S. Patent Publication No. 2009/0018626 entitled "USER INTERFACES FOR A SYSTEM THAT REMOVES HEAT FROM LIPID-RICH REGIONS";

U.S. Pat. No. 6,041,787 entitled "USE OF CRYOPROTECTIVE AGENT COMPOUNDS DURING CRYOSURGERY";

U.S. Pat. No. 8,285,390 entitled "MONITORING THE COOLING OF SUBCUTANEOUS LIPID-RICH CELLS, SUCH AS THE COOLING OF ADIPOSE TISSUE";

U.S. Pat. No. 8,275,442 entitled "TREATMENT PLANNING SYSTEMS AND METHODS FOR BODY CONTOURING APPLICATIONS";

U.S. patent application Ser. No. 12/275,002 entitled "APPARATUS WITH HYDROPHILIC RESERVOIRS FOR COOLING SUBCUTANEOUS LIPID-RICH CELLS";

U.S. patent application Ser. No. 12/275,014 entitled "APPARATUS WITH HYDROPHOBIC FILTERS FOR REMOVING HEAT FROM SUBCUTANEOUS LIPID-RICH CELLS";

U.S. Patent Publication No. 2010/0152824 entitled "SYSTEMS AND METHODS WITH INTERRUPT/RESUME CAPABILITIES FOR COOLING SUBCUTANEOUS LIPID-RICH CELLS";

U.S. Pat. No. 8,192,474 entitled "TISSUE TREATMENT METHODS";

U.S. Patent Publication No. 2010/0280582 entitled "DEVICE, SYSTEM AND METHOD FOR REMOVING HEAT FROM SUBCUTANEOUS LIPID-RICH CELLS";

U.S. Patent Publication No. 2012/0022518 entitled "COMBINED MODALITY TREATMENT SYSTEMS, METHODS AND APPARATUS FOR BODY CONTOURING APPLICATIONS";

U.S. Publication No. 2011/0238050 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS";

U.S. Publication No. 2011/0238051 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS";

U.S. Publication No. 2012/0239123 entitled "DEVICES, APPLICATION SYSTEMS AND METHODS WITH LOCALIZED HEAT FLUX ZONES FOR REMOVING HEAT FROM SUBCUTANEOUS LIPID-RICH CELLS";

U.S. patent application Ser. No. 13/830,413 entitled "MULTI-MODALITY TREATMENT SYSTEMS, METHODS AND APPARATUS FOR ALTERING SUBCUTANEOUS LIPID-RICH TISSUE";

U.S. patent application Ser. No. 13/830,027 entitled "TREATMENT SYSTEMS WITH FLUID MIXING SYSTEMS AND FLUID-COOLED APPLICATORS AND METHODS OF USING THE SAME";

U.S. patent application Ser. No. 11/528,225 entitled "COOLING DEVICE HAVING A PLURALITY OF CONTROLLABLE COOLING ELEMENTS TO PROVIDE A PREDETERMINED COOLING PROFILE;" and U.S. Pat. No. 8,285,390 entitled "MONITORING THE COOLING OF SUBCUTANEOUS LIPID-RICH CELLS, SUCH AS THE COOLING OF ADIPOSE TISSUE."

To the extent the foregoing commonly assigned U.S. patent applications and U.S. patents or any other material incorporated herein by reference conflicts with the present disclosure, the present disclosure controls.

BACKGROUND

Excess body fat, or adipose tissue, may be present at various locations of a subject's body and may detract from personal appearance. Excess subcutaneous fat under the chin and/or around the neck can be cosmetically unappealing and, in some instances, can produce a "double chin." A double chin can cause stretching and/or sagging of skin and may also result in discomfort. Moreover, excess adipose tissue in superficial fat compartments can produce loose facial structures, such as loose jowls, that also cause an undesirable appearance. Excess body fat can also be located at the abdomen, thighs, buttocks, knees, and arms, as well as other locations.

Aesthetic improvement of the human body may involve the selective removal of adipose tissue. Invasive procedures (e.g., liposuction) for this purpose, however, tend to be associated with relative high costs, long recovery times, and increased risk of complications. Injection of drugs for reducing adipose tissue, such as submental or facial adipose tissue, can cause significant swelling, bruising, pain, numbness, and/or induration. Conventional non-invasive treatments for reducing adipose tissue may include regular exercise, application of topical agents, use of weight-loss drugs, dieting, or a combination of these treatments. One drawback of these non-invasive treatments is that they may not be effective or even possible under certain circumstances. For example, when a person is physically injured or ill, regular exercise may not be an option. Topical agents and orally administered weight-loss drugs are not an option if, as another example, they cause an undesirable reaction (e.g., an allergic or other negative reaction). Additionally, non-invasive treatments may be ineffective for selectively reducing specific regions of adiposity. For example, localized fat loss around the neck, jaw, cheeks, etc. often cannot be achieved using general or systemic weight-loss methods.

Furthermore, aesthetic and/or therapeutic improvement of the human body may involve treatment or alteration of non-lipid rich tissue as well as lipid rich tissue, and again conventional treatments sometimes are not suitable for many subjects and cannot effectively target certain regions of tissue necessary for an effective treatment. For at least the foregoing reasons, there is a need for innovation in this field of aesthetic and/or therapeutic improvement of the human body.

BRIEF DESCRIPTION OF THE DRAWINGS

Many aspects of the present invention can be better understood with reference to the following drawings. The components in the drawings are not necessarily to scale. Instead, emphasis is placed on illustrating clearly the principles of the present invention. For ease of reference, throughout this disclosure identical reference numbers may be used to identify identical, similar, or analogous components or features of more than one embodiment of the present invention.

FIGS. 12-14 are cross-sectional views similar to FIG. 6 showing areas around treatment interfaces during cooling treatments in accordance with still other respective embodiments of the present invention.

DETAILED DESCRIPTION

Overview

Figure 1:
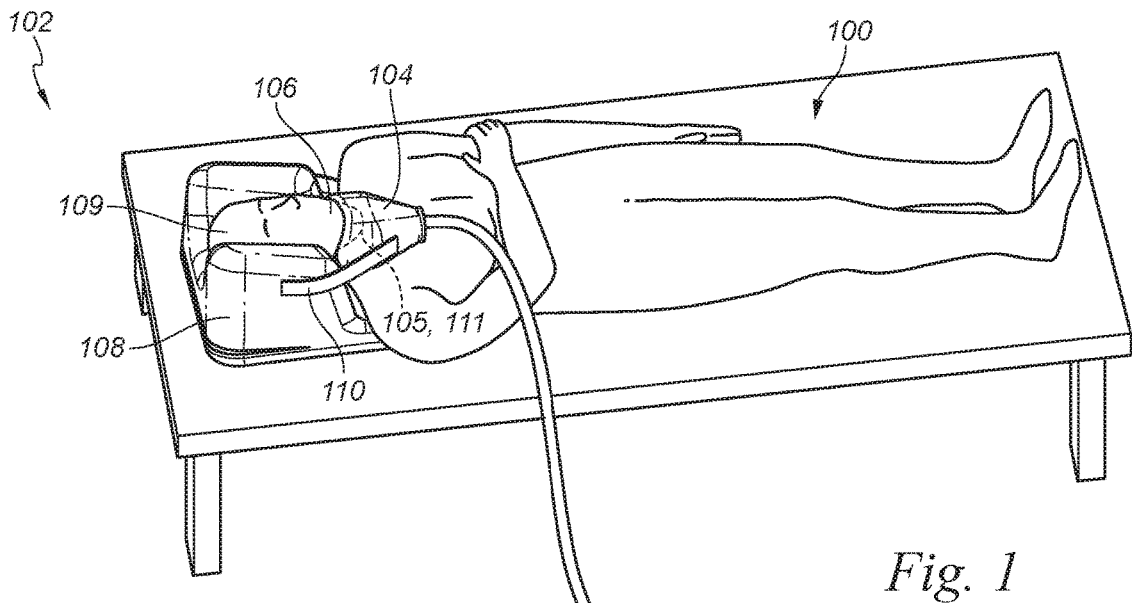
FIG. 1 is an isometric view of a subject and a treatment system for cooling tissue in accordance with an embodiment of the present invention.

During a cooling treatment, it can be useful to maintain stable thermal and physical contact between an applicator and a tissue region receiving the treatment. When this thermal and physical contact is broken or altered, the tissue region or portions thereof may rewarm prematurely, thereby causing the treatment to have a diminished effect or even no effect. Additionally, the applicator oftentimes includes various sensors that depend on stable contact between the tissue region and the applicator. These sensors, for example, are used to detect conditions such as applicator temperature, tissue temperature, quality of contact between the applicator and the tissue, and tissue properties (e.g., impedance, acoustic, and optical properties, etc.). The sensor readings are sometimes used to detect freeze events which causes treatment parameters to be changed in response thereto. When physical contact between the applicator and the tissue region is disrupted for any reason, such as by patient motion, any resulting X, Y, or Z axis motion between the applicator and the tissue region can create a serious signal artifact from at least some of these sensors. This, in turn, can lead to false sensor readings and incorrect corrective action, such as under or over cooling, a premature alarm, premature cessation of treatment, incorrect freeze event detections, etc.

Conventional approaches to maintaining stable thermal and physical contact between an applicator and a subject's skin during cooling treatments include use of suction and/or restraints (e.g., straps). While effective in many cases, these conventional approaches have limitations. For example, suction is applied to a subject's skin via an air gap that reduces a skin area available for thermal and physical contact with an applicator. The area of a subject's skin in contact with an air gap is directly proportional to the strength of the suction. Thus, when significant holding strength is desirable, achieving such holding strength by suction may require a large skin area to be in contact with an air gap and, therefore, not available for thermal and physical contact with an applicator. In the context of transdermal cooling, decreasing the area of a subject's skin available for thermal and physical contact with an applicator is typically undesirable. Furthermore, strong suction may be uncomfortable during long-duration treatments. Restraints may lessen or eliminate the need for suction, but only in limited cases. For example, unlike suction, restraints are typically not well suited for pulling and holding skin and underlying tissue in contact with three-dimensional surfaces. Also, use of suction and restraints generally allows for undue relative movement between the applicator and the tissue region when the subject moves for any of a variety of reasons which, as mentioned above, can cause false sensor readings, false alarms, and ineffective treatments.

Methods for cooling tissue and related structures and systems in accordance with embodiments of the present invention can at least partially address one or more problems associated with conventional technologies as discussed above and/or other problems whether or not such problems are stated herein. Methods in accordance with at least some embodiments of the present invention include use of temperature-dependent adhesive bonding to promote stable thermal and physical contact between an applicator and a tissue region. An adhesive that causes this bonding can be applied to one or more of a subject's skin, a heat transfer surface of an applicator, and an intervening structure (e.g., a liner). Furthermore, the adhesive can be applied independently (e.g., as a viscous layer) or carried by an absorbent substrate as part of a composite structure. The subject's skin and the heat-transfer surface of the applicator can then be brought together with the adhesive therebetween. The applicator can be used to cool the tissue region via the subject's skin, via the heat-transfer surface of the applicator, via the adhesive, and via various other intervening structures or materials when present at the treatment interface.

While the tissue region is cooled, the adhesive can also be cooled. This cooling of the adhesive can significantly strengthen the adhesion between the subject's skin and the heat-transfer surface of the applicator via the adhesive, thereby reducing or eliminating relative movement between the subject's skin and the heat-transfer surface of the applicator during the treatment. By way of theory, and without wishing to be bound to such theory, both increasing the viscosity of the adhesive and increasing the tackiness of the adhesive in response to cooling may contribute to the strengthened adhesion. Furthermore, the adhesive can have a viscosity and tackiness during application low enough to conform readily to irregularities in the subject's skin, but still high enough to maintain its shape. The viscosity and tackiness during application can also be low enough to allow an applicator to be ideally placed on the skin and moved into an optimal position. At a chilled temperature during tissue cooling, the viscosity and tackiness of the adhesive can be high enough to promote stable thermal and physical contact between the heat-transfer surface of the applicator and the tissue region and to keep the applicator fixed in position relative to the skin regardless of patient motion during the treatment. Thus, relative to conventional counterparts, methods for cooling tissue and related structures and systems in accordance with at least some embodiments of the present invention have less or no need for suction, restraints, and/or other mechanisms for maintaining stable thermal and physical contact between an applicator and a tissue region.

Specific details of methods for cooling tissue and related structures and systems in accordance with several embodiments of the present invention are described herein with reference to FIGS. 1-27. Although methods for cooling tissue and related structures and systems may be disclosed herein primarily or entirely in the context of cryolipolysis and cryolysis, other contexts in addition to those disclosed herein are within the scope of the present invention. For example, the disclosed methods, structures, and systems may be useful in the context of any compatible type of treatment mentioned in the applications and patents listed above and incorporated herein by reference. It should be understood, in general, that other methods, structures, and systems in addition to those disclosed herein are within the scope of the present invention. For example, methods, structures, and systems in accordance with embodiments of the present invention can have different and/or additional configurations, components, and procedures than those disclosed herein. Moreover, a person of ordinary skill in the art will understand that methods, structures, and systems in accordance with embodiments of the present invention can be without one or more of the configurations, components, and/or procedures disclosed herein without deviating from the present invention.

The term "treatment system," as used generally herein, refers to cosmetic, therapeutic or other medical treatment systems, as well as to any treatment regimens or medical device usage. At least some treatment systems configured in accordance with embodiments of the present invention are useful for reducing or eliminating excess adipose tissue or other undesirable tissue or enhancing the appearance of skin. In many cases, the treatment systems can be used at various locations, including, for example, a subject's face, neck, abdomen, thighs, buttocks, knees, back, arms, and/or ankles. Treatment systems in accordance with at least some embodiments of the present invention are well suited for cosmetically beneficial alterations of tissue at targeted anatomical regions. Some cosmetic procedures may be for the sole purpose of altering a target region to conform to a cosmetically desirable look, feel, size, shape, and/or other desirable cosmetic characteristic or feature. Accordingly, at least some embodiments of the cosmetic procedures can be performed without providing an appreciable therapeutic effect (e.g., no therapeutic effect). For example, some cosmetic procedures may not include restoration of health, physical integrity, or the physical well-being of a subject. The cosmetic methods can target subcutaneous or dermal regions to change a subject's appearance and can include, for example, procedures performed on subject's submental region, face, neck, ankle region, or the like. In other embodiments, however, desirable treatments may have therapeutic outcomes, such as alteration of vascular malformations, treatment of glands including sebaceous and sweat glands, treatment of nerves, alteration of body hormones levels (by the reduction of adipose tissue), etc.

Reference throughout this specification to "one example," "an example," "one embodiment," or "an embodiment" means that a particular feature, structure, or characteristic described in connection with the example is included in at least one example of the present invention. Thus, the occurrences of the phrases "in one example," "in an example," "one embodiment," or "an embodiment" in various places throughout this specification are not necessarily all referring to the same example. Furthermore, the particular features, structures, routines, stages, or characteristics may be combined in any suitable manner in one or more examples of the invention. The headings provided herein are for convenience only and are not intended to limit or interpret the scope or meaning of the invention.

Treatment Systems

FIG. 1 is a partially schematic, isometric view of a subject 100 and a treatment system 102 for cooling tissue in accordance with an embodiment of the present invention. It should be understood that aspects of the present invention can be practiced with numerous different treatment systems, of which the treatment system 102 is merely one example. As shown in FIG. 1, the treatment system 102 can include an applicator 104 that conforms closely to contours of the subject's body. In the illustrated embodiment, the applicator 104 is placed at a treatment site 105 under the subject's chin 106. In other embodiments, the applicator 104 can be placed at other suitable locations on the subject's body (e.g., at the abdomen, thigh, buttock, knee, back, arm, ankle, etc.). With reference again to FIG. 1, the treatment system 102 can include a head support 108 (e.g., a pillow) shaped to snugly receive the subject's head 109. The treatment system 102 can further include a restraint 110 (e.g., a strap) detachably connecting the applicator 104 to the head support 108. The restraint 110 can be configured to press the applicator 104 into firm contact with the subject's skin 111 at the treatment site 105. Structures and materials at the treatment interface between the applicator 104 and the subject's skin 111 are not shown in FIG. 1 and will be described with reference to subsequent figures.

Figure 2:
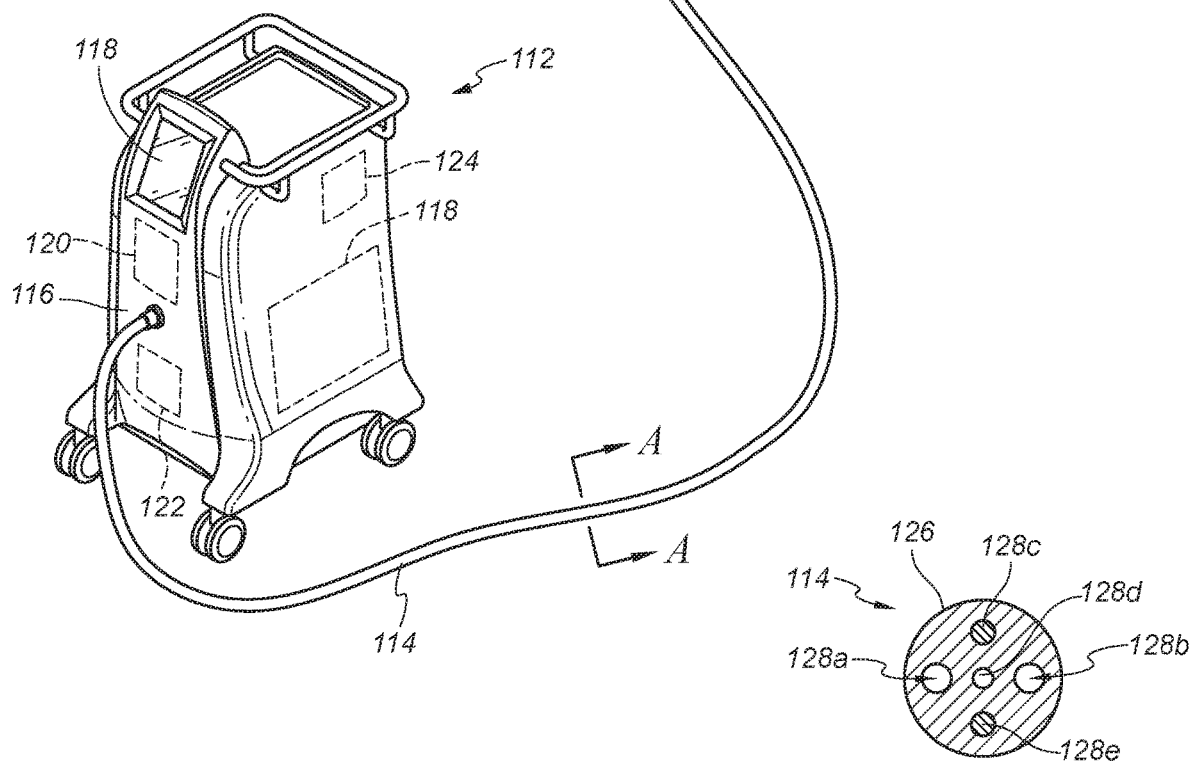
FIG. 2 is a cross-sectional view taken along the line A-A in FIG. 1.

FIG. 2 is a cross-sectional view taken along the line A-A in FIG. 1. With reference to FIGS. 1 and 2 together, the treatment system 102 can include a control module 112 and a connector 114 (e.g., a cable) extending between the control module 112 and the applicator 104. The control module 112 can include a housing 116 containing a fluid system 118, a power supply 120, a suction system 122, and a controller 124. The fluid system 118 can be configured to chill and to circulate a heat-transfer fluid (e.g., water, glycol, or oil) through the applicator 104. For example, the fluid system 118 can include suitable fluid-cooling and fluid-circulating components (not shown), such as a fluid chamber, a refrigeration unit, a cooling tower, a thermoelectric chiller, and/or a pump. The heat-transfer fluid can be one that transfers heat with or without phase change. In some embodiments, the fluid system 118 also includes suitable fluid-heating components (also not shown), such as a thermoelectric heater configured to heat the heat-transfer fluid such that the applicator 104 can provide heating as well as cooling at the treatment site 105. In other embodiments, the treatment system 102 is configured for cooling only.

The connector 114 can include an elongate main body 126 and lines 128 (individually identified as lines 128a-128e) within the main body 126. The lines 128 can extend longitudinally between the control module 112 and the applicator 104. In the illustrated embodiment, the lines 128 include a supply fluid line 128a operably connected to the fluid system 118, a return fluid line 128b also operably connected to the fluid system 118, a power line 128c operably connected to the power supply 120, a suction line 128d operably connected to the suction system 122, and a control line 128e operably connected to the controller 124. In other embodiments, a counterpart of the connector 114 can carry other suitable lines in addition to or instead of the illustrated lines. Furthermore, the control module 112 and the applicator 104 can be configured to communicate wirelessly in addition to or instead of communicating via the connector 114.

When in use, the treatment system 102 can deliver heat-transfer fluid continuously or intermittently from the control module 112 to the applicator 104 via the supply fluid line 128a. Within the applicator 104, the heat-transfer fluid can circulate to absorb heat from the treatment site 105. The heat-transfer fluid can then flow from the applicator 104 back to the control module 112 via the return fluid line 128b. For warming periods, the control module 112 can actively heat the heat-transfer fluid such that warm heat-transfer fluid is circulated through the applicator 104. Alternatively or in addition, the heat-transfer fluid can be allowed to warm passively. In the illustrated embodiment, the applicator 104 relies on circulation of heat-transfer fluid to maintain a thermal gradient at the treatment site 105 and thereby drive cooling or heating. In other embodiments, a counterpart of the applicator 104 can include a thermoelectric element that supplements or takes the place of circulation of heat-transfer fluid to maintain this thermal gradient. The thermoelectric element can be configured for cooling (e.g., by the Peltier effect) and/or heating (e.g., by resistance). For example, in some embodiments, a counterpart of the applicator 104 can rely on circulation of heat-transfer fluid to drive cooling and a thermoelectric element to drive heating.

The control module 112 can control the suction system 122 to apply suction at the treatment site 105 via the applicator 104 and via the suction line 128d. Suction can be useful for securing a liner (not shown) to the applicator 104 and/or for drawing and holding skin 111 and underlying tissue at the treatment site 105 into contact with the applicator 104 or the applicator liner, and/or for other purposes. Suitable suction levels can be selected based on characteristics of the tissue at the treatment site 105, patient comfort, and/or the holding power of a temperature-dependent adhesive (not shown) at the treatment site 105. The power supply 120 can be configured to provide a direct current voltage for powering electrical elements (e.g., thermal and sensor devices) of the applicator 104 via the power line 128c. For example, the control module 112 can include an input/output device 130 (e.g., a touchscreen) operably connected to the controller 124. The input/output device 130 can display a state of operation of the treatment system 102 and/or a progress of a treatment protocol.

The controller 124 can be in communication with the applicator 104 and can have instructions for causing the treatment system 102 to use the applicator 104 to cool tissue at the treatment site 105. In at least some embodiments, the controller 124 exchanges data with the applicator 104 via the control line 128e, via a wireless communication link, via an optical communication link, and/or via another suitable communications link. The controller 124 can monitor and adjust a treatment based on, without limitation, one or more treatment profiles and/or patient-specific treatment plans, such as those described, in commonly assigned U.S. Pat. No. 8,275,442, which is incorporated herein by reference in its entirety. Suitable treatment profiles and patient-specific treatment plans can include one or more segments, each including a temperature profile, a vacuum level, and/or a duration (e.g., 1 minute, 5 minutes, 10 minutes, 20 minutes, 30 minutes, 1 hour, 2 hours, etc.).

Figure 3:
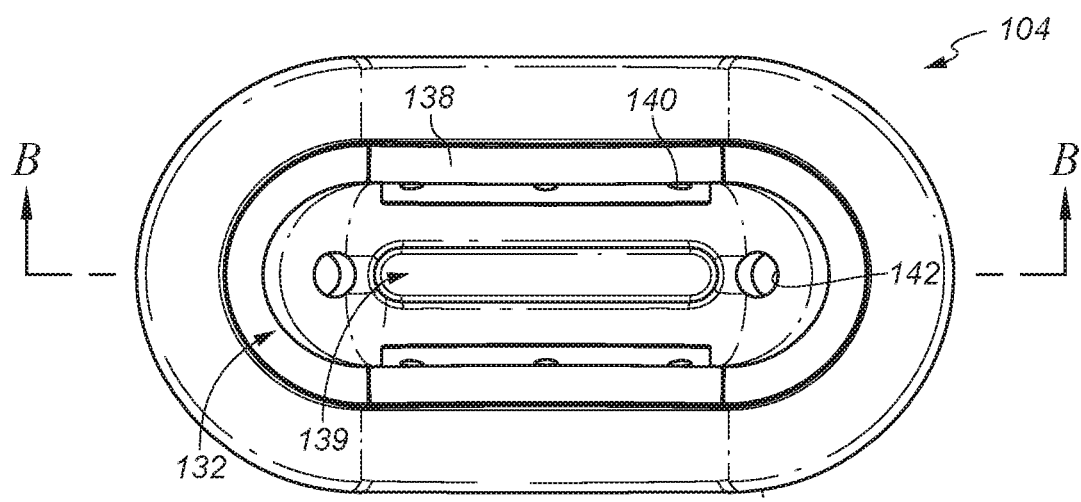
FIG. 3 is an end plan view of an applicator of the treatment system shown in FIG. 1.
Figure 4:
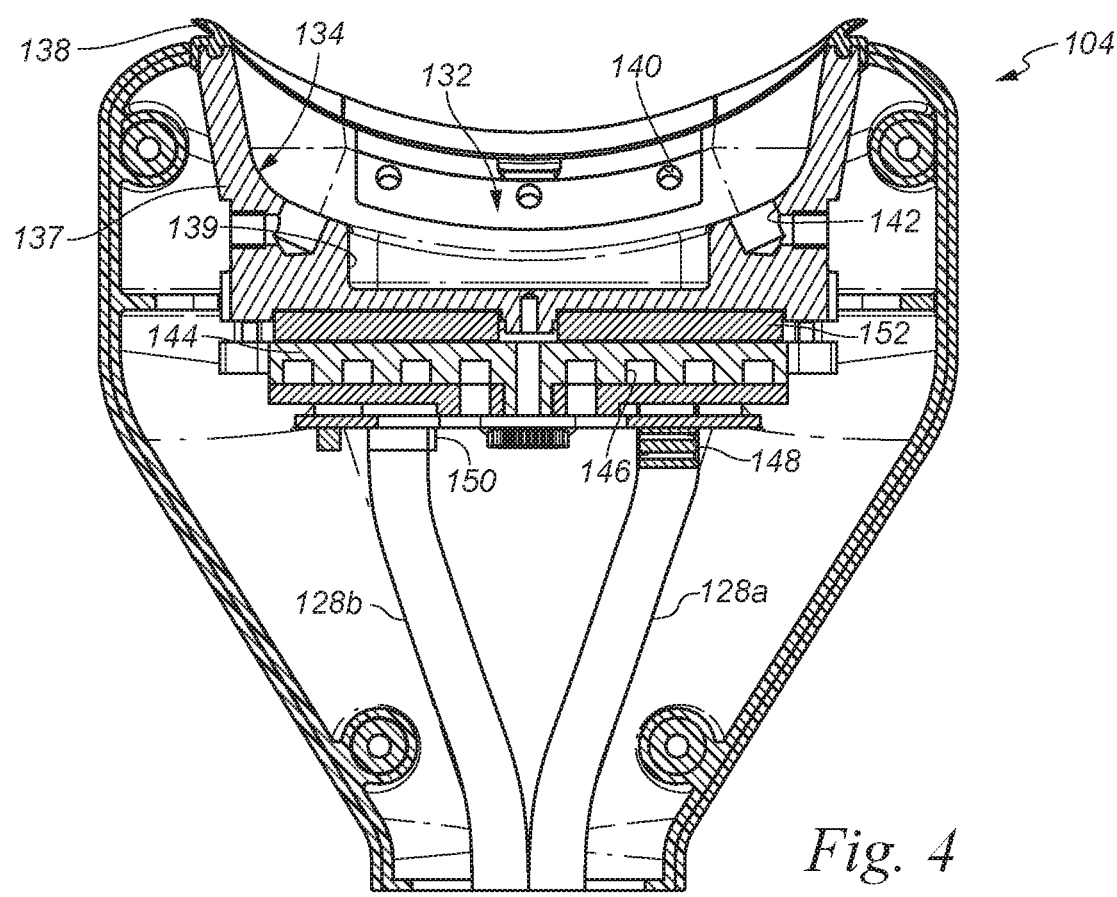
FIG. 4 is a cross-sectional view taken along the line B-B in FIG. 3.
Figure 5:
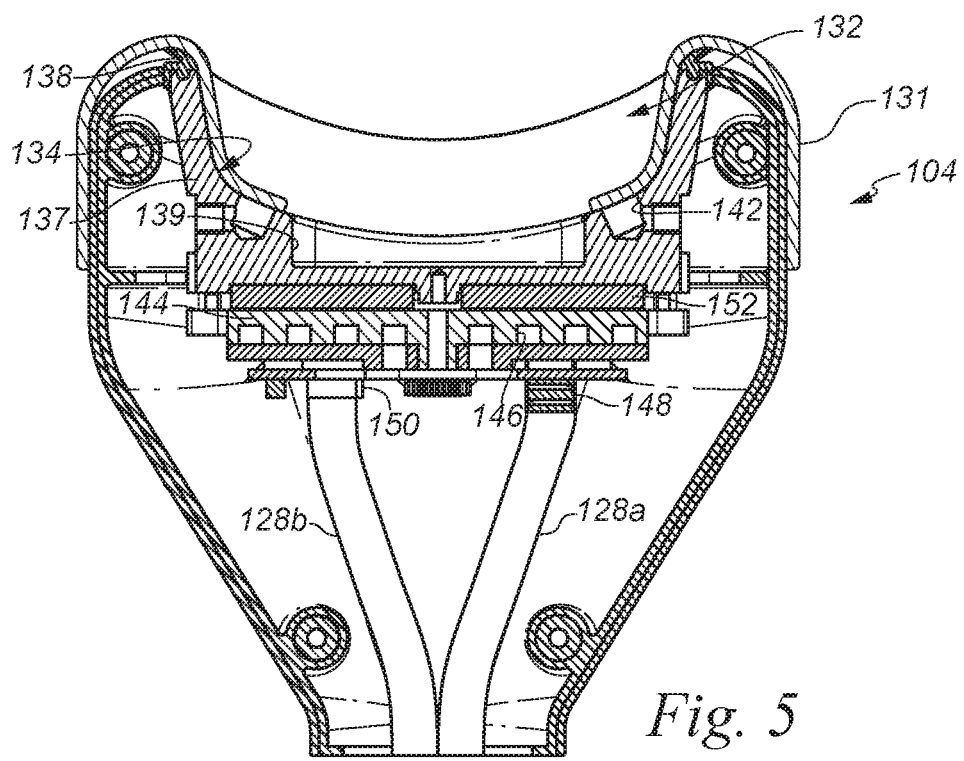
FIGS. 5 and 6 are cross-sectional views corresponding to FIG. 4 showing the applicator of the treatment system shown in FIG. 1 after installation of a removable liner (FIG. 5) and during a cooling procedure performed on the subject shown in FIG. 1 (FIG. 6).
Figure 6:
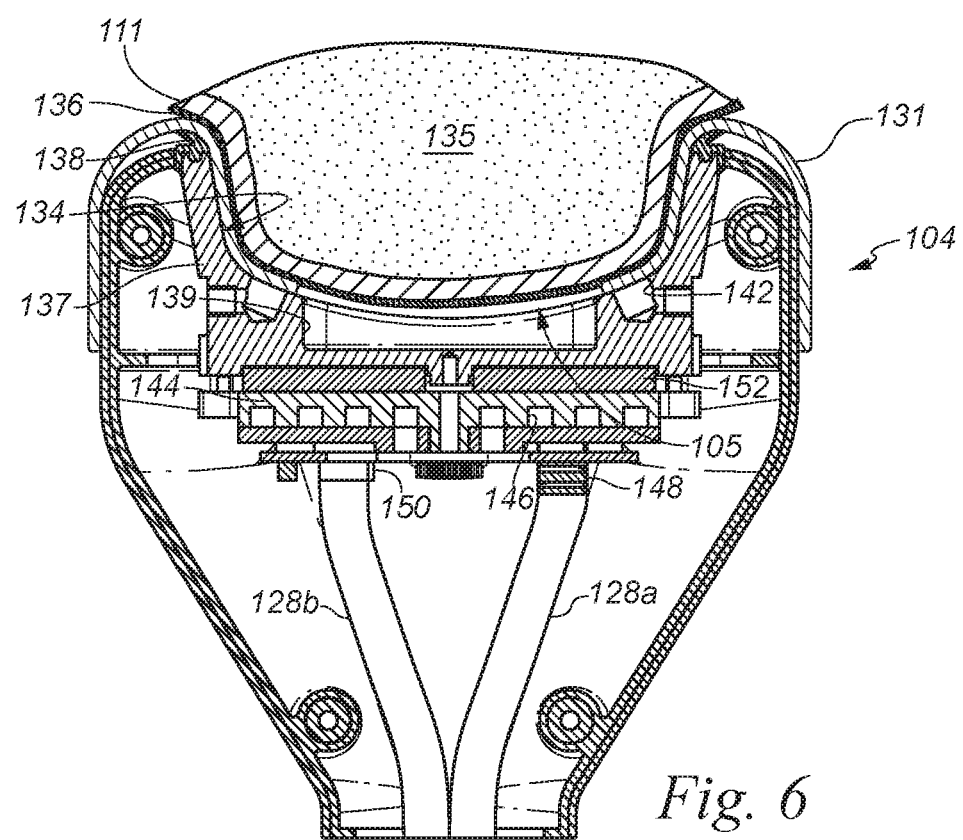

FIG. 3 is an end plan view of the applicator 104. FIG. 4 is a cross-sectional view taken along the line B-B in FIG. 3. FIGS. 5 and 6 are cross-sectional views corresponding to FIG. 4 showing the applicator 104 after installation of a removable liner 131 (FIG. 5) and during a cooling procedure performed on the subject 100 (FIG. 6). With reference to FIGS. 1-6 together, the applicator 104 can define a tissue-receiving cavity 132 and can include a heat-transfer surface 134 within the cavity 132. The heat-transfer surface 134 can be a durable surface through which the applicator 104 is configured to cool tissue 135 at the treatment site 105. During this cooling, the liner 131 and an adhesive 136 can be disposed between the heat-transfer surface 134 and the tissue 135. The liner 131 can be useful, for example, to help keep the applicator 104 clean during a treatment. The adhesive 136, discussed in detail below, can be useful, for example, to maintain stable thermal and physical contact between heat-transfer surface 134 and the tissue 135. The liner 131 can be attached to the applicator 104 with a liner adhesive (not shown) and/or held in place in another suitable manner, such as a vacuum generated by the applicator 104. When present, a liner adhesive between the liner 131 and the heat-transfer surface 134 need not have any special properties, such as temperature-dependent adhesive power and/or viscosity as discussed below with regard to the adhesive 136.

The heat-transfer surface 134 can be temperature controlled, such as via the controller 124. In the illustrated embodiment, the heat-transfer surface 134 is three-dimensional. In other embodiments, the heat-transfer surface 134 can be two-dimensional. As shown in FIG. 4, the applicator 104 can include a cup 137 defining a body of the cavity 132, and a contoured lip 138 defining a mouth of the cavity 132. The cup 137 can be contoured to accommodate the tissue 135 pulled into the cavity 132 and can serve as a heat sink to facilitate cooling of the tissue 135. The lip 138 can be configured to sealingly engage the subject's skin 111 and/or to sealingly engage the liner 131, the adhesive 136, or another intervening structure or material disposed between the heat-transfer surface 134 and the subject's skin 111. The applicator 104 can include a slot 139 at a lowermost portion of the cavity 132. The applicator 104 can further include side suction ports 140 and end suction ports 142 within the cavity 132 and around the slot 139. The slot 139, the side suction ports 140, and the end suction ports 142 can be operably connected to the suction system 122 via the suction line 128d and via additional suction lines (not shown) within the applicator 104. In the illustrated embodiment, the applicator 104 is configured to hold the liner 131 within the cavity 132 by suction at the side and end suction ports 140, 142 in addition to or instead of by use of liner adhesive disposed on a surface of the liner 131 facing the applicator 104.

Suction at the slot 139 can draw the tissue 135 into the cavity 132 and hold the tissue 135 within the cavity 132 with the assistance of the adhesive 136. As discussed below, the tensile adhesion and viscosity of the adhesive can increase with decreasing temperature such that the initial adhesion provided by the adhesive may be relatively weak. In other embodiments, a counterpart of the applicator 104 can be configured for use without a removable liner, and suction at the side and end suction ports 140, 142 and the slot 139 can draw the tissue 135 into the cavity 132 and hold the tissue 135 within the cavity 132. In still other embodiments, a counterpart of the applicator 104 can have other suitable suction configurations. Furthermore, counterparts of the applicator 104 can be without suction functionality, such as when drawing the tissue 135 into the cavity 132 and holding the tissue 135 within the cavity 132 is not needed. For example, a counterpart of the applicator 104 that is substantially flat or slightly curved may be placed directly on the subject's skin 111 without use of any suction and held in place with only straps and the adhesive 136 or with just the adhesive 136.

With reference again to FIGS. 1-6, the applicator 104 can further include a fluid-cooled element 144 underlying the slot 139. The fluid-cooled element 144 can include channels 146 shaped to convey the heat-transfer fluid in a manner that promotes heat transfer via the heat-transfer surface 134. The applicator 104 can include an inlet port 148 and an outlet port 150 coupled to the supply fluid line 128a and the return fluid line 128b, respectively. The channels 146 can extend along a serpentine or other suitable path between the inlet port 148 and the outlet port 150. The applicator 104 can further include a thermoelectric element 152 disposed between the fluid-cooled element 144 and the slot 139. The fluid-cooled element 144 and the thermoelectric element 152 can be used together or separately to cause a desired level of cooling or heating. Using the fluid-cooled element 144 and/or the thermoelectric element 152 for heating may be useful, for example, to facilitate separating the applicator 104 from the treatment site after a cooling procedure is complete.

Figure 7:
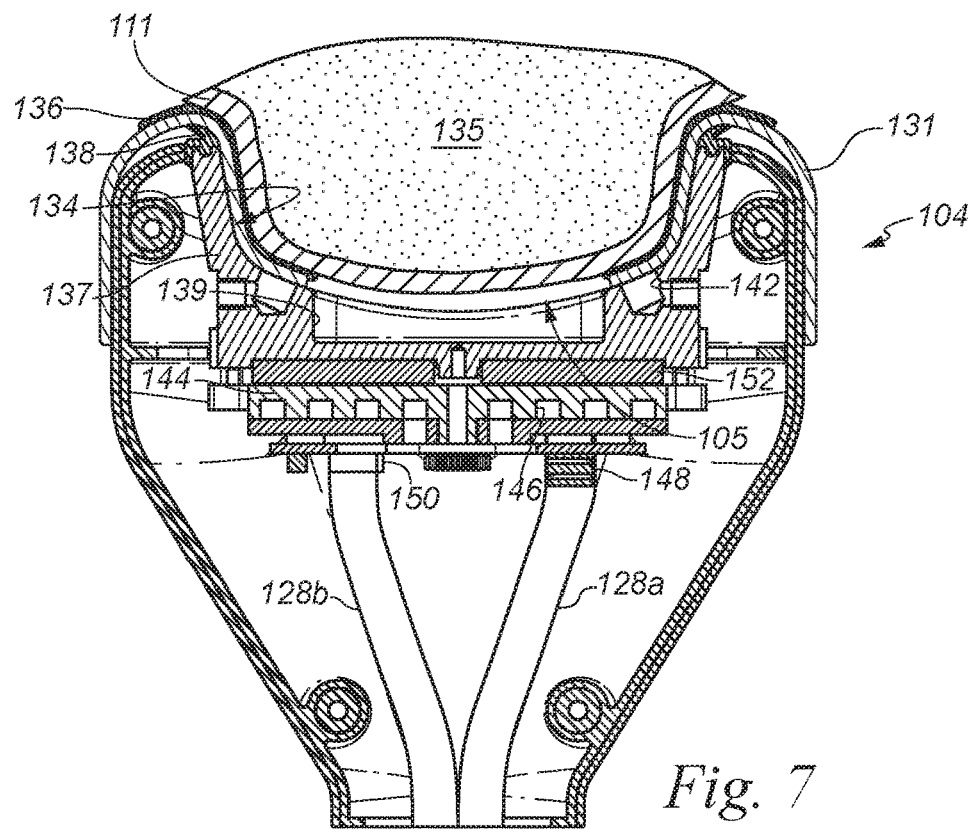
FIGS. 7-9 are cross-sectional views similar to FIG. 6 showing areas around treatment interfaces during cooling treatments in accordance with other respective embodiments of the present invention.
Figure 8:
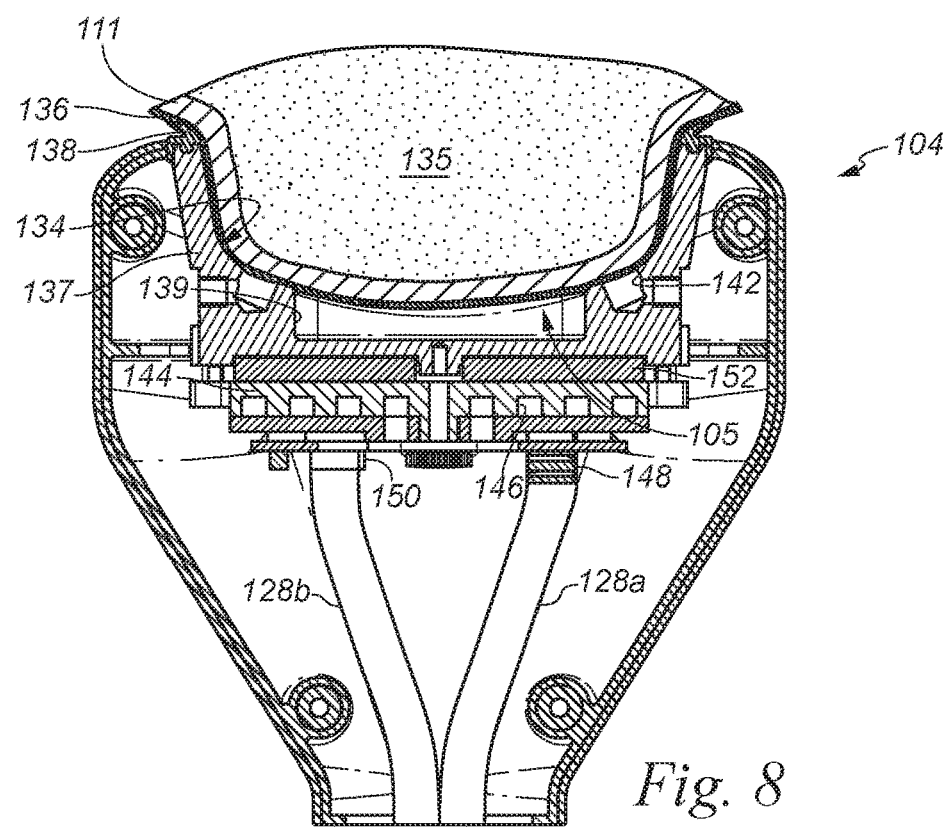
Figure 9:
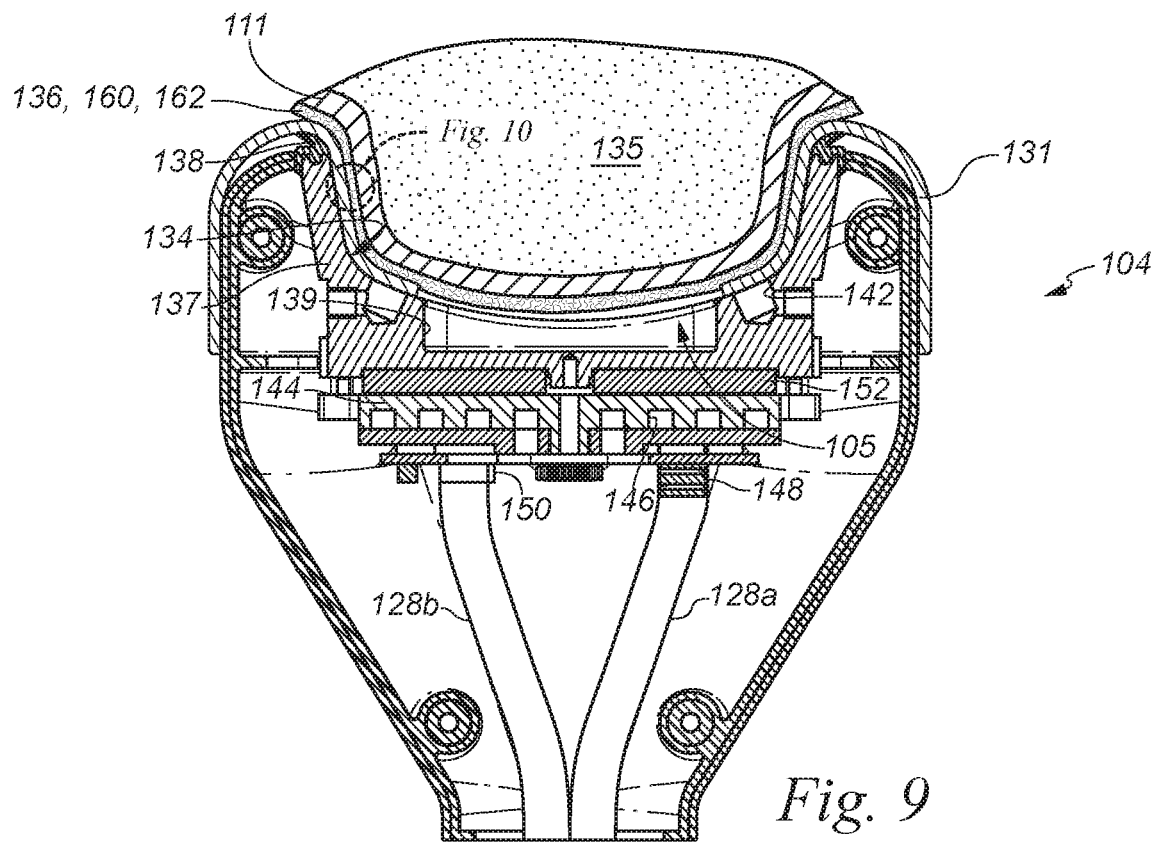

FIGS. 7-9 are cross-sectional views similar to FIG. 6 showing areas around a treatment interface during cooling treatments in accordance with other respective embodiments of the present invention. In particular, FIGS. 7-9 show different adhesive configurations at the treatment interface. In the embodiment illustrated in FIG. 7, the adhesive 136 is applied to the liner 131 before the liner 131 contacts the skin 111. Accordingly, the adhesive 136 can be absent from portions of the treatment site 105 not in contact with the liner 131. In some cases, the adhesive 136 is preloaded onto the liner 131. For example, the liner 131 can be packaged with a layer of the adhesive 136 and configured to be discarded after a single use. In other embodiments, the adhesive 136 can be applied to the liner 131 just before a treatment commences, such as just before or just after the liner 131 is removably connected to the applicator 104. In the embodiment illustrated in FIG. 8, the applicator 104 does not include a liner 131 and the adhesive 136 is disposed directly between the skin 111 and the heat-transfer surface 134. This arrangement may be desirable, for example, when protecting the adhesive 136 is not necessary, such as when the adhesive 136 is water soluble and the heat-transfer surface 134 is free of gaps and crevices in which the adhesive 136 may become embedded. In these and other cases, the slot 139, the side suction ports 140, and the end suction ports 142 can include filters (not shown) that prevent the adhesive 136 from being drawn into the suction system 122.

In the embodiment illustrated in FIG. 9, the adhesive 136 is carried by an absorbent substrate 160 disposed between the subject's skin 111 and the heat-transfer surface 134 of the applicator 104. Together, the adhesive 136 and the absorbent substrate 160 can form a composite structure 162 configured to be disposed at the treatment interface. The absorbent substrate 160 can be useful, for example, to facilitate application of the adhesive 136 at low viscosities, to hold the adhesive 136 in position at the treatment interface, to reduce or prevent displacement of the adhesive 136 during placement of the applicator 104, and/or to insure that a continuous layer of material is present between the applicator 104 and the subject's skin 111. Insuring that a continuous layer of material is present between the applicator 104 and the subject's skin 111 can likewise insure that no part of the applicator 104 directly touches the subject's skin 111. When supercooling treatment temperatures are used, such direct contact between the applicator 104 and the subject's skin 111 may be undesirable as it may inadvertently inoculate the skin 111 and cause a premature freeze event therein.

In some embodiments, the absorbent substrate 160 is tubular and stretchable so that it can be fitted around the subject's neck, arm, leg, torso, etc. In other embodiments, the absorbent substrate 160 can be a flat or curved pad or have other suitable forms for making optimum contact with a treatment site and yet be easy to apply and remove. The absorbent substrate 160 can include a stretchable fabric, mesh, or other porous material suitable for carrying the adhesive 136. Cotton, rayon, and polyurethane cloth are a few examples of suitable materials for use in the absorbent substrate 160. Furthermore, the absorbent substrate 160 can include a thermally conductive material that at least partially compensates for a lower thermal conductivity of the corresponding adhesive 136. Thus, in some cases, the composite structure 162 is more thermally conductive than the adhesive 136 alone. Higher thermal conductivity can be useful, for example, to facilitate detection of the thermal signature of a freeze event during a cooling procedure. When the absorbent substrate 160 include stretchable fabric, some or all of the fibers of the fabric can be made of thermally conductive material. For example, the fabric can include metal fibers, carbon fibers, and/or fibers having a thermally conductive coating. Carbon fiber fabric is available, for example, under the FLEXZORB trademark from Calgon Carbon (Pittsburgh, Pa.). These and other forms of the absorbent substrate 160 can be configured for single-use or multiple-use, and can be packaged with or without being preloaded with the adhesive 136. When the absorbent substrate 160 is preloaded with the adhesive 136, the corresponding composite structure 162 can be encased in moisture impermeable packaging (not shown) to protect the constituent adhesive 136 from the environment. Furthermore, the composite structure 162 can be packaged separately from or together with the liner 131. In a particular embodiment, the composite structure 162 is pre-positioned on the liner 131 such that the composite structure 162 and the liner 131 can simply be brought into contact with the subject's skin 111 without any need to separately position the composite structure 162. In another embodiment, the composite structure 162 is independent of the liner 131 and configured to be placed on the subject's skin 111 before establishing thermal and physical contact with the applicator 104.

Figure 10:
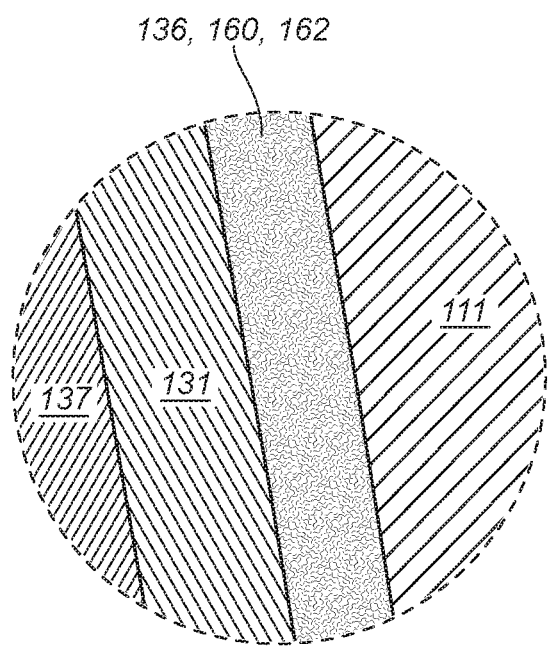
FIG. 10 is an enlarged view of a portion of FIG. 9.
Figure 11:
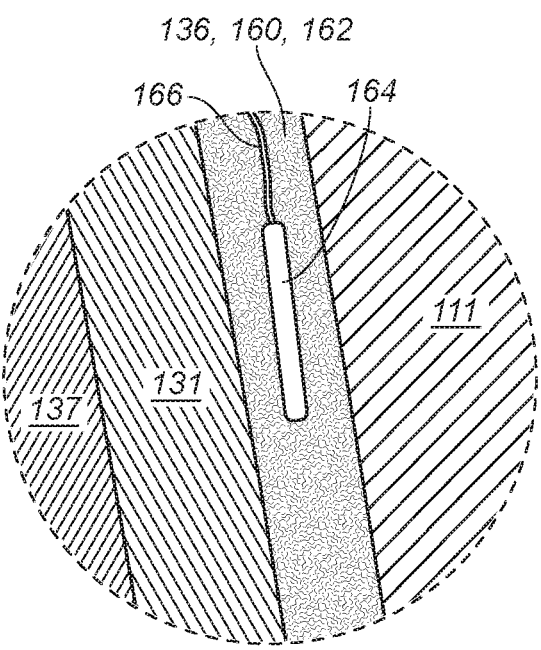
FIG. 11 is a cross-sectional view similar to FIG. 10 showing a thermal sensor at a treatment interface in accordance with another embodiment of the present invention.

FIG. 10 is an enlarged view of a portion of FIG. 9. FIG. 11 is a cross-sectional view similar to FIG. 10 showing a thermal sensor 164 at the treatment interface in accordance with another embodiment of the present invention. As shown in FIG. 11, the thermal sensor 164 can be carried by (e.g., embedded in) the absorbent substrate 160. Alternatively, a counterpart of the thermal sensor 164 can be carried by (e.g., embedded in) another suitable portion of the applicator 104, such as the heat-transfer surface 134 of the applicator 104. The thermal sensor 164 can be useful, for example, to facilitate detection of the thermal signature of a freeze event at the skin 111 by shortening the distance over which thermal energy associated with a freeze event must conveyed before detection. The thermal sensor 164 can include a wire 166 that extends out of the absorbent substrate 160 to a port (not shown) for connection to external electronics. Alternatively, the thermal sensor 164 can be configured to communicate with external electronics wirelessly. In some cases, the thermal sensor 164 is built into the absorbent substrate 160. In other cases, the thermal sensor 164 is inserted into the absorbent substrate 160 at the time of use. In these and other cases, the thermal sensor 164 can be single-use or multiple use.

FIGS. 12-13 show use of the adhesive 136 with different applicator types. In the embodiment illustrated in FIG. 12, the adhesive 136 is shown in use with a "pinch-type" applicator 170 at a treatment site 171. The applicator 170 can include a frame 172 having sidewalls 174 operably connected to respective cooling elements 176. The frame 172 can define an end gap 177 at which the applicator 170 includes a suction port 178. Suction at the end gap 177 can facilitate holding tissue 135 at the treatment site 171 in a captured state between the sidewalls 174 before cooling of the tissue 135 begins. After cooling of the tissue 135 begins, the adhesive 136 can cool and form a strong adhesive bond between the tissue 135 and the sidewalls 174. In at least some cases, the suction at the end gap 177 is reduced after the adhesive bond between the tissue 135 and the sidewalls 174 is strengthened. Reducing the suction at the end gap 177 can be useful, for example, to reduce or eliminate suction-related blood pooling at a portion of the tissue 135 closest to the end gap 177. Additional details regarding "pinch-type" applicators that can be used with adhesive 136 in accordance with at least some embodiments of the present invention can be found, for example, in U.S. Patent Application Publication No. 2015/0342780 and U.S. patent application Ser. No. 14/662,181, which are incorporated herein by reference in their entireties.

In the embodiment illustrated in FIG. 13, the adhesive 136 is shown in use with another cup type applicator 179 similar to the applicator 104 (FIG. 6). The applicator 179 is also similar to the applicator 170 (FIG. 12) except that no end gap 177 exists between the skin 111 and a heat transfer surface of the applicator 179. The applicator 179 can include a cup 180 and a suction port 181 at a base of the cup 180 that fully draws the tissue 135 into the cup 180. Like the applicator 104 (FIG. 6) and the applicator 170 (FIG. 12), the applicator 179 is a three-dimensional applicator well suited for use with tissue that can be pulled away from a subject's body. In at least some cases, the treatment interfaces associated with these applicators are also three dimensional. It should be understood, however, that the adhesive can also be used with applicators that cool tissue via a two-dimensional treatment interface.

In the embodiment illustrated in FIG. 14, the adhesive 136 is shown in use with a "saddlebag-type" applicator 182 at a treatment site 183. The applicator 182 can include a cooling element 184 coupled to a central backing 186. The applicator 182 can further include suction elements 188 coupled to respective lateral backings 190. The lateral backings 190 can be hingedly connected to the central backing 186 at opposite respective sides of the central backing 186. A strap (not shown) can be used to initially secure the applicator 182 at the treatment site 183 by compression. Suction at the suction elements 188 optionally can facilitate holding tissue 135 at the treatment site 171 in stable contact with the cooling element 184 before cooling of the tissue 135 begins. After cooling of the tissue 135 begins, the adhesive 136 can cool and form a strong adhesive bond between the tissue 135 and the cooling element 184 sufficient to hold the applicator 182 in place without continued use of any straps or suction. In at least some cases, compression from the strap and/or suction from the suction elements 188 can be reduced or eliminated entirely after the adhesive bond between the tissue 135 and the cooling element 184 is strengthened. Reducing compression from the strap and/or suction from the suction elements 188 can be useful, for example, to enhance patient comfort. Additional details regarding "saddlebag-type" applicators that can be used with the adhesive 136 in accordance with at least some embodiments of the present invention can be found, for example, in U.S. Patent Application Publication No. 2015/0342780 and U.S. patent application Ser. No. 14/662,181, which are incorporated herein by reference in their entireties.

Treatment Methods

Figure 15:
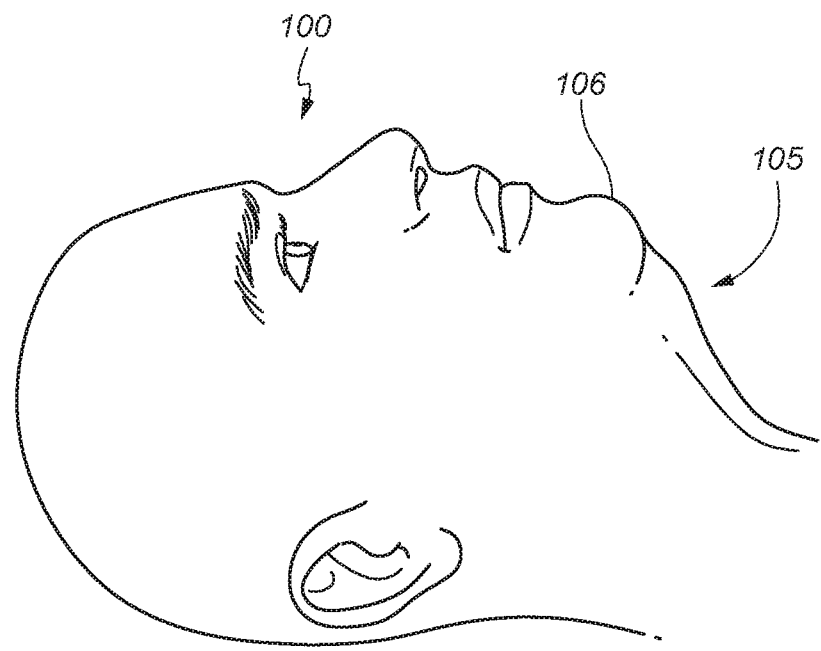
FIGS. 15-18 are side views of the subject shown in FIG. 1 and nearby structures at different respective stages during a cooling treatment performed on the subject using the treatment system shown in FIG. 1 in accordance with an embodiment of the present invention.
Figure 16:
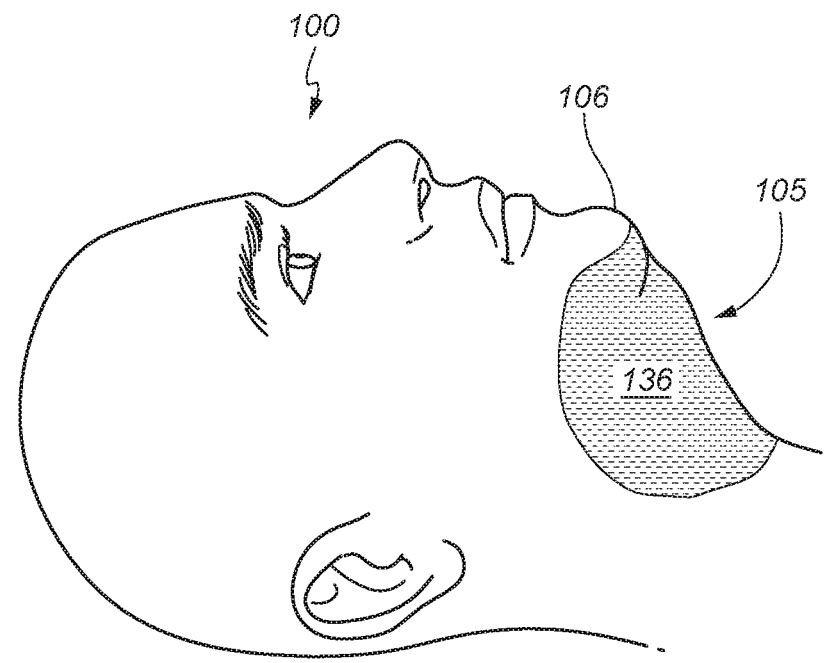
Figure 17:
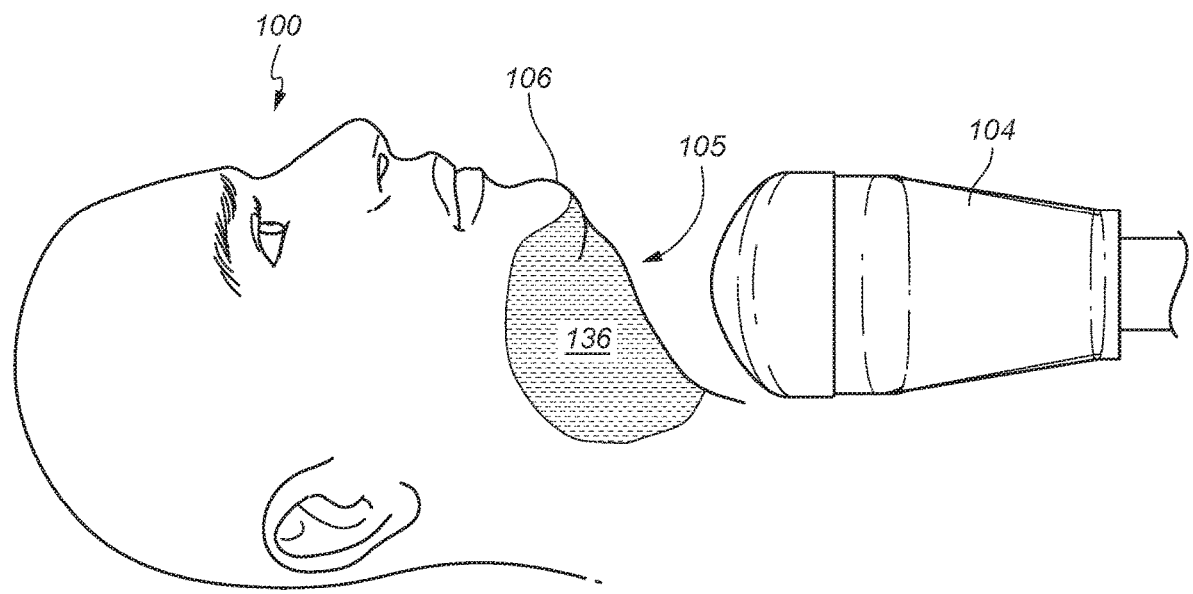
Figure 18:
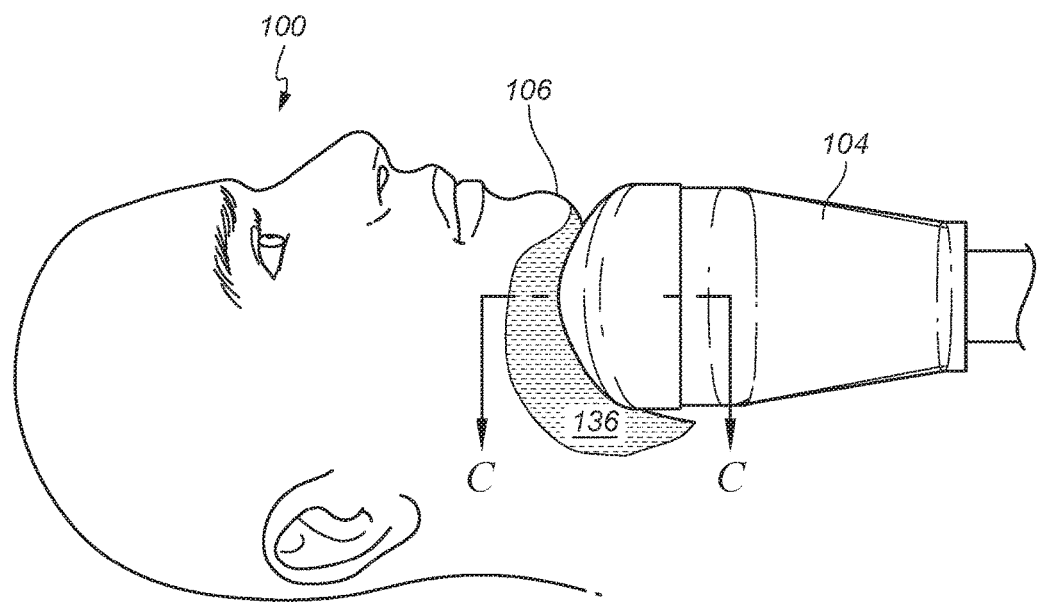

FIGS. 15-18 are side views of the subject 100 at different respective stages during a cooling treatment performed on the subject 100 using the treatment system 102 (FIG. 1) in accordance with an embodiment of the present invention. In FIG. 15, the subject 100 is shown before the treatment begins. In FIG. 16, the subject 100 is shown after an adhesive 136 has been applied to the subject's skin 111 at the treatment site 105 as a viscous layer. The adhesive 136 can be applied to the skin 111 at the treatment site 105 by brushing, by smearing, by placing (e.g., when the adhesive 136 is carried by an absorbent substrate), and/or by another suitable application technique. In at least some embodiments, the adhesive 136 has a viscosity at an application temperature (e.g., room temperature or body temperature) high enough to form a stable viscous layer on skin yet low enough to readily conform to irregularities (e.g., creases) typically present in skin. For example, the adhesive 136 can be applied to the skin 111 at the treatment site 105 at a viscosity within a range from 5,000 to 500,000 centipoise, such as within a range from 10,000 to 100,000 centipoise. In addition, when applied, the adhesive 136 can have a low tackiness, which substantially increases after it is cooled. After the adhesive 136 has been applied, the applicator 104 can be staged (FIG. 17) and then moved into contact with the subject 100 at the treatment site 105 (FIG. 18). During and shortly after this contact is established, the applicator 104 can be precisely positioned in view of the relatively low viscosity and tackiness of the adhesive 136 at the application temperature.

Figure 19:
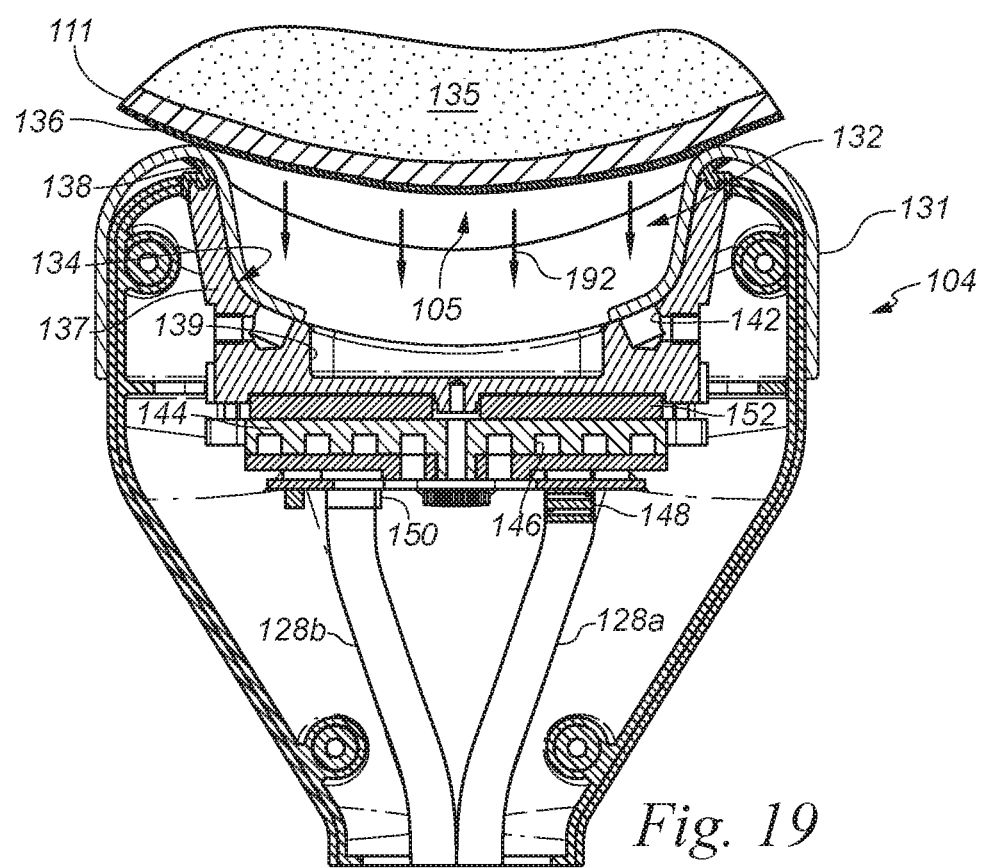
FIGS. 19 and 20 are cross-sectional views taken along line C-C in FIG. 18 at different respective stages during the cooling treatment.
Figure 20:
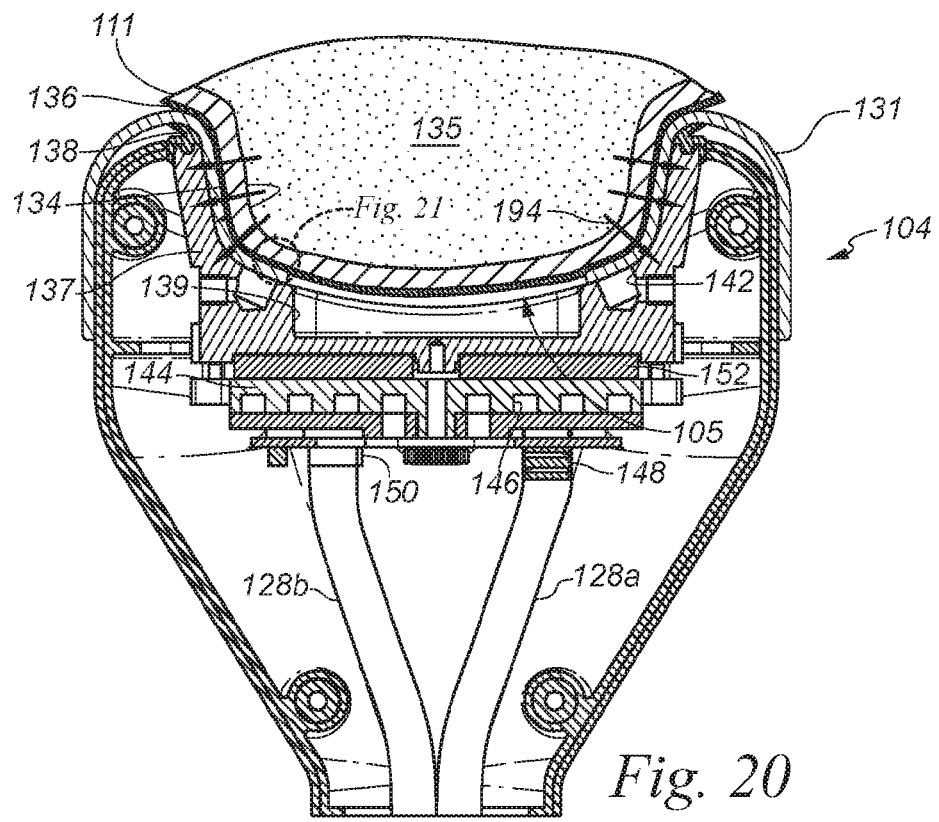

FIGS. 19 and 20 are cross-sectional views taken along line C-C in FIG. 18 at different respective stages during the cooling treatment. When the applicator 104 first contacts the treatment site 105, the skin 111 and the underlying tissue 135 at the treatment site 105 can be mostly outside the cavity 132. Suction, represented by arrows 192 in FIG. 19, can draw the skin 111 and the underlying tissue 135 into the cavity 132 until the skin 111 and the underlying tissue 135 move into thermal and physical contact with the heat-transfer surface 134 of the applicator 104. The thermal and physical contact between the tissue 135 and the heat-transfer surface 134 can extend through the skin 111, through the adhesive 136, through the liner 131 and through any liner adhesive (not shown) between the liner 131 and the heat-transfer surface 134 of the applicator 104. The adhesive 136 can be present at a thickness sufficient to promote adhesion between the skin 111 and the heat-transfer surface 134 via the liner 131 yet thin enough not to unduly reduce thermal conductivity between the tissue 135 and the heat-transfer surface 134. In at least some cases, the adhesive 136 is present at an average thickness within a range from 0.1 to 1 millimeter, such as within a range from 0.2 to 0.5 millimeter. In a particular embodiment, the adhesive 136 present at an average thickness of 0.3 millimeter.

When the skin 111 and the underlying tissue 135 first move into thermal and physical contact with the heat-transfer surface 134, the adhesive 136 can form a weak adhesive bond between the skin 111 and the heat-transfer surface 134. Thus, in at least some cases, the applicator 104 is readily repositionable before cooling begins. Repositioning the applicator 104 can be useful, for example, when an initial position of the applicator 104 is suboptimal. Once the applicator 104 is properly positioned and the tissue 135 and the heat-transfer surface 134 are in thermal and physical contact with one another (and in direct physical contact with one another when the liner 131 is not present), the applicator 104 can be activated to draw heat (represented by arrows 194 in FIG. 20) from the tissue 135. In this way, the applicator 104 can cool the tissue 135 via the skin 111, via the adhesive 136, via the liner 131, via any liner adhesive, and via the heat-transfer surface 134 of the applicator 104. The adhesive 136 can be cooled while cooling the tissue 135. Cooling the adhesive 136 can cryogenically strengthen the direct or indirect adhesive bond between the skin 111 and the heat-transfer surface 134 and thereby strengthen an adhesion between the skin 111 and the heat-transfer surface 134 via the adhesive 136 and via the liner 131. This can inhibit or totally prevent movement of the applicator 104 relative to the skin 111 while the adhesive 136 is chilled.

After the adhesive bond between the skin 111 and the heat-transfer surface 134 has been cryogenically strengthened, the applicator 104 may no longer be readily repositionable. In at least some cases, cooling the adhesive 136 from an application temperature to a chilled temperature in conjunction with a cooling treatment can at least increase a tensile strength of the adhesive bond between the skin 111 and the heat-transfer surface 134 by a factor of more than 1.25×, 1.5×, 2×, 3×, 4×, 5×, 6×, 7×, 10×, 20×, or 30×. For example, a force required to break adhesion between the skin 111 and the heat-transfer surface 134 in a direction normal to the heat-transfer surface 134 when the adhesion is cryogenically strengthened can be at least a factor of more than 1.25×, 1.5×, 2×, 3×, 4×, 5×, 6×, 7×, 10×, 20×, or 30× a corresponding force required to break the adhesion before the adhesion is cryogenically strengthened. Similarly, cooling the adhesive 136 from an application temperature to a chilled temperature in conjunction with the cooling treatment can at least increase a shear strength of the adhesive bond between the skin 111 and the heat transfer surface 134 by a factor of more than 1.25×, 1.5×, 2×, 3×, 4×, 5×, 6×, 7×, 10×, 20×, or 30× a shear strength of the adhesive bond between the skin 111 and the heat-transfer surface 134 before the shear strength is cryogenically strengthened. For example, a force required to break the adhesion between the skin 111 and the heat-transfer surface 134 in a direction parallel to the heat-transfer surface 134 when the adhesion is cryogenically strengthened can be at least a factor of more than 1.25×, 1.5×, 2×, 3×, 4×, 5×, 6×, 7×, 10×, 20×, or 30× such a force required to break adhesion before the adhesion is cryogenically strengthened. An increase in shear strength can be important to prevent any X, Y axis relative movement between the skin 111 and the heat transfer surface 134 during a cooling treatment.

For "cup-type" applicators (e.g., the applicator 104 shown in FIG. 6) or "pinch-type" applicators (e.g., the applicator 170 shown in FIG. 12) where tissue is drawn into a cup or well having side walls, an increased shear strength can be very effective in reducing or eliminating relative movement between skin and a heat transfer surface. This can be useful to reduce or eliminate "pop off" or other types of undesirable shifting or separation between these applicators and skin at a treatment site. For surface applicators (e.g., the applicator 182 shown in FIG. 14), increased tensile strength preventing motion along the Z axis can be very effective to reduce or eliminate relative movement between skin and a heat transfer surface in the Z axis. Again, this can be useful to reduce or eliminate "pop off" or other types of undesirable shifting or separation between these applicators and skin at a treatment site.

In addition to using adhesives as described which exhibit a large reversible change in adhesive power and viscosity in response to a change in temperature, those skilled in the art will appreciate that any material used to form an adhesive absorbent (when used), liner (when used), heat transfer surface, and any other components that may come in contact with the adhesive should be compatible with the adhesive. For example, these other structures and materials can be selected to preferably wet to the adhesive and form strong bonds thereto at treatment temperatures. For at least one tested adhesive formation, it has been found that aluminum, cotton, rayon, and polyurethane are compatible with the formation of strong adhesive bonds. Bonding strength has been found to increase when an absorbent substrate carrying an adhesive has a surface that is at least somewhat porous.

After the adhesive bond between the skin 111 and the heat-transfer surface 134 is cryogenically strengthened, a level of suction and/or compression initially used to urge the tissue 135 into the cavity 132 may be unneeded to maintain a position of the tissue 135 within the cavity 132. Accordingly, the level of suction and/or compression can be reduced, which can be beneficial, for example, to enhance patient comfort during long-duration treatments and/or to reduce undesirable side effects of the suction and/or compression. In some cases, thermal and physical contact between the tissue 135 and the heat-transfer surface 134 occurs primarily or solely by adhesion while the tissue 135 is cooled. In other cases, maintaining thermal and physical contact between the tissue 135 and the heat-transfer surface 134 can occur primarily by suction supplemented by adhesion while the tissue 135 is cooled.

In at least some embodiments, cooling the adhesive 136 from an application temperature to a chilled temperature in conjunction with a cooling treatment increases a viscosity of the adhesive 136 by at least 1,000% (e.g., at least 10,000%) on a centipoise scale. In these and other embodiments, cooling the adhesive 136 in this manner can cause the adhesive 136 to have a viscosity within a range from 3,000,000 centipoise to a maximum viscosity of the adhesive 136 at temperatures warmer than a glass transition temperature of the adhesive 136. Cooling the adhesive 136 to colder than its glass transition temperature can weaken the adhesion between the skin 111 and the heat-transfer surface 134 via the adhesive 136. Accordingly, the adhesive 136 can be selected to have a glass transition temperature colder than a coldest temperature to which the adhesive 136 is to be cooled during a cooling treatment. For example, the adhesive 136 can be selected to have a glass transition temperature colder than −20° C., such as colder than −30° C.

According to a particular embodiment, at room temperature or another suitable application temperature, the adhesive 136 has minimal adhesive force such that the applicator 104 can be readily placed on and removed from the skin 111 and moved sideways or twisted as need be to correctly position the applicator 104. For example, the adhesive force before cooling can be insufficient to keep the applicator 104 in a precise position and fixed in that position for a significant period of time without the use of some other holding force. However, at a treatment temperature, the adhesive force is dramatically increased such that the adhesive force alone is strong enough to keep the applicator 104 in place without any other attachment force. Other attachment forces that may become unnecessary can include suction, straps, or even the support of the subject's tissue 135 with the assistance of gravity (e.g., if the subject 100 is lying down and the applicator 104 is resting on top of the subject 100). In other words, the adhesive 136 is strong enough to secure the applicator 104 in place in any orientation. So even if the subject 100 is standing and the applicator 104 is simply hanging from the subject 100, such as from the subject's abdomen or side flank, the adhesive 136 is strong enough to secure the applicator 104 and keep it in place and non-movable relative to the skin 111 at the treatment site being treated by the applicator 104. Furthermore, the adhesive 136 can be strong enough to not only hold the applicator 104 in place and keep it from moving relative a subject's skin 111 when the subject is standing and the applicator 104 is hanging from the subject, but could do so even if the subject moves, shivers, or were to jump up and down.

Figure 21:
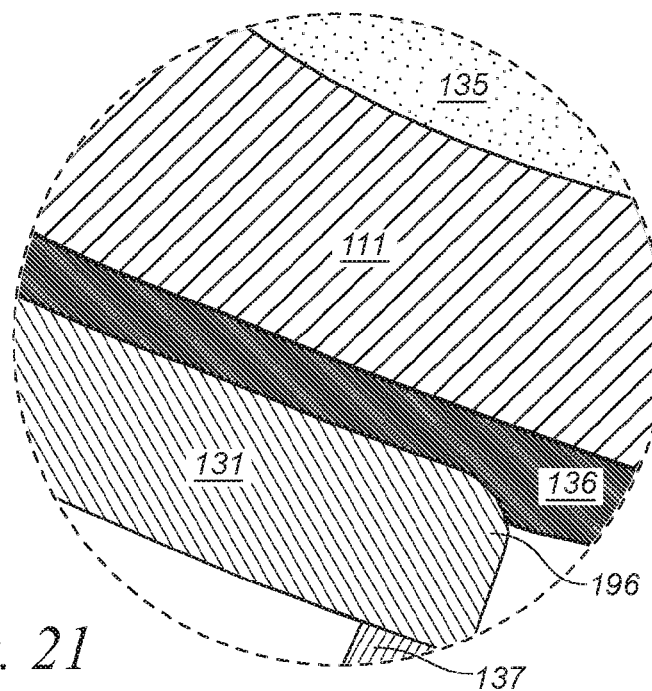
FIG. 21 is an enlarged view of a portion of FIG. 20.

FIG. 21 is an enlarged view of a portion of FIG. 20. As shown in FIG. 21, the liner 131 can have a rounded edge 196 at a perimeter of the slot 139. With reference to FIGS. 20 and 21 together, the adhesive 136 can be squeezed between the skin 111 and the liner 131 and thereby shifted toward the slot 139, toward an area above the lip 138, and/or toward other areas where the liner 131 is not present. For example, the adhesive 136 can be thicker at a side of the rounded edge 196 closer to the slot 139 than at a side of the rounded edge 196 farther from the slot 139. The adhesive 136 can have a viscosity upon application high enough that it does not entirely squeeze out of areas of the treatment site 105 pressed firmly against the liner 131. Because the adhesive 136 in the illustrated embodiment is applied to the subject's skin 111 before the subject's skin 111 is brought into contact with the liner 131, the adhesive 136 can be present at portions of the treatment site 105 not in contact with the liner 131, such as a portion of the treatment site 105 at the slot 139. The adhesive 136 can have a viscosity upon application high enough that it is not pulled off the skin 111 by suction at the portions of the treatment site 105 not in contact with the liner 131. In some cases, however, some or all of the adhesive 136 at these portions of the treatment site 105 may be pulled off the skin 111 by suction. In these cases, the applicator 104 can include a filter (not shown) that reduces or eliminates clogging of suction lines and/or ports into which the liberated adhesive 136 is drawn.

Figure 22:
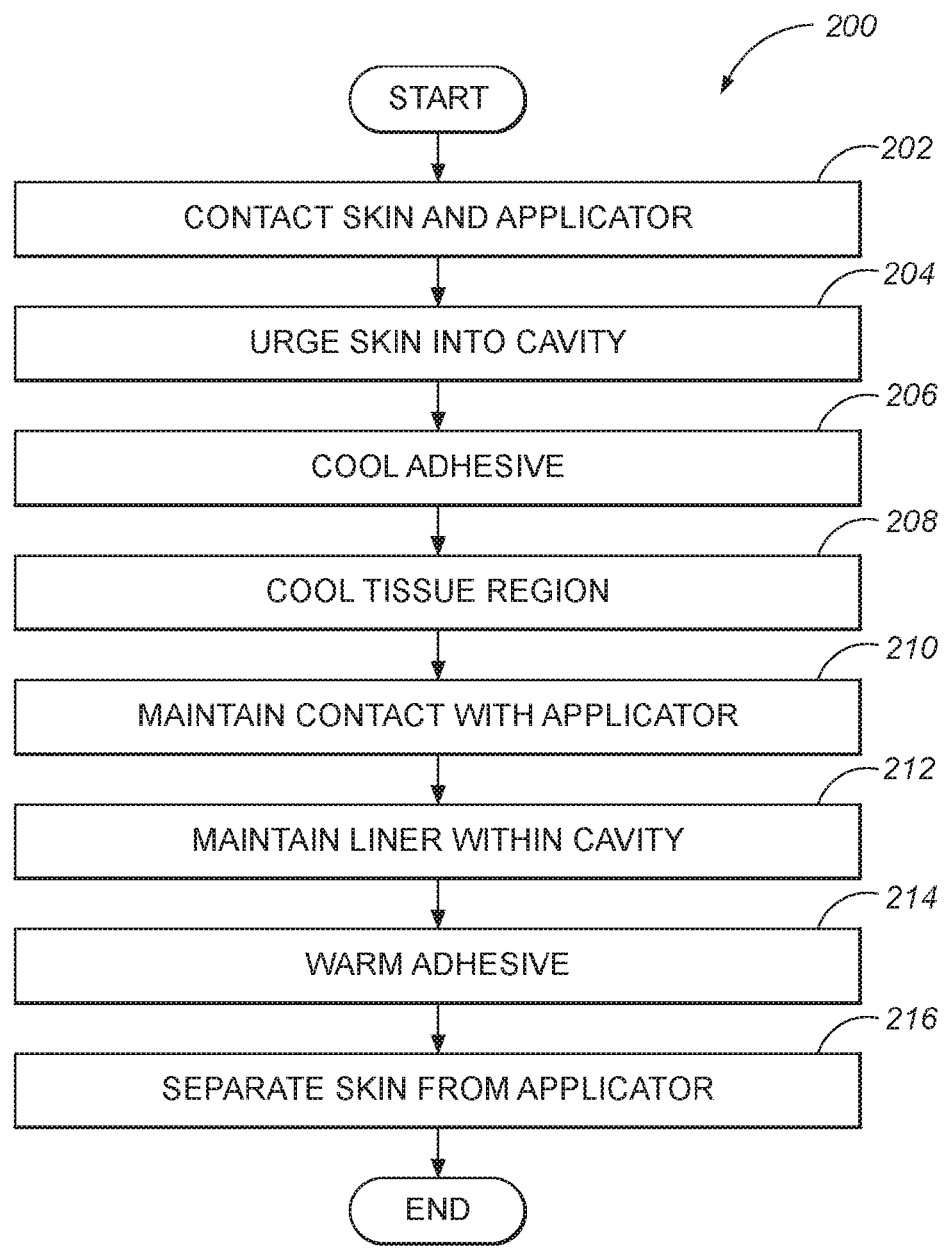
FIG. 22 is a flow chart illustrating a method for cooling a tissue region in accordance with an embodiment of the present invention.

FIG. 22 is a flow chart illustrating a method 200 for cooling a tissue region of a subject in accordance with an embodiment of the present invention. For simplicity, the method 200 will be further described primarily with reference to the applicator 104. It should be understood, however, that the method 200, when suitable, and/or portions of the method 200, when suitable, can be practiced with respect to any of the applicators 104, 170, 179, 182, or other applicators in accordance with embodiments of the present invention. With reference together to FIGS. 20-22 and various preceding figures as indicated, the method 200 can include contacting the skin 111 and the applicator 104 with the adhesive 136 therebetween (block 202). As discussed above, this can include applying (e.g., brushing, smearing, placing, etc.) the adhesive 136 onto the skin 111, onto the liner 131, and/or onto the heat-transfer surface 134 of the applicator 104, and then bringing the skin 111 and the applicator 104 into thermal and physical contact with one another. The adhesive 136 can be independent or carried by an absorbent substrate (e.g., the absorbent substrate 160 shown in FIG. 9). In at least some embodiments, the method 200 includes urging the skin 111 into the cavity 132 (block 204). For example, the method 200 can include urging the skin 111 into the cavity 132 at least partially by suction and/or at least partially by compression.

When the tissue 135 is in thermal and physical contact with the heat-transfer surface 134 via the skin 111 and via the adhesive 136, the method 200 can include cooling the adhesive 136 (block 206) and cooling the tissue 135 (block 208). Cooling the adhesive 136 can include cooling the adhesive 136 to a temperature no colder than a glass transition temperature of the adhesive 136, such as a temperature within a range from 1° C. warmer than the glass transition temperature of the adhesive 136 to 10° C. warmer than the glass transition temperature of the adhesive 136, e.g., to a temperature warmer by more than either of 1, 2, 3, 4, 5, 6, 7, 8, 9, or 10° C. In at least some cases, the temperature to which the adhesive 136 is cooled is within a range from either −25° C. to −1° C., −25° C. to −5° C., −20° C. to −8° C., or −18° C. to −10° C. Cooling the adhesive 136 can cryogenically strengthen an adhesive bond between the skin 111 and the heat-transfer surface 134. Cooling the tissue 135 can occur during cryogenic strengthening of the adhesive bond and/or after cryogenic strengthening of the adhesive bond. Cooling the tissue 135 can include cooling the tissue 135 via a viscous layer of the adhesive 136, via the composite structure including the absorbent substrate 160 and adhesive 136 (FIG. 9), and/or via the adhesive 136 in another suitable form for application between the applicator 104 and the skin 111. In at least some embodiments, the tissue 135 is cooled to a sufficiently low temperature to damage or otherwise disrupt subcutaneous lipid-rich cells and/or any other targeted structures in the skin or subcutaneous layer. In these and other embodiments, cooling the tissue 135 can include cooling the tissue 135 to colder than 0° C., −5° C., −10° C. or colder than another suitable threshold for at least 15 minutes.

While cooling the tissue 135, the method 200 can include maintaining thermal and physical contact between the tissue 135 and the heat-transfer surface 134 (block 210). The adhesive 136 can cause this thermal and physical contact to be more reliable than it would be if the adhesive 136 were not present. In at least some cases, the adhesive bond between the skin 111 and the heat-transfer surface 134 may become strong enough while cooling the tissue 135 to at least partially or totally substitute for suction and/or compression used to urge the tissue 135 into the cavity 132. In these and other cases, the method 200 can include reducing or eliminating suction and/or compression after cryogenically strengthening the adhesive bond and while cooling the tissue 135. The method 200 can further include maintaining a position of the liner 131 within the cavity 132 (block 212) while cooling the tissue 135. For example, the position of the liner 131 within the cavity 132 can be maintained at least primarily by suction and/or by another adhesive, which can but does not need to have any special properties. If rapid release of the tissue 135 from the applicator 104 is necessary while a strong adhesive bond between the skin 111 and the heat-transfer surface 134 is present via the adhesive 136, suction holding the liner 131 within the cavity 132 can be released and the tissue 135 can be removed from the cavity 132 with the liner 131 when a liner adhesive is not present. When a liner adhesive is present or when the liner 131 is not used, if rapid release of the tissue 135 from the applicator 104 is necessary, the applicator 104 can be rapidly rewarmed to warm the adhesive 136 to a temperature high enough such that the tissue 135 can be readily removed from the cavity 132.

As shown in FIG. 22, the method 200 can further include warming the adhesive 136 (block 214) after cooling the adhesive 136. This can weaken the adhesion between the skin 111 and the heat-transfer surface 134. In at least some embodiments, warming the adhesive 136 includes warming the adhesive 136 by at least 10° C. Furthermore, warming the adhesive 136 can include actively warming the adhesive 136 (e.g., using the thermoelectric element 152) and/or passively warming the adhesive 136 (e.g., by passing uncooled heat-transfer fluid through the fluid-cooled element 144. Warming the adhesive 136 can decrease the viscosity of the adhesive 136 to less than 1,000,000 centipoise. After warming the adhesive 136, the method 200 can include separating the skin 111 and the heat-transfer surface 134 (block 216).

Cooling treatments in accordance with at least some embodiments of the present invention can be used to reduce or eliminate targeted tissue in either the skin, subcutaneous layer, or other layers, and thereby cause the tissue to have a desired appearance. For example, treatment systems in accordance with embodiments of the present invention can perform medical treatments to provide therapeutic effects and/or cosmetic procedures for cosmetically beneficial effects. Without being bound by theory, the selective effect of cooling is believed to result in, for example, membrane disruption, cell shrinkage, disabling, disrupting, damaging, destroying, removing, killing, reducing, and/or other methods of lipid-rich cell and non-lipid rich cell alteration, and alteration of other tissue, either in the skin, subcutaneous tissue, or other tissue. Such alteration is believed to stem from one or more mechanisms acting alone or in combination. It is thought that such mechanism(s) trigger an apoptotic cascade, which is believed to be the dominant form of lipid-rich cell death by non-invasive cooling. In any of these embodiments, the effect of tissue cooling can be the selective reduction of lipid-rich cells by a desired mechanism of action, such as apoptosis, lipolysis, or the like. In some procedures, an applicator 104 can cool targeted tissue of a subject to a temperature in a range of from about −25° C. to about 20° C. In other embodiments, the cooling temperatures can be from about −20° C. to about 10° C., from about −18° C. to about 5° C., from about −15° C. to about 5° C., or from about −15° C. to about 0° C. In further embodiments, the cooling temperatures can be equal to or less than −5° C., −10° C., −15° C., or in yet another embodiment, from about −15° C. to about −25° C. Other cooling temperatures and temperature ranges can be used.

Apoptosis, also referred to as "programmed cell death", is a genetically-induced death mechanism by which cells self-destruct without incurring damage to surrounding tissues. An ordered series of biochemical events induce cells to morphologically change. These changes include cellular blebbing, loss of cell membrane asymmetry and attachment, cell shrinkage, chromatin condensation and chromosomal DNA fragmentation. Injury via an external stimulus, such as cold exposure, is one mechanism that can induce cellular apoptosis in cells, Nagle, W. A., Soloff, B. L., Moss, A. J. Jr., Henle, K. J. "Cultured Chinese Hamster Cells Undergo Apoptosis After Exposure to Cold but Nonfreezing Temperatures" *Cryobiology* 27, 439-451 (1990).

One aspect of apoptosis, in contrast to cellular necrosis (a traumatic form of cell death causing local inflammation), is that apoptotic cells express and display phagocytic markers on the surface of the cell membrane, thus marking the cells for phagocytosis by macrophages. As a result, phagocytes can engulf and remove the dying cells (e.g., the lipid-rich cells) without eliciting an immune response. Temperatures that elicit these apoptotic events in lipid-rich cells may contribute to long-lasting and/or permanent reduction and reshaping of subcutaneous adipose tissue.

One mechanism of apoptotic lipid-rich cell death by cooling is believed to involve localized crystallization of lipids within the adipocytes at temperatures that do not induce crystallization in non-lipid-rich cells. The crystallized lipids selectively may injure these cells, inducing apoptosis (and may also induce necrotic death if the crystallized lipids damage or rupture the bi-lipid membrane of the adipocyte). Another mechanism of injury involves the lipid phase transition of those lipids within the cell's bi-lipid membrane, which results in membrane disruption or dysfunction, thereby inducing apoptosis. This mechanism is well-documented for many cell types and may be active when adipocytes, or lipid-rich cells, are cooled, Mazur, P., "Cryobiology: the Freezing of Biological Systems" *Science,* 68: 939-949 (1970); Quinn, P. J., "A Lipid Phase Separation Model of Low Temperature Damage to Biological Membranes" *Cryobiology,* 22: 128-147 (1985); Rubinsky, B., "Principles of Low Temperature Preservation" *Heart Failure Reviews,* 8, 277-284 (2003).

Other possible mechanisms of adipocyte damage, described in U.S. Pat. No. 8,192,474, relate to ischemia/reperfusion injury that may occur under certain conditions when such cells are cooled as described herein. For instance, during treatment by cooling as described herein, the targeted adipose tissue may experience a restriction in blood supply and thus be starved of oxygen due to isolation as a result of applied pressure, cooling which may affect vasoconstriction in the cooled tissue, or the like. In addition to the ischemic damage caused by oxygen starvation and the buildup of metabolic waste products in the tissue during the period of restricted blood flow, restoration of blood flow after cooling treatment may additionally produce reperfusion injury to the adipocytes due to inflammation and oxidative damage that is known to occur when oxygenated blood is restored to tissue that has undergone a period of ischemia. This type of injury may be accelerated by exposing the adipocytes to an energy source (via, e.g., thermal, electrical, chemical, mechanical, acoustic, or other means) or otherwise increasing the blood flow rate in connection with or after cooling treatment as described herein. Increasing vasoconstriction in such adipose tissue by, e.g., various mechanical means (e.g., application of pressure or massage), chemical means or certain cooling conditions, as well as the local introduction of oxygen radical-forming compounds to stimulate inflammation and/or leukocyte activity in adipose tissue may also contribute to accelerating injury to such cells. Other yet-to-be understood mechanisms of injury may exist.

In addition to the apoptotic mechanisms involved in lipid-rich cell death, local cold exposure is also believed to induce lipolysis (i.e., fat metabolism) of lipid-rich cells and has been shown to enhance existing lipolysis which serves to further increase the reduction in subcutaneous lipid-rich cells, Vallerand, A. L., Zamecnik. J., Jones, P. J. H., Jacobs, I. "Cold Stress Increases Lipolysis, FFA Ra and TG/FFA Cycling in Humans" *Aviation, Space and Environmental Medicine,* 70, 42-50 (1999).

One expected advantage of the foregoing techniques is that the subcutaneous lipid-rich cells in the target region can be reduced generally without collateral damage to non-lipid-rich cells in the same region. In general, lipid-rich cells can be affected at low temperatures that do not affect non-lipid-rich cells. As a result, lipid-rich cells, such as those associated with highly localized adiposity (e.g., submental adiposity, submandibular adiposity, facial adiposity, etc.), can be affected while non-lipid-rich cells (e.g., myocytes) in the same generally region are not damaged. The unaffected non-lipid-rich cells can be located underneath lipid-rich cells (e.g., cells deeper than a subcutaneous layer of fat), in the dermis, in the epidermis, and/or at other locations.

In some procedures, the treatment system can remove heat from underlying tissue through the upper layers of tissue and create a thermal gradient with the coldest temperatures near the cooling surface, or surfaces, of the applicator (i.e., the temperature of the upper layer(s) of the skin can be lower than that of the targeted underlying cells). It may be challenging to reduce the temperature of the targeted cells low enough to be destructive to these target cells (e.g., induce apoptosis, cell death, etc.) while also maintaining the temperature of the upper and surface skin cells high enough so as to be protective (e.g., non-destructive). The temperature difference between these two thresholds can be small (e.g., approximately, 5° C. to about 10° C., less than 10° C., less than 15° C., etc.). Protection of the overlying cells (e.g., typically water-rich dermal and epidermal skin cells) from freeze damage during dermatological and related aesthetic procedures that involve sustained exposure to cold temperatures may include improving the freeze tolerance and/or freeze avoidance of these skin cells by using, for example, cryoprotectants for inhibiting or preventing such freeze damage. In at least some cases, the adhesive 136 acts as such a cryoprotectant. The adhesive can be used when tissue is cooled to temperatures above a freezing point of the tissue, when tissue is cooled to temperatures below a freezing point of the tissue where freezing does not occur due to supercooling, or alternatively be used in procedures where freezing of tissue is intended and caused to occur. Additional details regarding cryotherapies compatible with at least some embodiments of the present invention can be found, for example, in U.S. Patent Application Publication No. 2005/0251120, which is incorporated herein by reference in its entirety.

Adhesive Formulations

Figure 23:
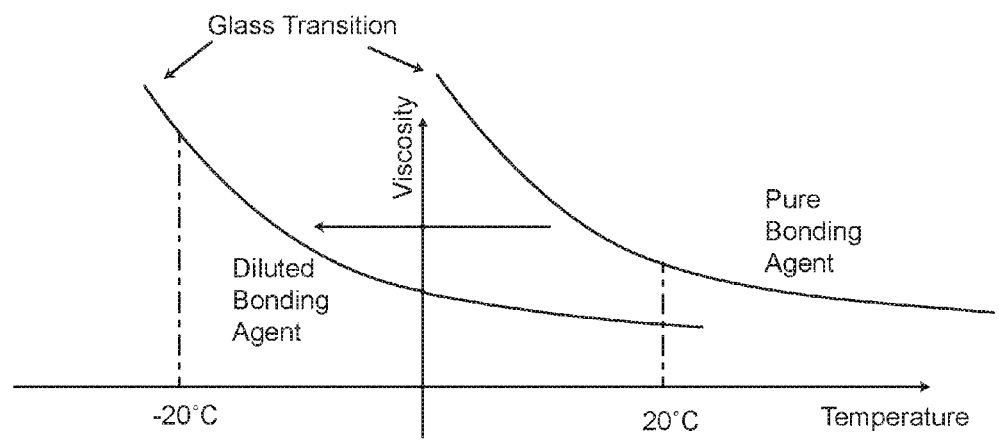
FIG. 23 is a plot of viscosity versus temperature for a pure bonding agent and for a diluted bonding agent.
Figure 24:
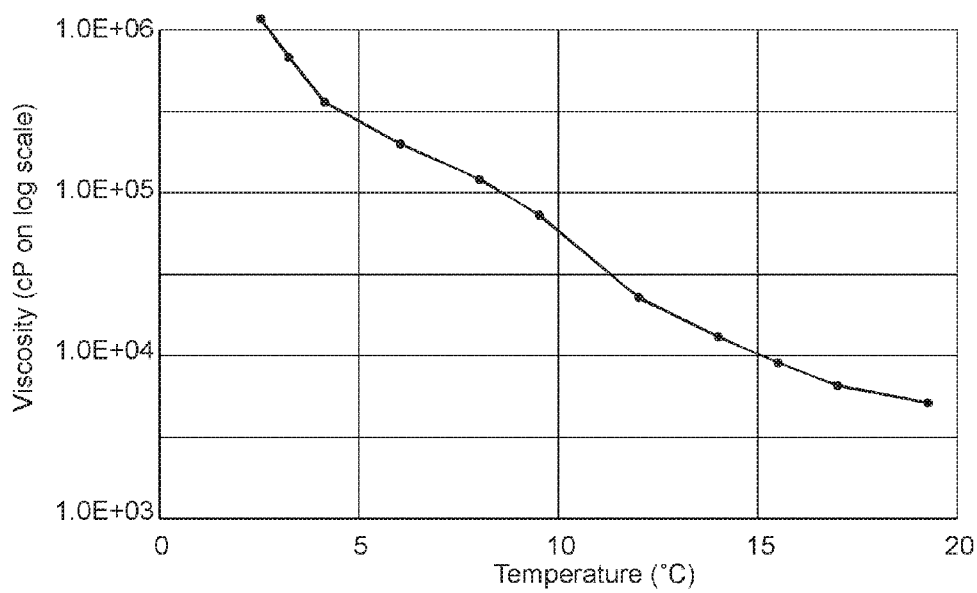
FIG. 24 is a plot of viscosity versus temperature for an adhesive including 70% v/v sucrose acetate isobutyrate (SAIB) and 30% v/v dipropylene glycol.
Figure 25:
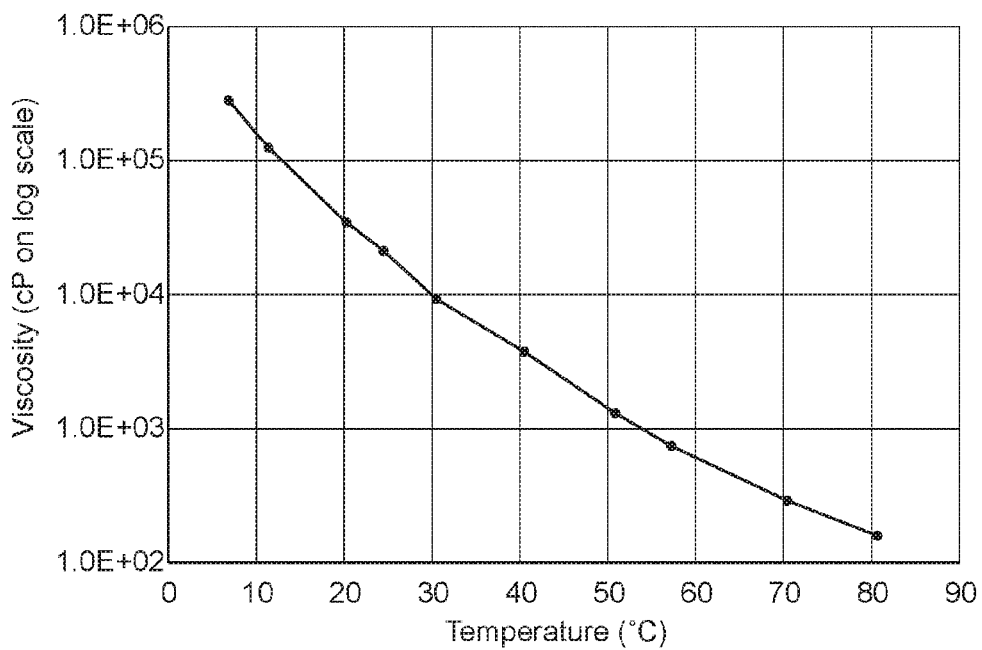
FIG. 25 is a plot of viscosity versus temperature for an adhesive including 43% w/w fructose and 57% w/w glycerol.

Adhesives in accordance with embodiments of the present invention (e.g., the adhesive 136 described above) can include a bonding agent that significantly increases in viscosity and tack (i.e., stickiness) when cooled. The adhesives can further include a viscosity-reducing agent mixed with the bonding agent to modify the viscosity temperature-dependence of the resulting adhesive, to modify that tack temperature-dependence of the resulting adhesive, and/or to lower the glass transition temperature of the resulting adhesive. FIG. 23 is a plot of viscosity versus temperature for a pure bonding agent (right) and for a bonding agent diluted with a viscosity-reducing agent (left). As shown in FIG. 23, the addition of the viscosity-reducing agent lowers the glass transition temperature of the adhesive and shifts the region of highly temperature-dependent viscosity for the adhesive to be between −20° C. and 20° C. In some cases, the bonding agent is a solid at room temperatures, and the viscosity-reducing agent is a liquid solvent at room temperature with a relatively high solubility limit for the bonding agent, such as greater than 50% w/w, 60% w/w, 70% w/w, or a higher threshold. In other cases, the viscosity-reducing agent and the bonding agent can be miscible liquids at room temperature.

The relative proportions of the bonding agent and the viscosity-reducing agent in the adhesive can be selected to cause a cooling temperature range in which the adhesive significantly increases in viscosity and stickiness to correspond to a cooling temperature range of a treatment in which the adhesive is to be used. The targeted temperature range, for example, can extend from an application temperature (e.g., room temperature or body temperature) to a chilled temperature suitable for damaging or otherwise disrupting subcutaneous lipid-rich cells and/or any other targeted structures in the skin or subcutaneous layer (e.g., −20° C., −15° C., −10° C., or −5° C.). The relative proportions of the bonding agent and the viscosity-reducing agent in the adhesive can additionally or alternatively be selected based on the solubility limit of the bonding agent in the viscosity-reducing agent. For example, the concentration of the bonding agent in the adhesive can be selected to be a maximum concentration (thereby maximizing the viscosity and the tack of the adhesive) that still adequately suppresses recrystallization of the bonding agent during normal storage and use of the adhesive.

Adhesives in accordance with at least some embodiments of the present invention have a viscosity less than 500,000 centipoise (e.g., within a range from 5,000 centipoise to 500,000 centipoise) at 20° C. and a viscosity greater than 3,000,000 centipoise at −15° C. In these and other cases, the viscosities of the adhesives at −10° C. can be greater than the viscosities of the adhesives at 20° C. by at least 1,000% (e.g., by at least 3,000%, 5,000%, or 10,000%) on a centipoise scale. Furthermore, the adhesives can have a first level of tensile adhesion to human skin at 20° C. and a second level of tensile adhesion to human skin at −10° C. greater that the first level of tensile adhesion by a factor of more than 1.25×, 1.5×, 2×, 3×, 4×, 5×, 6×, 7×, 10×, 20×, or 30×. This tensile adhesion to human skin can be tested by applying a normal pulling force to a flat layer of adhesive disposed between an applicator and a skin analog.

The bonding agent can be a modified or unmodified saccharide. These compounds can be well suited for this application because they tend to become both increasingly viscous and increasingly sticky when cooled to temperatures above their glass transition temperatures. As discussed above, this behavior is desirable for enhancing adhesion between skin and an applicator during a cooling treatment that involves using the applicator to cool and thereby damage or otherwise disrupt subcutaneous lipid-rich cells and/or any other targeted structures in the skin or subcutaneous layer. The strength of the bond between the skin and the applicator may benefit from both high viscosity (e.g., for maintaining the internal integrity of the bond) and high tack (e.g., for maintaining the integrity of the bonded interface between the adhesive and the skin). Saccharides also tend to be biocompatible, nontoxic, and water soluble, with the latter being useful to facilitate cleaning. Examples of saccharides suitable for use in methods in accordance with at least some embodiments of the present invention include modified and unmodified monosaccharides (e.g., glucose and fructose) and modified and unmodified disaccharides (e.g., sucrose, maltose, and trehalose). Although experimental data for glucose, fructose, and sucrose acetate isobutyrate (SAIB) are described below, it should be understood that other modified and unmodified saccharides are also expected to be suitable for use in methods in accordance with embodiments of the present invention.

The tendency of saccharides and saccharide derivatives to become both increasingly viscous and increasingly sticky when cooled typically does not apply below their glass transition temperatures. For example, when pure SAIB, pure glucose, or pure fructose transitions to its glass state, it becomes brittle and no longer sticky. The glass transition temperatures for pure SAIB, pure glucose, and pure fructose are all at or above 0° C. Thus, these saccharides would turn to glass if used in their pure forms in cooling procedures that involve cooling to below 0° C., which is typical of cooling procedures that disrupt subcutaneous lipid-rich cells. To address this problem, the bonding agent can be mixed with a viscosity-reducing agent at a ratio that moves the glass-transition temperature of the resulting adhesive to be colder than a chilled temperature characteristic of a cooling procedure in which the adhesive is to be used. In at least some cases, the glass transition temperature of the bonding agent is modified in this manner such that the glass transition temperature of the corresponding adhesive is colder than −20° C., such as colder than −30° C. Suitable viscosity-reducing agents include glycols (e.g., propylene glycol, dipropylene glycol, and glycerol) and other polar, biocompatible oil-like compounds. These compounds tend to be good solvents of saccharides and to have relatively low glass transition temperatures.

Adhesives in accordance with at least some embodiments of the present invention contain less than 3% w/w water. For example, bonding agents, viscosity-reducing agents, and adhesives in accordance with embodiments of the present invention can be anhydrous. The presence of water as a co-solvent tends to reduce the solubility limit of viscosity-reducing agents for modified or unmodified saccharides. Thus, reducing or eliminating water from adhesives including saccharide-based bonding agents may increase the solubility limits of these adhesives for their constituent bonding agents. This, in turn, may increase the maximum viscosity and tack of the adhesives within targeted temperature ranges for cooling procedures while still adequately suppressing recrystallization of the bonding agents during normal storage and use of the adhesives. Reducing or eliminating water from adhesives including saccharide-based bonding agents also may enhance the antimicrobial properties of the adhesives. In the absence of water, saccharide-based bonding agents typically do not support the growth of bacteria and fungi. This can facilitate manufacturing and storage of adhesives including these bonding agents.

In at least some cases, it is desirable for the adhesives to be as viscous as possible. For example, in addition to having a sufficiently high chilled viscosity to adhere an applicator to a subject's skin during a cooling procedure, it may also be helpful for an adhesive to have a sufficiently high application viscosity (e.g., at room temperature and/or at body temperature) to facilitate application of the adhesive before cooling begins or before significant cooling is achieved. High application viscosity, for example, may suppress excessive dripping of the adhesive and/or squeezing of the adhesive out of an interface between an applicator and a subject's skin. Relatedly, the adhesive can include a gelling agent that enhances its ability to retain its shape upon application. Examples of suitable gelling agents include polysaccharides (e.g., agar) and proteins (e.g., gelatin). The gelling agent can be present at a relatively low concentration (e.g., less than 5% w/w) such that its presence does not unduly interfere with other desirable properties of the adhesive.

In addition to or instead of reducing or eliminating water as a co-solvent, adhesives in accordance with at least some embodiments of the present invention include bonding agents that include more than one modified or unmodified saccharide. For example, an adhesive in accordance with a particular embodiment of the present invention includes a bonding agent that is a combination of a modified or unmodified first saccharide (e.g., one of sucrose, fructose, and glucose) and a modified or unmodified second saccharide (e.g., another of sucrose, fructose, and glucose). Each of the modified or unmodified first saccharide and the modified or unmodified second saccharide can be present at a concentration relative to the overall bonding agent within a range from 5% w/w to 95% w/w. As with reducing or eliminating water, the presence of more than one modified or unmodified saccharide in the bonding agent can increase the solubility limit of the corresponding adhesive for the bonding agent. An adhesive in accordance a particular embodiment of the present invention includes a bonding agent that includes modified or unmodified fructose and modified or unmodified glucose. Other combinations of modified or unmodified saccharides are also expected to be desirable for use as bonding agents.

As discussed above in relation to the embedded thermal sensor 164 (FIG. 11), it may be useful to detect a thermal signature associated with a skin freeze during a cooling procedure. In at least some cases, the thermal properties of adhesives in accordance with embodiments of the present invention facilitate this detection. For example, the thermal conductivity of the adhesive can increase as the adhesive is cooled from an application temperature (e.g., room temperature or body temperature) to a chilled temperature suitable for suitable for damaging or otherwise disrupting subcutaneous lipid-rich cells and/or any other targeted structures in the skin or subcutaneous layer (e.g., −20° C., −15° C., −10° C., or −5° C.). Thus, the rate at which the adhesive conveys a thermal signal may be enhanced during the coldest portion of a cooling process, when the need for detecting skin freezes is greatest. Furthermore, the thermal conductivity of the adhesive can be relatively consistent within a range of chilled temperatures suitable for suitable for damaging or otherwise disrupting subcutaneous lipid-rich cells and/or any other targeted structures in the skin or subcutaneous layer (e.g., a range from −5° C. to −20° C.). For example, the thermal conductivity of the adhesive at −5° C. and the thermal conductivity of the adhesive at −20° C. may differ by less than 2% on a watts-per-meter-kelvin scale. This can be useful for facilitating differentiating a thermal signature associated with a skin freeze from background thermal information during a cooling procedure.

Adhesives in accordance with embodiments of the present invention can further include additives that enhances their thermal conductivity. For example, a given adhesive can include dispersed particles of a highly thermally conductive material, such as zinc oxide. The thermally conductive particles can be incorporated into the adhesive by sonication or a similar mixing process to avoid aggregation. Furthermore, the adhesive can include a stabilizing agent (e.g., a compatible electrostatic and/or steric stabilizing agent) that promotes even distribution of the particles throughout the adhesive. Accordingly, the adhesive can be a stable suspension at room temperature. In some cases, the particles are configured to enhance the thermal conductivity of the adhesive when in a random distribution within the adhesive. In other cases, the particles are configured to enhance the thermal conductivity of the adhesive when in an ordered distribution within the adhesive. For example, thermally conductive particles within an adhesive in accordance with a particular embodiment of the present invention are configured to be magnetically shifted in situ to increase the thermal conductivity of the adhesive. An applicator used with the adhesive can be configured to apply a magnetic field that causes the particles to form channels for preferential transmission of thermal energy between the applicator and a subject's skin. These and other thermally conductive particles in accordance with embodiments of the present invention can have an average effective diameter greater than 100 nanometers to reduce or eliminate their migration through a subject's skin during a cooling procedure.

Adhesives in accordance with embodiments of the present invention can have benefits in addition to providing adhesion between an applicator and a subject's skin during a cooling procedure. For example, the viscosity-reducing agents of some adhesives may suppress skin freezing by deactivating potential ice nucleation sites. As another example, the bonding agents of some adhesives may absorb into or even through a subject's skin and provide cryoprotection to non-targeted cells. Similarly, when a saccharide-based pretreatment is used on a subject's skin for cryoprotection, the presence of a saccharide-based bonding agent in an adhesive applied after the pretreatment may establish a concentration gradient that suppresses outgoing migration of a cryoprotective saccharide absorbed during the pretreatment. Other advantages of adhesives in accordance with embodiments of the present invention in addition to or instead of the foregoing advantages are also possible.

EXPERIMENTAL EXAMPLES

1.) Viscosity Dependence on Concentration (SAIB/DPG Adhesive)

Adhesives including sucrose acetate isobutyrate (SAIB) and dipropylene glycol (DPG) were prepared by mixing these two constituent materials at 60° C. Specifically, SAIB/DPG adhesives with 70, 75 and 80% v/v SAIB content were prepared and their viscosities were measured using a Brookfield viscometer. Table 1 below shows that by adding DPG to SAIB, the viscosity of the mixture can be tuned, with more DPG content leading to lower viscosity at a fixed temperature.

TABLE 1

| Viscosity Dependence on SAIB Concentration | |
|---|---|
| SAIB % v/v | Viscosity (cP) |
| 70 | 1700 |
| 75 | 2800 |
| 80 | 9500 |

2.) Viscosity Dependence on Shear Rate (SAIB/DPG Adhesive)

The viscosity of adhesive including 70% v/v SAIB and 30% v/v DPG was tested using a Brookfield viscometer to determine shear-rate dependence. The results, shown in Table 2 below, indicate that the tested adhesive was shear-rate dependent, and thus could be modeled as a non-Newtonian fluid.

TABLE 2

| Viscosity Dependence on Shear Rate | |
|---|---|
| RPM | Viscosity (cP) |
| 1.5 | 2050 |
| 3 | 2550 |
| 6 | 2780 |
| 12 | 2883 |

3.) Viscosity Dependence on Temperature (SAIB/DPG Adhesive)

The viscosity of adhesive including 70% v/v SAIB and 30% v/v DPG was tested using a Brookfield viscometer to determine temperature dependence. The results, shown in FIG. 24, indicate that the viscosity of the tested adhesive increased by 3 orders of magnitude as the temperature of the adhesive decreased from about 20° C. to about 0° C.

4.) Glass Transition Temperature (SAIB/DPG Adhesive)

Glass transition was observed relative to temperature for SAIB/DPG adhesives of different SAIB concentrations. The results, shown in Table 3 below, indicate that the tested adhesive including 80% v/v SAIB and 20% v/v DPG was capable of supporting cooling treatments at temperatures as cold as −15° C., and that the tested adhesive including 70% v/v SAIB and 30% v/v DPG was capable of supporting cooling treatments at temperatures as cold as −20° C. In Table 3, Y=glassy state and N=non-glassy state.

TABLE 3

Glass Transition of SAIB/DPG

| SAIB % v/v | 0° C. | −5° C. | −10° C. | −12.5° C. | −15° C. | −17.5° C. | −20° C. | −22.5° C. | −25° C. |
|---|---|---|---|---|---|---|---|---|---|
| 100 | Y | Y | Y | Y | Y | Y | Y | Y | Y |
| 90 | N | N | N | N | Y | Y | Y | Y | Y |
| 80 | N | N | N | N | N | Y | Y | Y | Y |
| 70 | N | N | N | N | N | N | N | Y | Y |
| 60 | N | N | N | N | N | N | N | N | N |

5.) Freeze Prevention (SAIB/DPG Adhesive)

Adhesive including 70% v/v SAIB and 30% v/v DPG at −10° C. was found not to trigger an immediate, on-command skin freeze when contacted with supercooled skin at −10° C. The potential for the tested adhesive to cause freezes, therefore, was tested by cooling skin in the presence of the adhesive to −10° C. and holding the tissue at −10° C. until a freeze was detected by a thermal camera. The freezes that were detected in this manner were all initiated within the skin. This indicates that the tested adhesive likely had little if any role in initiating the freezes.

6.) Comparison to Non-Adhesive Cryoprotectant (SAIB/DPG Adhesive)

Adhesive including 70% v/v SAIB and 30% v/v DPG was compared to a non-adhesive cryoprotectant for spontaneous skin freezing temperature and thermal properties. The tested non-adhesive cryoprotectant was a mixture of 50% w/w propylene glycol, 1.5% w/w hydroxymethyl cellulose, and 48.5% w/w water. Skin to be tested was cleaned by pre-treatment skin wipes prior to application of 100 µL of either the tested adhesive or the non-adhesive cryoprotectant over the treatment sites (1 square inch). Cooling was applied using a temperature setpoint profile including an initial drop from 10° C. to −18° C., followed by a drop of 2° C. at about 2.4 minutes, a drop of 2° C. at about 3.6 minutes, a drop of 2° C. at about 4.8 minutes, and a drop of 1° C. at about 6.0 minutes, resulting in a temperature of −25° C. The tested adhesive and the non-adhesive cryoprotectant were found to correspond to mean spontaneous skin freeze temperatures of −22.79° C. and −23.26° C., respectively. The statistical test (two-tailed T-test) gave a p-value of p=0.93 using a significance level of α=0.05, indicating that the tested adhesive and the non-adhesive cryoprotectant likely correspond to the same skin spontaneous freezing temperature.

The profile of skin temperature change over time for the tested adhesive and the non-adhesive cryoprotectant were also compared. Test treatments using the tested adhesive and the non-adhesive cryoprotectant at a ramping rate of 1.55° C./second and a target temperature of −18° C. were performed. The profiles of skin temperature change over time and the time to reach the target temperature were found to be approximately the same for the tested adhesive and the non-adhesive cryoprotectant.

7.) Viscosity Dependence on Temperature (Fructose/Glycerol Adhesive)

Adhesive including 43% w/w fructose and 57% w/w glycerol was tested using a Brookfield viscometer to determine temperature dependence. The results, shown in FIG. 25, indicate that the viscosity of the adhesive increased several orders of magnitude as the temperature of the adhesive was lowered from about 80° C. to close to 0° C. For sub-zero temperatures, the viscosity of the adhesive was beyond the measurable range of the viscometer.

8.) Glass Transition Temperature (Fructose/Glycerol Adhesive)

The glass transition temperature of adhesive including 43% w/w fructose and 57% w/w glycerol was determined theoretically and experimentally. The theoretical calculation, shown below, yielded a glass transition temperature of −45.082° C.

$$T_g = \frac{\omega_1 T_{g1} + k\omega_2 T_{g2}}{\omega_1 + k\omega_2}$$

$\omega_1$=weight fraction of 1st component (fructose)=0.571
$\omega_2$=weight fraction of 2nd component (glycerol)=0.429
k=change in specific heat capacity ratio between 1st and 2nd component through their glass transition=1.085/0.75
$T_{g1}$=glass transition temperature of 1st component (fructose)=7° C.
$T_{g2}$=glass transition temperature of 2nd component (glycerol)=−93° C.

The experimental measurement of the glass transition temperature of the adhesive was performed by Differential Scanning calorimetry (DSC) Thermal Analysis. In a DSC apparatus, the difference in heat flow to the sample and to a reference sample at the same temperature, was recorded as a function of temperature. This allows the heat effects associated with phase transitions, including glass transition, to be measured as a function of temperature. The experimental measurement yielded a glass transition temperature of −45.35° C. for the tested adhesive, which agreed well with the theoretical calculation.

9.) Tensile Adhesion (Fructose/Glycerol Adhesive)

Pieces of rayon cloth loaded with adhesive including 43% w/w fructose and 57% w/w glycerol were placed between an applicator and a pulling block. The applicator was then used to cool the adhesive-loaded cloth to a pre-determined temperature. After the adhesive-loaded cloth equilibrated at the pre-determined temperature, normal pulling force was applied using an ESM303 Motorized Force Tester (Mark-10 Corporation of Copiague, N.Y.) at a constant velocity of 0.5 in/min and with a travel distance of 0.25 in. The peak force was recorded before the detachment of the pulling block. The results, shown in Table 4 below, indicate that the peak tensile adhesion force increased from 3.4 lbF to 34.3 lbF when the temperature of the adhesive decreased from 40° C. to −22° C.

TABLE 4

Adhesion Dependence on Temperature

| Adhesion Force (lbF) | Temperature (° C.) |
|---|---|
| 3.4 | 40 |
| 7.0 | 25 |
| 15.5 | 10 |

TABLE 4-continued

Adhesion Dependence on Temperature

| Adhesion Force (lbF) | Temperature (° C.) |
|---|---|
| 21.3 | −2 |
| 27.0 | −12 |
| 34.3 | −22 |

10.) Thermal Properties (Fructose/Glycerol Adhesive)

Figure 26:
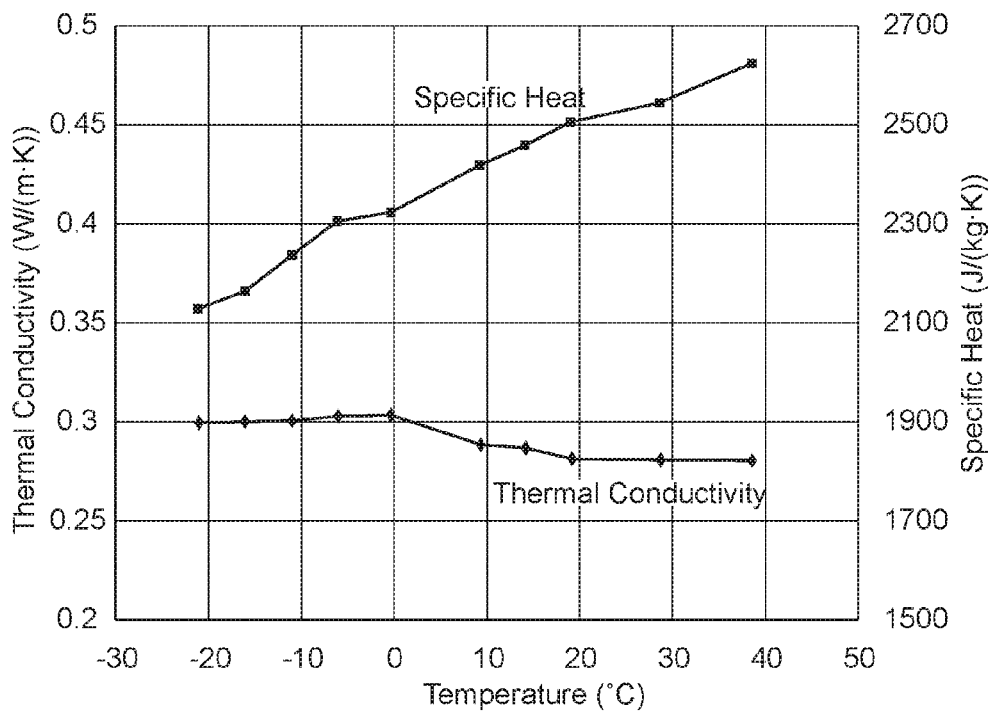
FIG. 26 is a plot of specific heat and thermal conductivity versus temperature for an adhesive including 43% w/w fructose and 57% w/w glycerol.
Figure 27:
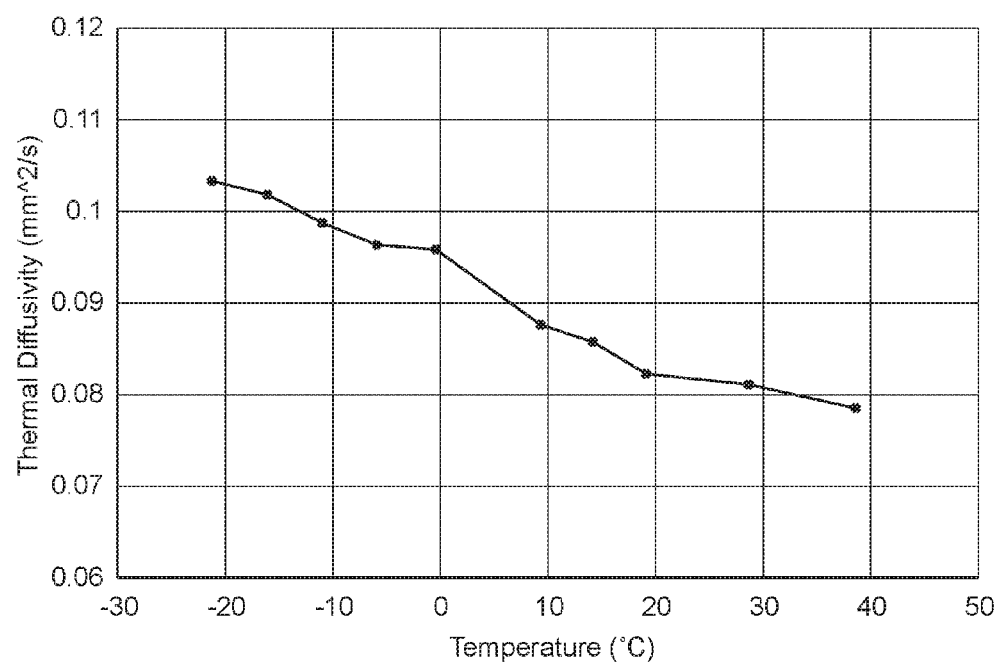
FIG. 27 is a plot of thermal diffusivity versus temperature for an adhesive including 43% w/w fructose and 57% w/w glycerol.

The thermal properties of pieces of fabric loaded with adhesive including 43% w/w fructose and 57% w/w glycerol were tested using a Linseis Transient Hot Bridge (THB). The THB was able to measure thermal conductivity in the range of 0.01 to 1 W/mK. A cooling chamber was used to measure temperature dependent properties at equilibrium. The density of the tested adhesive was assumed to be 1.363 g/cm$^3$. The results of this testing are shown in FIG. 26 (plot of specific heat and thermal conductivity versus temperature) and FIG. 27 (plot of thermal diffusivity versus temperature). The thermal data shows that as the tested sample cools, it becomes more efficient as a thermally conductive layer. Moreover, the thermal conductivity is relatively constant below 0° C. The thermal conductivity of about 0.3 W/(m·K) at temperatures below 0° C. is sufficiently high to allow for rapid detection of heat released by a skin freeze.

11.) Glass Transition Temperature (Glucose/Glycerol Adhesive)

A piece of paper towel loaded with adhesive including 80% v/v glucose syrup with a dextrose equivalent of 44 and 20% v/v glycerol was placed between an applicator and a 500 g weight. The applicator was then used to cool the adhesive-loaded paper towel from 10° C. to −10° C. at a cooling rate of 0.5° C./s. After the cooling and after being held at −10° C. for 3 minutes, the applicator was inverted and the weight suspended. By this test, the tensile strength of the adhesive-loaded paper towel was found to be sufficient to prevent the weight from detaching from the applicator in response to gravity.

12.) Viscosity at 21.5° C. (Fructose/Glycerol Adhesive and Fructose/Glucose/Glycerol Adhesive)

The viscosity at 21.5° C. of adhesives having three different formulations were tested using a Brookfield viscometer. The results shown in Table 5 below indicate that increasing the total saccharide concentration from 43% w/w to 55% w/w significantly increases the viscosity of the adhesive at 21.5° C. Use of two different saccharides (fructose and glucose in this case) allowed for this increase while still adequately suppressing recrystallization of the saccharides.

TABLE 5

Viscosity at 21.5° C.

| Adhesive | Formulation | Viscosity (cP) |
|---|---|---|
| 1 | 43% w/w fructose, 57% w/w glycerol | 29,700 |
| 2 | 29% w/w fructose, 14% w/w glucose, 57% w/w glycerol | 30,100 |
| 3 | 33% w/w fructose, 22% w/w glucose, 45% w/w glycerol | 89,200 |

12.) Thermal Properties (Fructose/Glucose/Glycerol Adhesive)

The thermal conductivity at −9.2° C., 6.4° C. and 22.4° C. of adhesives having three different formulations were tested as described in Example 10 above. The results shown in Table 6 below indicate that all three of the tested adhesives had sufficient thermal conductivity to allow for freeze detection during a cooling procedure.

TABLE 6

Thermal Conductivity at −9.2° C., 6.4° C. and 22.4° C.

| Adhesive | Formulation | Temperature (° C.) | Thermal Conductivity (W/(mK)) |
|---|---|---|---|
| 1 | 43% w/w fructose, 57% w/w glycerol | −9.2° C. | 0.3 |
| 1 | 43% w/w fructose, 57% w/w glycerol | 6.4° C. | 0.3 |
| 1 | 43% w/w fructose, 57% w/w glycerol | 22.4° C. | 0.3 |
| 2 | 29% w/w fructose, 14% w/w glucose, 57% w/w glycerol | −9.2° C. | 0.3 |
| 2 | 29% w/w fructose, 14% w/w glucose, 57% w/w glycerol | 6.4° C. | 0.29 |
| 2 | 29% w/w fructose, 14% w/w glucose, 57% w/w glycerol | 22.4° C. | 0.29 |
| 3 | 33% w/w fructose, 22% w/w 4 glucose, 5% w/w glycerol | −9.2° C. | 0.31 |
| 3 | 33% w/w fructose, 22% w/w glucose, 45% w/w glycerol | 6.4° C. | 0.3 |
| 3 | 33% w/w fructose, 22% w/w glucose, 45% w/w glycerol | 22.4° C. | 0.29 |

13.) Other Tested Adhesives

In addition to the adhesive formulations discussed above, adhesives having the following formulations were tested for temperature-dependent adhesion: (a) 43% w/w fructose and 57% w/w propylene glycol, (b) 43% w/w fructose and 57% w/w di-propylene glycol, and (c) 33% w/w glucose and 67% w/w glycerol. These adhesives were all found to have temperature-dependent adhesion similar to that of the adhesive including 43% w/w fructose and 57% w/w glycerol, as described in Example 9 above.

CONCLUSION

Various embodiments of the invention are described above. It will be appreciated that details set forth above are provided to describe the embodiments in a manner sufficient to enable a person skilled in the relevant art to make and use the disclosed embodiments. Several of the details and advantages, however, may not be necessary to practice some embodiments. Additionally, some well-known structures or functions may not be shown or described in detail, so as to avoid unnecessarily obscuring the relevant description of the various embodiments. Although some embodiments may be within the scope of the invention, they may not be described in detail with respect to the Figures. Furthermore, features, structures, or characteristics of various embodiments may be combined in any suitable manner. Moreover, one skilled in the art will recognize that there are a number of other technologies that could be used to perform functions similar to those described above. While processes or acts are presented in a given order, alternative embodiments may perform the processes or acts in a different order, and some processes or acts may be modified, deleted, and/or moved. The headings provided herein are for convenience only and do not interpret the scope or meaning of the described invention.

Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. Use of the word "or" in reference to a list of two or more items covers all of the following interpretations of the word: any of the items in the list, all of the items in the list, and any combination of the items in the list. Furthermore, the phrase "at least one of A, B, and C, etc." is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

Any patents, applications and other references, including any that may be listed in accompanying filing papers, are incorporated herein by reference. Aspects of the described invention can be modified, if necessary, to employ the systems, functions, and concepts of the various references described above to provide yet further embodiments. These and other changes can be made in light of the above Detailed Description. While the above description details certain embodiments and describes the best mode contemplated, no matter how detailed, various changes can be made. Implementation details may vary considerably, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

We claim:

1. A method for cooling a tissue region of a human subject having skin, the method comprising:
    applying an applicator to the subject's skin such that an adhesive is disposed between a heat-transfer surface of the applicator and the subject's skin; and
    cooling the adhesive via the heat-transfer surface of the applicator while cooling the tissue region to a sufficiently low temperature to damage tissue at the tissue region,
    wherein cooling the adhesive reversibly increases tensile adhesion between the subject's skin and the heat-transfer surface of the applicator by a factor of at least 1.25.

2. The method of claim 1 wherein the tissue includes subcutaneous lipid-rich cells.

3. The method of claim 1 wherein the tissue includes skin cells.

4. The method of claim 1 wherein cooling the adhesive reversibly increases tensile adhesion between the subject's skin and the heat-transfer surface of the applicator by a factor of at least 2.

5. The method of claim 1 wherein the adhesive has a glass transition temperature colder than −20° C.

6. The method of claim 1 wherein cooling the adhesive includes cooling the adhesive to no colder than a glass transition temperature of the adhesive, and wherein cooling the adhesive increases a viscosity of the adhesive by at least 1,000% on a centipoise scale.

7. The method of claim 1 wherein cooling the adhesive includes cooling the adhesive to no colder than a glass transition temperature of the adhesive, and wherein cooling the adhesive increases a viscosity of the adhesive by at least 10,000% on a centipoise scale.

8. The method of claim 1 wherein cooling the adhesive includes cooling the adhesive to a temperature within a range from 1° C. warmer than a glass transition temperature of the adhesive to 10° C. warmer than the glass transition temperature of the adhesive.

9. The method of claim 1 wherein the heat-transfer surface of the applicator is durable, and wherein applying the applicator to the subject's skin includes applying the applicator to the subject's skin such that the adhesive is disposed directly between the heat-transfer surface of the applicator and the subject's skin.

10. The method of claim 1, further comprising applying the adhesive to the subject's skin before applying the applicator to the subject's skin and while the adhesive has a viscosity within a range from 5,000 to 500,000 centipoise.

11. The method of claim 10 wherein cooling the adhesive increases the viscosity of the adhesive to a viscosity within a range from 3,000,000 centipoise to a maximum viscosity of the adhesive at temperatures warmer than a glass transition temperature of the adhesive.

12. The method of claim 1 wherein cooling the adhesive increases a thermal conductivity of the adhesive.

13. The method of claim 1 wherein cooling the adhesive stabilizes a thermal conductivity of the adhesive.

14. The method of claim 1, further comprising:
    heating the adhesive via the heat-transfer surface of the applicator after cooling the adhesive to reversibly decrease the tensile adhesion; and
    separating the subject's skin from the applicator after heating the adhesive.

15. The method of claim 14 wherein cooling the adhesive increases a viscosity of the adhesive to a viscosity within a range from 3,000,000 centipoise to a maximum viscosity of the adhesive at temperatures warmer than a glass transition temperature of the adhesive, and wherein heating the adhesive decreases the viscosity of the adhesive to less than 1,000,000 centipoise.

16. The method of claim 1 wherein applying the applicator to the subject's skin includes applying the applicator to the subject's skin such that an absorbent substrate is disposed between the heat-transfer surface of the applicator and the subject's skin, and wherein the substrate carries the adhesive.

17. The method of claim 16 wherein the substrate is a stretchable fabric including either metal fibers or carbon fibers.

18. The method of claim 16 wherein the substrate is a stretchable fabric including fibers having a thermally conductive coating.

19. The method of claim 16, further comprising elastically deforming the substrate while applying the applicator to the subject's skin.

20. The method of claim 16, further comprising inelastically deforming the substrate while applying the applicator to the subject's skin.

21. The method of claim 16 wherein applying the applicator to the subject's skin includes applying the applicator to the subject's skin such that a removable liner is disposed between the heat-transfer surface of the applicator and the substrate.

22. The method of claim 21 wherein the adhesive is a first adhesive, and wherein applying the applicator to the subject's skin includes applying the applicator to the subject's skin such that a second adhesive is disposed between the heat-transfer surface of the applicator and the liner.

23. The method of claim 1, further comprising applying a viscous layer of the adhesive to the subject's skin before applying the applicator to the subject's skin, wherein the viscous layer has an average thickness within a range from 0.1 to 1 millimeter, and wherein applying the viscous layer includes brushing and/or smearing the adhesive onto the subject's skin to form the viscous layer.

24. The method of claim 1 wherein the adhesive includes a gelling agent.

25. The method of claim 24 wherein the gelling agent is either a polysaccharide or a protein.

26. The method of claim 1 wherein, while applying the applicator to the subject's skin, the adhesive is a suspension including thermally conductive particles having an average effective diameter greater than 100 nanometers.

27. The method of claim 26, further comprising applying a magnetic field to the adhesive while cooling the adhesive, wherein applying the magnetic field shifts the particles within the adhesive and thereby increases a thermal conductivity of the adhesive.

\* \* \* \* \*